(12) United States Patent
Janssens et al.

(10) Patent No.: US 7,407,969 B2
(45) Date of Patent: Aug. 5, 2008

(54) RESPIRATORY SYNCYTIAL VIRUS REPLICATION INHIBITORS

(75) Inventors: Frans Eduard Janssens, Bonheiden (BE); Jean Fernand Armand Lacrampe, Le Mesnil-Esnard (FR); Jerome Emile Geroges Guilemont, Ande (FR); Marc G Venet, Le Mesnil-Esnard (FR); Koenraad Jozef Lodewijk Marcel Andries, Beerse (BE)

(73) Assignee: Janssen Pharmaceutica, N.V., Beerse (BE)

(*) Notice: Subject to any disclaimer, the term of this patent is extended or adjusted under 35 U.S.C. 154(b) by 0 days.

(21) Appl. No.: 11/247,392

(22) Filed: Oct. 11, 2005

(65) Prior Publication Data

US 2006/0058309 A1    Mar. 16, 2006

Related U.S. Application Data

(62) Division of application No. 10/019,376, filed as application No. PCT/EP00/05677 on Jun. 20, 2000, now Pat. No. 7,071,192.

(30) Foreign Application Priority Data

Jun. 28, 1999    (EP) .................................. 99202089

(51) Int. Cl.
| A61P 11/00 | (2006.01) |
| A61P 31/12 | (2006.01) |
| A61K 31/4709 | (2006.01) |
| A61K 31/4375 | (2006.01) |
| A61K 31/437 | (2006.01) |
| A61K 31/498 | (2006.01) |
| A61K 31/4409 | (2006.01) |
| A61K 31/436 | (2006.01) |
| C07D 471/04 | (2006.01) |
| C07D 417/14 | (2006.01) |
| C07D 413/14 | (2006.01) |
| C07D 409/14 | (2006.01) |
| C07D 401/06 | (2006.01) |
| C07D 491/056 | (2006.01) |

(52) U.S. Cl. ...................................... 514/303; 546/118
(58) Field of Classification Search .................. 514/303; 546/118
See application file for complete search history.

(56) References Cited

U.S. PATENT DOCUMENTS

| 4,634,704 A | 1/1987 | Janssens et al. ............. 514/253 |
| 4,695,569 A | 9/1987 | Janssens et al. ............. 514/258 |
| 5,567,824 A | 10/1996 | Chen et al. .................. 514/252 |

FOREIGN PATENT DOCUMENTS

| EP | 0 005 318 A1 | 11/1979 |
| EP | 0 099 139 A2 | 1/1984 |
| EP | 0 144 101 A2 | 6/1985 |
| EP | 0 145 037 A2 | 6/1985 |
| EP | 0 151 824 A2 | 8/1985 |
| EP | 0 151 826 A1 | 8/1985 |
| EP | 0 232 937 A2 | 8/1987 |
| EP | 0 295 742 A1 | 12/1988 |
| EP | 0 297 661 A1 | 1/1989 |

(Continued)

OTHER PUBLICATIONS

Akula, M. R. et al., "An Improved Synthesis of 3-Phenyl-and 3-Methoxyquinaldine," *Org. Prep. Proced. Int.*, 1991, 23, pp. 386-387.
Cerè, V. et al., "Catalytic Hydrogenation of Benzo[2.1.3]Oxadiazoles," *Tetrahedron*, 1972, 28, 3271-3276.
Chiba, T. et al., "Inhibitory Effect of Pyridobenzazoles on Virus Replication in vitro," *Biol Pharm Bull*, 1995, 18(8), 1081-1083.
Goodman and Gilman, "Biotransformation of Drugs," in *The Pharmacological Basis of Therapeutics*, 8th ed., McGraw-Hill, Int. Ed. 1992, 13-15.

(Continued)

*Primary Examiner*—Brenda L Coleman
(74) *Attorney, Agent, or Firm*—Woodcock Washburn LLP

(57) ABSTRACT

The present invention concerns compounds of formula (I), prodrugs, N-oxides, addition salts, quaternary amines, metal complexes and stereochemically isomeric forms thereof wherein $-a^1=a^2-a^3=a^4-$ represents a radical of formula $-CH=CH-CH=CH-$; $-N=CH-CH=CH-$; $-CH=N-CH=CH-$; $-CH=CH-N=CH-$; $CH=CH-CH=N-$; wherein each hydrogen atom may optionally be substituted; Q is a radical of formulae (b-1), (b-2), (b-3), (b-4), (b-5), (b-6), (b-7) and (b-8), wherein Alk is $C_{1-6}$alkanediyl; $Y^1$ is a bivalent radical of formula $-NR^2-$ or $-CH(NR^2R^4)$; $X^1$ is $NR^4$, S, S(=O), S(=O)$_2$, O, $CH_2$, C(=O), CH(=CH$_2$), CH(OH), CH(CH$_3$), CH(OCH$_3$), CH(SCH$_3$), CH(NR$^{5a}$R$^{5b}$), CH$_2$—NR$^4$ or NR$^4$—CH$_2$; $X^2$ is a direct bond, CH$_2$, C(=O), NR$^4$, $C_{1-4}$alkyl-NR$^4$, NR$^4$—C$_{1-4}$alkyl, t is 2 to 5; u is 1 to 5; v is 2 or 3; and whereby each hydrogen in Alk and in (b-3), (b-4), (b-5), (b-6), (b-7) and (b-8), may optionally be replaced by $R^3$; provided that when $R^3$ is hydroxy or $C_{1-6}$alkyloxy, then $R^3$ cannot replace a hydrogen atom in the α position relative to a nitrogen atom; G is a direct bond or optionally substituted $C_{1-10}$alkanediyl; $R^1$ is an optionally substituted bicyclic heterocycle; $R^2$ is hydrogen, formyl, $C_{1-6}$alkylcarbonyl, Hetcarbonyl, pyrrolidinyl, piperidinyl, homopiperidinyl, $C_{3-7}$cycloalkyl or $C_{1-10}$alkyl substituted with N(R$^6$)$_2$ and optionally with another substituent; $R^3$ is hydrogen, hydroxy, $C_{1-6}$alkyl, $C_{1-6}$alkyloxy, arylC$_{1-6}$alkyl or arylC$_{1-6}$alkyloxy, $R^4$ is hydrogen, $C_{1-6}$alkyl or arylC$_{1-6}$alkyl; $R^{5a}$, $R^{5b}$, $R^{5c}$ and $R^{5d}$ are hydrogen or $C_{1-6}$alkyl; or $R^{5a}$ and $R^{5b}$, or $R^{5c}$ and $R^{5d}$ taken together from a bivalent radical of formula $-(CH_2)_S-$ wherein S is 4 or 5; $R^6$ is hydrogen, $C_{1-4}$alkyl, formyl, hydroxyC$_{1-6}$alkyl, $C_{1-6}$alkylcarbonyl or C$_{1-6}$alkyloxycarbonyl; aryl is optionally substituted phenyl; Het is pyridyl, pyrimidinyl, pyrazinyl, pyridazinyl; as respiratory syncytial virus replication inhibitors; their preparation, compositions containing them and their use as a medicine.

12 Claims, No Drawings

FOREIGN PATENT DOCUMENTS

| | | |
|---|---|---|
| EP | 0 307 014 A1 | 3/1989 |
| EP | 0 433 898 A2 | 6/1991 |
| EP | 0 747 363 A1 | 12/1996 |
| WO | WO 92/01687 A1 | 2/1992 |
| WO | WO 92/01697 A1 | 2/1992 |
| WO | WO 98/10764 A1 | 3/1998 |
| WO | WO 98/31363 A1 | 7/1998 |
| WO | WO 98/55120 A1 | 12/1998 |
| WO | WO 99/44596 A1 | 9/1999 |
| WO | WO 00/04900 | 2/2000 |

OTHER PUBLICATIONS

Greene, T. et al., *Protective Groups in Organic Synthesis*, John Wiley & Sons Inc., 1991, Chapter 7.

Lindström, S. et al., "Synthesis of the Mutagenic 2-Amino-1,6-Dimethyl-Imidazo[4,5-*b*]Pyridine (1,6-DMIP) and Five of Its Isomers," *Heterocycles*, 1994, 38(3), 529-540.

Richardson, Jr. et al. "Study of the Synthesis and Chemistry of the 5,6-Dihydroimidazo[ij]quinoline Series," *J. Org. Chem.*, 1960, 25, 1138-1147.

Tidwell, R. et al., "Aromatic Amidines: Comparison of Their Ability to Block Respiratory Syncytial Virus Induced Cell Fusion and to Inhibit Plasmin, Urokinase, Thrombin, and Trypsin," *J Med Chem*, 1983, 26, 294-298.

Wyde et al., "CL387626 exhibits marked and unusual antiviral activity agaisnt respiratory syncytial virus in tissue cutlure and in cotton rats," *Antivirus Research*, 1998, 38, 31-42.

RESPIRATORY SYNCYTIAL VIRUS REPLICATION INHIBITORS

CROSS-REFERENCE TO RELATED APPLICATIONS

This application is a divisional application of U.S. application Ser. No. 10/019,376, filed Dec. 27, 2001, which is the national stage entry under 35 U.S.C. § 371 of PCT/EP00/05677 filed Jun. 20, 2000, which claims priority to EPO 99202089.1 filed Jun. 28, 1999, the disclosures of which are incorporated herein by reference in their entirety.

The present invention is concerned with benzimidazoles and imidazopyridines having antiviral activity, in particular, they have an inhibitory activity on the replication of the respiratory syncytial virus. It further concerns their preparation and compositions comprising them, as well as their use as a medicine.

Human RSV or Respiratory Syncytial Virus is a large RNA virus, member of the family of Paramyxoviridae, subfamily pneumovirinae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Reinfection with RSV is thus common, despite the existence of only two subtypes, A and B.

Today only three drugs have been approved for use against RSV infection. Ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

EP-A-0,005,318, EP-A-0,099,139, EP-A-0,145,037, EP-A-0,144,101, EP-A-0,151,826, EP-A-0,151,824, EP-A-0,232,937, EP-A-0,295,742, EP 0,297,661, EP-A-0,307,014, WO 92 01697 describe benzimidazole and imidazopyridine substituted piperidine and piperazine derivatives as antihistaminics, antiallergics or serotonine antagonists.

Thus, the present invention concerns the compounds of formula (I)

their prodrugs, N-oxides, addition salts, quaternary amines, metal complexes and stereochemically isomeric forms wherein -$a^1$=$a^2$-$a^3$=$a^4$- represents a bivalent radical of formula $$-CH=CH-CH=CH- \qquad (a-1);$$

$$-N=CH-CH=CH- \qquad (a-2);$$

$$-CH=N-CH=CH- \qquad (a-3);$$

$$-CH=CH-N=CH- \qquad (a-4); \text{ or}$$

$$-CH=CH-CH=N- \qquad (a-5);$$

wherein each hydrogen atom in the radicals (a-1), (a-2), (a-3), (a-4) and (a-5) may optionally be replaced by halo, $C_{1-6}$alkyl, nitro, amino, hydroxy, $C_{1-6}$alkyloxy, polyhalo$C_{1-6}$alkyl, carboxyl, amino$C_{1-6}$alkyl, mono- or di($C_{1-4}$alkyl)amino$C_{1-6}$alkyl, $C_{1-4}$alkyloxycarbonyl, hydroxy$C_{1-6}$alkyl, or a radical of formula wherein =Z is =O, =CH—C(=O)—NR$^{5a}$R$^{5b}$, =CH$_2$, =CH—C$_{1-6}$alkyl, =N—OH or =N—O—C$_{1-6}$alkyl;

Q is a radical of formula

-continued

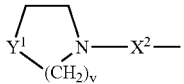 (b-6)

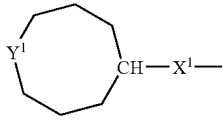 (b-7)

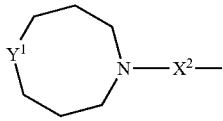 (b-8)

wherein Alk is $C_1$ alkanediyl;

$Y^1$ is a bivalent radical of formula $-NR^2-$ or $-CH(NR^2R^4)-$;

$X^1$ is $NR^4$, S, S(=O), S(=O)$_2$, O, CH$_2$, C(=O), C(=CH$_2$), CH(OH), CH(CH$_3$), CH(OCH$_3$), CH(SCH$_3$), CH(NR$^{5a}$R$^{5b}$), CH$_2$—NR$^4$ or NR$^4$—CH$_2$;

$X^2$ is a direct bond, CH$_2$, C(=O), NR$^4$, $C_{1-4}$alkyl-NR$^4$, NR$^4$—$C_{1-4}$alkyl;

t is 2, 3, 4 or 5;

u is 1, 2, 3, 4 or 5;

v is 2 or 3; and whereby each hydrogen atom in Alk and the carbocycles and the heterocycles defined in radicals (b-3), (b-4), (b-5), (b-6), (b-7) and (b-8) may optionally be replaced by $R^3$; with the proviso that when $R^3$ is hydroxy or $C_{1-6}$alkyloxy, then $R^3$ can not replace a hydrogen atom in the α position relative to a nitrogen atom;

G is a direct bond or $C_{1-10}$alkanediyl optionally substituted with one, two or three substituents selected from hydroxy, $C_{1-6}$alkyloxy, arylC$_{1-6}$alkyloxy, $C_{1-6}$alkylthio, arylC$_{1-6}$alkylthio, arylcarbonyl, HO(—CH$_2$—CH$_2$—O)$_n$—, $C_{1-6}$alkyloxy(—CH$_2$—CH$_2$—O)$_n$—, arylC$_{1-6}$alkyloxy(—CH$_2$—CH$_2$—O)$_n$—, amino, mono-or di(C$_{1-6}$alkyl)amino, $C_{1-6}$alkyloxycarbonylamino and aryl;

$R^1$ is a bicyclic heterocycle selected from quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl, 2,3-dihydro-1,4-dioxino[2,3-b]pyridyl or a radical of formula

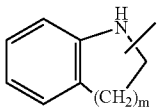 (c-1)

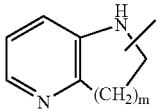 (c-2)

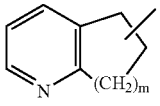 (c-3)

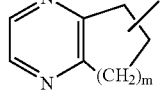 (c-4)

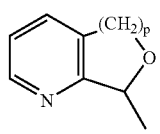 (c-5)

 (c-6)

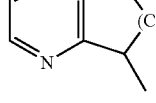 (c-7)

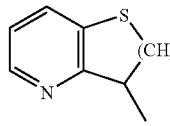 (c-8)

and said bicyclic heterocycles may optionally be substituted in either of the two cycles with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy-$C_{1-6}$alkyl, aryl, arylC$_{1-6}$alkyl, arylC$_{1-6}$alkyloxy, hydroxyC$_{1-6}$alkyl, mono-or di(C$_{1-6}$alkyl)-amino, mono-or di(C$_{1-6}$alkyl)aminoC$_{1-6}$alkyl, polyhaloC$_{1-6}$alkyl, $C_{1-6}$alkylcarbonylamino, $C_{1-6}$alkyl-SO$_2$—NR$^{5c}$—, aryl-SO$_2$—NR$^{5c}$—, $C_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, arylC$_{1-6}$alkyloxy(—CH$_2$—CH$_2$—O)$_n$— and mono-or di(C$_{1-6}$alkyl)amino(—CH$_2$—CH$_2$—O)$_n$—;

each n independently is 1, 2, 3 or 4;

each m independently is 1 or 2;

each p independently is 1 or 2;

each $R^2$ independently is hydrogen, formyl, $C_{1-6}$alkylcarbonyl, Hetcarbonyl, pyrrolidinyl, piperidinyl, homopiperidinyl, $C_{3-7}$cycloalkyl substituted with N(R$^6$)$_2$, or $C_{1-10}$alkyl substituted with N(R$^6$)$_2$ and optionally with a second, third or fourth substituent selected from amino, hydroxy, $C_{3-7}$cycloalkyl, $C_{2-5}$alkanediyl, piperidinyl, mono-or di(C$_{1-6}$alkyl)amino, $C_{1-6}$alkyloxycarbonylamino, aryl and aryloxy;

$R^3$ is hydrogen, hydroxy, $C_{1-6}$alkyl, $C_{1-6}$alkyloxy, arylC$_{1-6}$alkyl or arylC$_{1-6}$alkyloxy;

$R^4$ is hydrogen, $C_{1-6}$alkyl or arylC$_{1-6}$alkyl;

$R^{5a}$, $R^{5b}$, $R^{5c}$ and $R^{5d}$ each independently are hydrogen or $C_{1-6}$alkyl; or $R^{5a}$ and $R^{5b}$, or $R^{5c}$ and $R^{5d}$ taken together form a bivalent radical of formula —(CH$_2$)$_s$— wherein s is 4 or 5;

$R^6$ is hydrogen, $C_{1-4}$alkyl, formyl, hydroxyC$_{1-6}$alkyl, $C_{1-6}$alkylcarbonyl or $C_{1-6}$alkyloxycarbonyl;

aryl is phenyl or phenyl substituted with 1 or more, such as 2, 3 or 4, substituents selected from halo, hydroxy, $C_1$alkyl, hydroxyC$_{1-6}$alkyl, polyhaloC$_{1-6}$alkyl, and $C_{1-6}$alkyloxy;

Het is pyridyl, pyrimidinyl, pyrazinyl, pyridazinyl.

The term prodrug as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13-15) describing prodrugs generally, is hereby incorporated.

As used herein $C_{1-3}$alkyl as a group or part of a group defines straight or branched chain saturated hydrocarbon radicals having from 1 to 3 carbon atoms such as methyl, ethyl, propyl, 1-methylethyl and the like; $C_{1-4}$alkyl as a group or part of a group defines straight or branched chain saturated hydrocarbon radicals having from 1 to 4 carbon atoms such as the group defined for $C_{1-3}$alkyl and butyl and the like; $C_{2-4}$alkyl as a group or part of a group defines straight or branched chain saturated hydrocarbon radicals having from 2 to 4 carbon atoms such as ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-9}$alkyl as a group or part of a group defines straight or branched chain saturated hydrocarbon radicals having from 1 to 9 carbon atoms such as the groups defined for $C_{1-6}$alkyl and heptyl, octyl, nonyl, 2-methylhexyl, 2-methylheptyl and the like; $C_{1-10}$alkyl as a group or part of a group defines straight or branched chain saturated hydrocarbon radicals having from 1 to 10 carbon atoms such as the groups defined for $C_{1-9}$alkyl and decyl, 2-methylnonyl and the like. $C_{3-7}$cycloalkyl is generic to cyclopropyl, cyclobutyl, cyclopentyl, cyclohexyl and cycloheptyl; $C_{2-5}$alkanediyl defines bivalent straight and branched chain saturated hydrocarbon radicals having from 2 to 5 carbon atoms such as, for example, 1,2-ethanediyl, 1,3-propanediyl, 1,4-butanediyl, 1,2-propanediyl, 2,3-butanediyl, 1,5-pentanediyl and the like, $C_{2-5}$alkanediyl is substituted on $C_{1-10}$alkyl as provided for in the definition of $R^2$, it is meant to be substituted on one carbon atom thus forming a spiro moiety; $C_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; $C_{1-6}$alkanediyl is meant to include $C_{1-4}$alkanediyl and the higher homologues thereof having from 5 to 6 carbon atoms such as, for example, 1,5-pentanediyl, 1,6-hexanediyl and the like; $C_{1-10}$alkanediyl is meant to include $C_{1-6}$alkanediyl and the higher homologues thereof having from 7 to 10 carbon atoms such as, for example, 1,7-heptanediyl, 1,8-octanediyl, 1,9-nonanediyl, 1,10-decanediyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom. The term (=N—OH) forms a hydroxylimine moiety when attached to a carbon atom.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, in particular methyl with one or more fluoro atoms, for example, difluoromethyl or trifluoromethyl. In case more than one halogen atoms are attached to an alkyl group within the definition of polyhalo$C_{1-4}$alkyl, they may be the same or different.

As described hereinabove, $R^1$ defines a bicyclic heterocycle which may optionally be substituted. The substituents may be divided over both rings or they may be attached to one and the same ring.

When any variable (e.g. aryl, $R^2$, $R^3$, $R^4$, $R^{5a}$, $R^{5b}$ etc.) occurs more than one time in any constituent, each definition is independent.

It will be appreciated that some of the compounds of formula (I) and their prodrugs, N-oxides, addition salts, quaternary amines, metal complexes and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their prodrugs, N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their prodrugs, N-oxides, salts, solvates or quaternary amines substantially free, i.e. associated with less than 10%, preferably less than 5%, in particular less than 2% and most preferably less than 1% of the other isomers. Stereochemically isomeric forms of the compounds of formula (I) are obviously intended to be embraced within the scope of this invention. As used hereinafter the terms trans or cis are well-known by the person skilled in the art.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

A special group of corn pounds are those compounds of formula (I) wherein one or more of the following restrictions apply:

Q is a radical of formula (b-1), (b-3), (b-4), (b-5), (b-6), (b-7) or (b-8);

$X^2$ is a direct bond, $CH_2$ or $C(=O)$;

$R^1$ is a bicyclic heterocycle selected from quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl, or a radical of formula

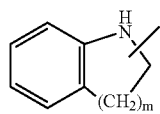
(c-1)

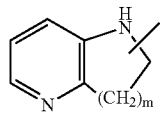
(c-2)

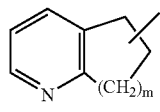
(c-3)

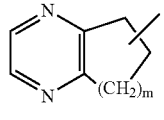
(c-4)

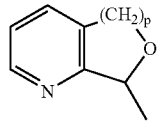
(c-5)

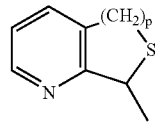
(c-6)

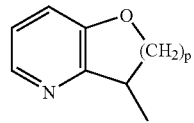
(c-7)

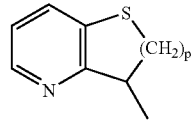
(c-8)

and said bicyclic heterocycles may optionally be substituted in either of the two cycles with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy-$C_{1-6}$alkyl, aryl, aryl$C_{1-6}$alkyl, aryl$C_{1-6}$alkyloxy, hydroxy$C_{1-6}$alkyl, mono-or di($C_{1-6}$alkyl)-amino, mono-or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{5c}$—, aryl-$SO'_2$—$NR^{5c}$—, $C_{1-6}$alkyloxycarbonyl, —C(=O)—$NR^{5c}R^{5d}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$— and mono-or di($C_{1-6}$alkyl)amino(—$CH_2$—$CH_2$—O)$_n$—;

each n independently is 1, 2, 3 or 4;

each m independently is 1 or 2;

each p independently is 1 or 2;

each $R^2$ independently is hydrogen, pyrrolidinyl, piperidinyl, homopiperidinyl, $C_{3-7}$cycloalkyl substituted with $NHR^6$, or $C_{1-10}$alkyl substituted with $NHR^6$ and optionally with a second, third or fourth substituent selected from amino, hydroxy, $C_{3-7}$cycloalkyl, $C_{2-5}$alkanediyl, piperidinyl, mono-or di($C_{1-6}$alkyl)amino, $C_{1-6}$alkyloxycarbonylamino, aryl and aryloxy;

$R^3$ is hydrogen, hydroxy, $C_{1-6}$alkyl, $C_{1-6}$alkyloxy or aryl$C_{1-6}$alkyl;

$R^6$ is hydrogen, $C_{1-4}$alkyl, formyl, $C_{1-6}$alkylcarbonyl or $C_{1-6}$alkyloxycarbonyl.

Another special group of compounds are those compounds wherein -$a^1$=$a^2$-$a^3$=$a^4$- is a radical of formula (a-1), (a-2) or (a-3).

Yet another special group of compounds are those compounds wherein Q is a radical of formula (b-5) wherein v is 2, and $Y^1$ is —$NR^2$—.

Also interesting compounds are those compounds wherein $R^2$ is $C_{1-10}$alkyl substituted with $NHR^6$.

Other interesting compounds are those compounds wherein G is a direct bond or $C_{1-10}$alkanediyl optionally substituted with one two or three substituents selected from hydroxy, $C_{1-6}$alkyloxy, aryl$C_{1-6}$alkyloxy, HO(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$—.

Preferred compounds are:

(±)-N-[1-(2-aminoethyl)-4-piperidinyl]-4-methyl-1-[1-(8-quinolinyl)ethyl]-1H-benzimidazol-2-amine monohydrate;

(±)-N-[1-(2-amino-3-methylbutyl)-4-piperidinyl]-1-(2-bromo-5,6,7,8-tetrahydro-8-quinolinyl)-1H-benzimidazol-2-amine trihydrochloride trihydrate;
(±)-N-[1-(2-amino-3-methylbutyl)-4-piperidinyl]-1-[(2-ethoxyethoxy)-8-quinolinyl-methyl]4-methyl-1H-benzimidazol-2-amine;
(±)-N-[1-(2-amino-3-methylbutyl)-4-piperidinyl]-1-(2-chloro-5,6,7,8-tetrahydro-5-quinoxalinyl)-1H-benzimidazol-2-amine trihydrochloride trihydrate;
(±)-N-[1-(2-amino-3-methylbutyl)-4-piperidinyl]-1-[(1-methyl-1H-benzimidazol-4-yl)methyl]-1H-benzimidazol-2-amine;
(±)-N-[1-(2-amino-3-methylbutyl)-4-piperidinyl]-1-(ethoxy-8-quinolinylmethyl)-1H-benzimidazol-2-amine;
(±)-N-[1-(2-amino-3-methylbutyl)-4-piperidinyl]4-methyl-1-(5,6,7,8-tetrahydro-5-quinoxalinyl)-1H-benzimidazol-2-amine;
(±)-N-[1-(2-aminoethyl)-4-piperidinyl]-7-methyl-3-(8-quinolinylmethyl)-3H-imidazo-[4,5-b]pyridin-2-amine tetrahydrochloride trihydrate;
(±)-N-[1-(2-amino-3-methylbutyl)-4-piperidinyl]-7-methyl-3-(8-quinolinylmethyl)-3H-imidazo[4,5-b]pyridin-2-amine tetrahydrochloride monohydrate;
(±)-N-[1-(2-amino-3-methylbutyl)-4-piperidinyl]-1-(8-quinolinylmethyl)-1H-imidazo[4,5-c]pyridin-2-amine trihydrochloride dihydrate;
N-[1-(2-aminoethyl)-4-piperidinyl])methyl-1-(8-quinolinylmethyl)-1H-benzimidazol-2-amine;
N-[1-(8-quinolinylmethyl)-1H-benzimidazol-2-yl]-1,3-propanediamine trihydrochloride monohydrate;
(±)-N-[1-(2-aminoethyl)-4-piperidinyl]-1-[(2-ethoxyethoxy)-8-quinolinylmethyl]-1H-benzimidazol-2-amine trihydrochloride dihydrate;
(±)-N-[1-(2-amino-3-methylbutyl)-4-piperidinyl]-1-(8-quinolinylmethyl)-1H-imidazo-[4,5-b]pyridine-2-amine trihydrochloride dihydrate;
(±)-N-[1-[1-(aminomethyl)-2-methylpropyl]4-piperidinyl]-1-[(2-ethoxyethoxy)-8-quinolinylmethyl]-1H-benzimidazol-2-amine;
(±)-N-[1-(2-aminoethyl)-4-piperidinyl]-3-(2-quinolinylmethyl)-3H-imidazo-[4,5-b]pyridin-2-amine trihydrochloride trihydrate;
(±)-N-[1-(2-amino-3-methylbutyl)-4-piperidinyl]-1-(1-isoquinolinylmethyl)-1H-benzimidazol-2-amine trihydrochloride;
N-[1-(2-aminoethyl)₄-piperidinyl]-1-(5,6,7,8-tetrahydro-5-quinoxalinyl)-1H-benzimidazol-2-amine trihydrochloride trihydrate;

the prodrugs, the N-oxides, the addition salts, the quaternary amines, the metal complexes and the stereochemically isomeric forms thereof.

Most preferred compounds are:
(±)-N-[1-(2-amino-3-methylbutyl)-4-piperidinyl]-3-(quinolinylmethyl)-3H-imidazo[4,5-b]pyridin-2-amine;
(±)-N-[1-(2-amino-3-methylbutyl)-4-piperidinyl]4-methyl-1-(8-quinolinylmethyl)-1H-benzimidazol-2-amine;
(±)-N-[1-(2-aminoethyl)-4-piperidinyl]-1-(2-chloro-5,6,7,8-tetrahydro-5-quinoxalinyl)-4-methyl-1H-benzimidazol-2-amine trihydrochloride trihydrate;
(±)-N-[1-(2-aminoethyl)-4-piperidinyl]-1-(5,6,7,8-tetrahydro-2,3-dimethyl-5-quinoxalinyl)-1H-benzimidazol-2-amine trihydrochloride trihydrate;
(±)-N-[1-(2-amino-3-methylbutyl)-4-piperidinyl]-1-[(2-ethoxyethoxy)-8-quinolinyl-methyl]-1H-benzimidazol-2-amine;
(±)-N-[1-(2-amino-3-methylbutyl)-4-piperidinyl-1-(3-chloro-5,6,7,8-tetrahydro-5-quinoxalinyl)-1H-benzimidazol-2-amine trihydrochloride monohydrate;
(±)-N-[1-(2-aminoethyl)-4-piperidinyl]-1-(3-chloro-5,6,7,8-tetrahydro-5-quinoxalinyl)-4-methyl-1H-benzimidazol-2-amine trihydrochloride dihydrate;
(±)-N-[1-(2-aminoethyl)-4-piperidinyl]-1-[(2-ethoxyethoxy)-8-quinolinylmethyl]-4-methyl-1H-benzimidazol-2-amine monohydrate;
(±)-N-[1-(2-amino-3-methylbutyl)-4-piperidinyl]-3-(8-quinolinylmethyl)-3H-imidazo-[4,5-c]pyridin-2-amine trihydrochloride tetrahydrate;
(±)-N-[1-(2-aminoethyl)-4-piperidinyl]-3-(8-quinolinylmethyl)-3H-imidazo[4,5-b]-pyridin-2-amine;
(±)-N-[1-(2-amino-3-methylbutyl)-4-piperidinyl]4-methyl-1-[(1-methyl-1H-benzimidazol-4-yl)methyl]-1H-benzimidazol-2-amine;
(±)-N-[1-(2-amino-3-methylbutyl)-4-piperidinyl]-1-(2-chloro-5,6,7,8-tetrahydro-5-quinoxalinyl)₄-methyl-1H-benzimidazol-2-amine;

the prodrugs, the N-oxides, the addition salts, the quaternary amines, the metal complexes and the stereochemically isomeric forms thereof.

In general, compounds of formula (I) can be prepared by reacting an intermediate of formula (II-a) or (II-b), wherein P represents a protecting group, such as, for example $C_{1-4}$alkyloxycarbonyl, or those protecting groups mentioned in Chapter 7 of 'Protective Groups in Organic Synthesis' by T Greene and P. Wuyts (John Wiley & Sons Inc., 1991), with an intermediate of formula (III), wherein $W_1$ is a suitable leaving group, such as a halo atom, e.g. chloro, bromo, in the presence of a suitable base, such as, e.g. sodium hydride. Said reaction can be performed in a reaction-inert solvent, such as N,N-dimethylformamide.

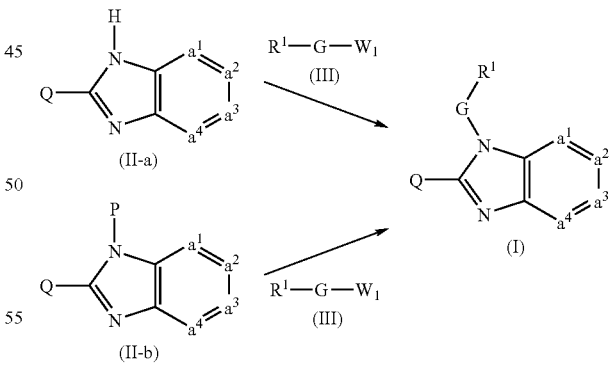

Compounds of formula (I) wherein, in the definition of Q, $R^2$ or at least one $R^6$ substituent is hydrogen, said Q being represented by H-Q₁, and said compounds being represented by formula (I-a), can be prepared by deprotecting an intermediate of formula (IV) wherein P represents a protecting group, for example $C_{1-4}$alkyloxycarbonyl, benzyl, or those protecting groups mentioned in Chapter 7 of 'Protective Groups in Organic Synthesis' by T Greene and P. Wuyts (John Wiley & Sons Inc., 1991).

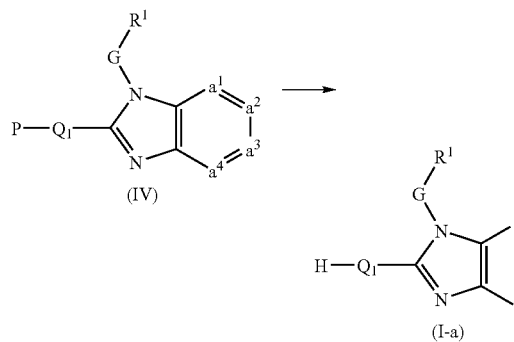

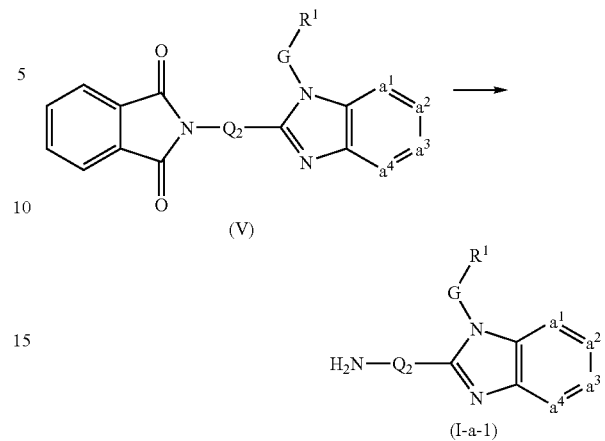

When P represents, for example, $C_{1-4}$alkyloxycarbonyl, said deprotection reaction can be performed by, for example, acidic hydrolysis in the presence of a suitable acid, such as hydrobromic, hydrochloric, sulfuric, acetic, or trifluoroacetic acid or a mixture of said acids, or by alkaline hydrolysis in the presence of a suitable base, such as, for example potassium hydroxide, in a suitable solvent such as water, alcohol, a mixture of water-alcohol, methylene chloride. Suitable alcohols are methanol, ethanol, 2-propanol, 1-butanol and the like. In order to enhance the rate of the reaction, it is advantageous to heat the reaction mixture, in particular up to the reflux temperature. Alternatively, when P represents, for example, benzyl, the deprotection reaction can be performed by catalytic hydrogenation in the presence of hydrogen and an appropriate catalyst in a reaction-inert solvent. A suitable catalyst in the above reaction is, for example, platinum-on-charcoal, palladium-on-charcoal, and the like. An appropriate reaction-inert solvent for said reaction is, for example, an alcohol, e.g. methanol, ethanol, 2-propanol and the like, an ester, e.g. ethylacetate and the like, an acid, e.g. acetic acid and the like.

The catalytic hydrogenation reaction described above can also be used to prepare a compound of formula (I-a) by deprotecting and reducing an intermediate of formula (IV) wherein $Q_1$ comprises an unsaturated bond, said $Q_1$ being represented by $Q_{1a}$(CH=CH), and said intermediate being represented by formula (IV-a).

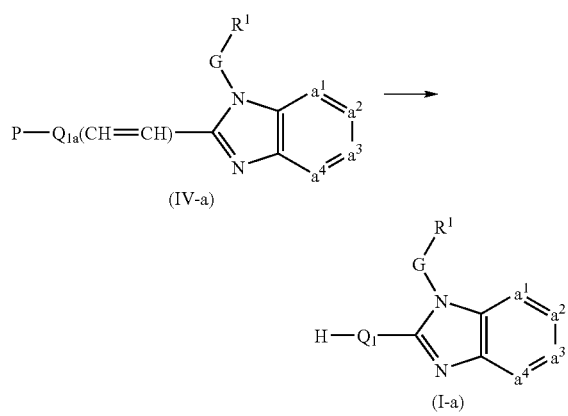

Compounds of formula (I) wherein, in the definition of Q, both $R^6$ substituents are hydrogen or $R^2$ and $R^4$ are both hydrogen, said Q being represented by $H_2N$-$Q_2$, and said compounds being represented by formula (I-a-1), can also be prepared by deprotecting an intermediate of formula (V).

Said deprotection reaction can be performed in the presence of a suitable base such as, for example hydrazine, or in the presence of a suitable acid, such as hydrochloric acid and the like, in a suitable solvent, such as an alcohol, acetic acid and the like.

Compounds of formula (I-a-1) can also be prepared by deprotecting an intermediate of formula (VI) according to the procedure described for the preparation of compounds of formula (I-a).

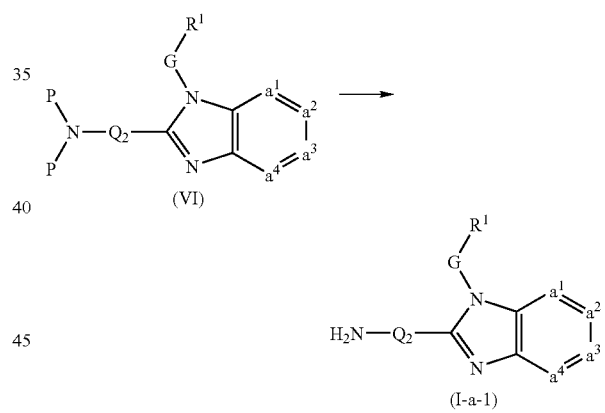

Compounds of formula (I-a) or (I-a-1), wherein $Q_1$ or $Q_2$ comprise a hydroxy substituent, said $Q_1$ or $Q_2$ being represented by $Q_{1'}$(OH) or $Q_{2'}$(OH), and said compounds being represented by formula (I-a-2) or (I-a-1-1), can be prepared by deprotecting an intermediate of formula (VII) or (VIII) as described hereinabove for the preparation of compounds of formula (I-a).

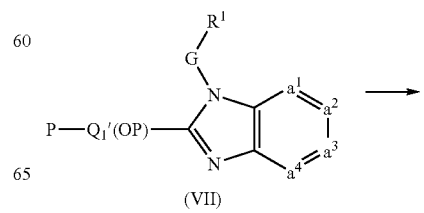

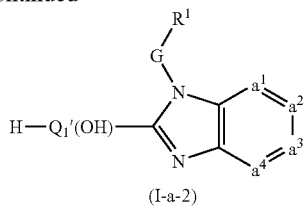

(I-a-2)

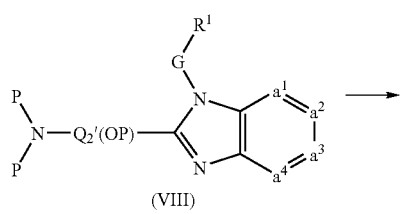

(VIII)

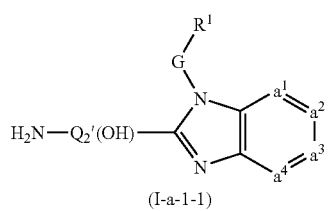

(I-a-1-1)

Compounds of formula (I) wherein, in the definition of Q, both $R^6$ substituents are hydrogen or $R^2$ and $R^4$ are both hydrogen, and the carbon adjacent to the nitrogen carrying the $R^6$, or $R^2$ and $R^4$ substituents contains at least one hydrogen, said Q being represented by $H_2N-Q_3H$, and said compounds being represented by formula (I-a-1-2) can also be obtained by reductive amination of intermediates of formula (IX) in the presence of a suitable amination reagent, such as, for example, ammonia, hydroxylamine, or benzylamine, and in the presence of a suitable reducing agent, e.g. hydrogen, and an appropriate catalyst. An appropriate catalyst in the above reaction is, for example, platinum-on-charcoal, palladium-on-charcoal, rhodium-on-$Al_2O_3$, and the like, optionally in the presence of a catalyst poison, such as a thiophene solution. A suitable reaction-inert solvent for the above reaction is, for example, an alcohol, e.g. methanol, ethanol, 2-propanol and the like.

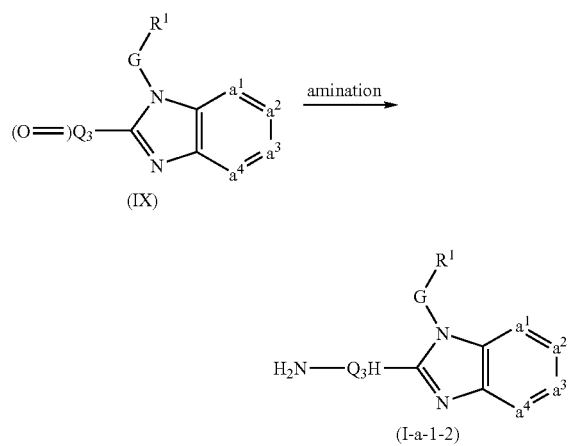

Compounds of formula (I), wherein Q comprises a —$CH_2NH_2$ moiety, said Q being represented by $H_2N-CH_2-Q_4$, and said compounds being represented by formula (I-a-1-3) can be prepared by reducing an intermediate of formula (X).

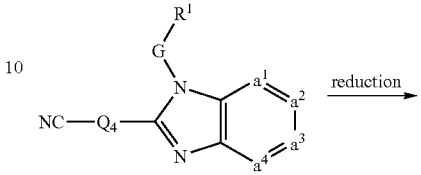

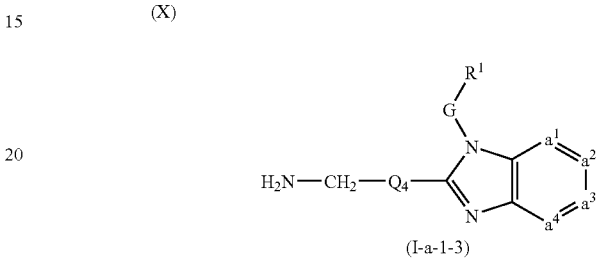

Said reduction can be performed with a suitable reducing agent, such as lithium aluminium hydride or hydrogen, optionally in the presence of a suitable catalyst, such as Raney Nickel. A suitable solvent for the above reaction is, for example, tetrahydrofuran, or a solution of ammonia in an alcohol. Suitable alcohols are methanol, ethanol, 2-propanol and the like. Said reduction reaction performed in a solution of ammonia in an alcohol can also be used to prepare compounds of formula (I-a-1-3), wherein $R^1$ is substituted with $C_{1-6}$alkyloxy$C_{1-6}$alkyl, said $R^1$ being represented by $R^{1'}$—$C_{1-6}$alkyloxy$C_{1-6}$alkyl, and said compounds being represented by formula (I-a-1-3-1) starting from an intermediate of formula (X-a).

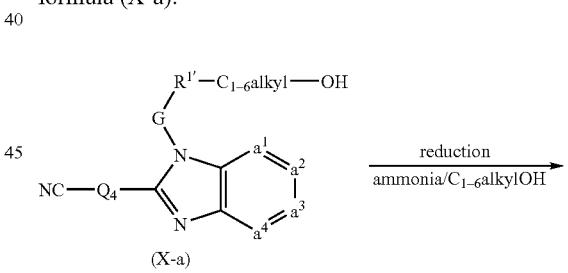

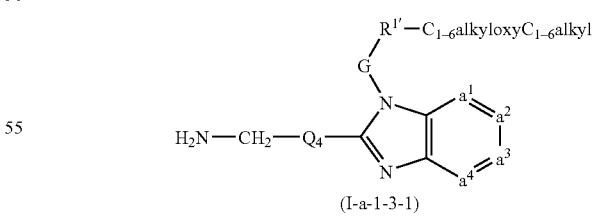

Compounds of formula (I), wherein Q comprises a —$CH_2$—CHOH—$CH_2$—$NH_2$ moiety, said Q being represented by $H_2N$—$CH_2$—CHOH—$CH_2$-$Q_{4'}$, and said compounds being represented by formula (I-a-1-3-2), can be prepared by reacting an intermediate of formula (XI) with ammonia in the presence of a suitable reaction-inert solvent, such as an alcohol, e.g. methanol.

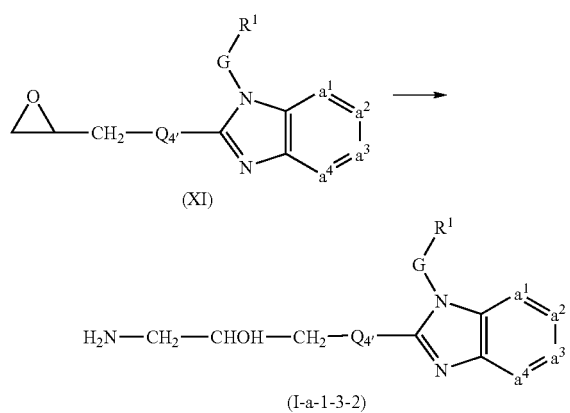

(XI)

(I-a-1-3-2)

Compounds of formula (I), wherein, in the definition of Q, $R^2$ or one $R^6$ substituent is formyl, said Q being represented by $H—C(=O)-Q_1$, and said compounds being represented by formula (I-b), can be prepared by reacting an intermediate of formula (XII) with formic acid, formamide and ammonia.

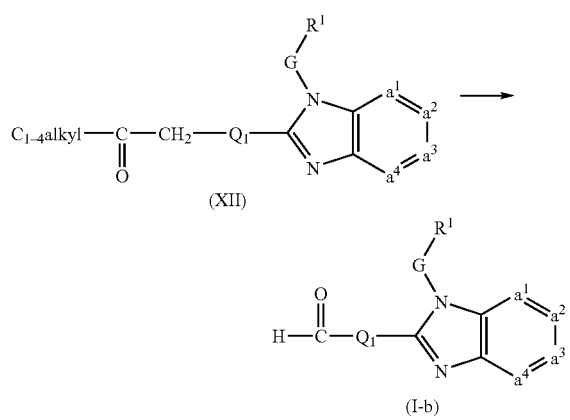

(XII)

(I-b)

Compounds of formula (I), wherein, in the definition of Q, $R^2$ is other than hydrogen, said $R^2$ being represented by $R^{2a}$, $R^4$ is hydrogen, and the carbon atom adjacent to the nitrogen atom carrying the $R^2$ and $R^4$ substituents, carries also at least one hydrogen atom, said Q being represented by $R^{2a}$—NH—$HQ_5$, and said compounds being represented by formula (I-c), can be prepared by reductive amination of an intermediate of formula (XIII) with an intermediate of formula (XIV) in the presence of a suitable reducing agent, such as hydrogen, and a suitable catalyst, such as palladium-on-charcoal, platinum-on-charcoal, and the like. A suitable reaction-inert solvent for the above reaction is, for example, an alcohol, e.g. methanol, ethanol, 2-propanol and the like.

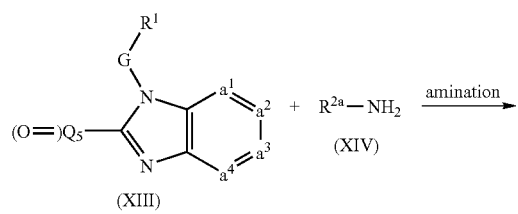

(XIII) (XIV)

-continued

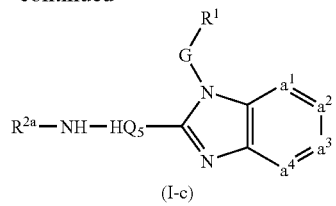

(I-c)

Compounds of formula (I-c), wherein $R^{2a}$ represents $C_{1-10}$alkyl substituted with $N(R^6)_2$ and with hydroxy, and the carbon atom carrying the hydroxy, carries also two hydrogen atoms, said $R^{2a}$ being represented by $[(C_{1-9}alkyl)CH_2OH]$—$N(R^6)_2$, and said compounds being represented by formula (I-c-1), can be prepared by reducing an intermediate of formula (XV) in the presence of a suitable reducing agent, such as lithium aluminium hydride, in a suitable reaction-inert solvent, such as tetrahydrofuran.

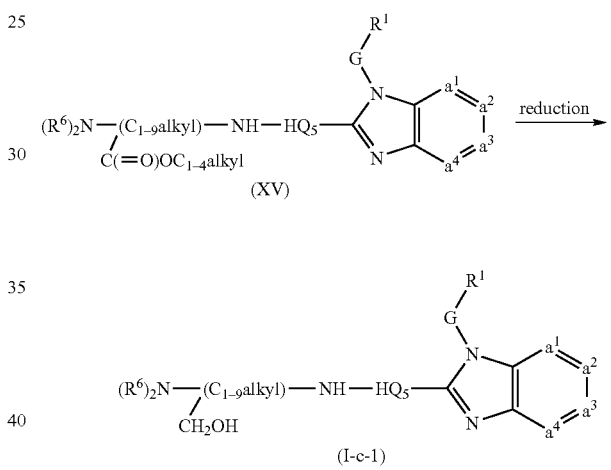

(XV)

(I-c-1)

Compounds of formula (I) wherein, in the definition of Q, $R^2$ or one $R^6$ substituent is hydrogen, said Q being represented by H-$Q_1$, and wherein $R^1$ is a bicyclic heterocycle substituted with 1 or more substituents selected from hydroxy, hydroxy$C_{1-6}$alkyl, or HO(—CH$_2$—CH$_2$—O)$_n$—, said substituents being represented by formula A-OH, said $R^1$ being represented by $R^{1a}$-(A-OH)$_w$, with w being the amount of substituents on $R^{1a}$ ranging from 1 to 4, and said compounds being represented by formula (I-d), can be prepared by deprotecting an intermediate of formula (XVI) with a suitable acid, such as hydrochloric acid and the like, optionally in the presence of a suitable solvent, such as an alcohol. Suitable alcohols are methanol, ethanol, 2-propanol and the like. Alternatively, one protecting group may also protect more than one substituent of $R^{1a}$, said protecting group being represented by $P_1$, as represented by formula (XVI-a). The two ways of protecting the substituents of $R^{1a}$, i.e. with a separate, as in formula (XVI), or a combined, as in formula (XVI-a), protecting group, may also be combined in the same intermediate, as represented by formula (XVI-b).

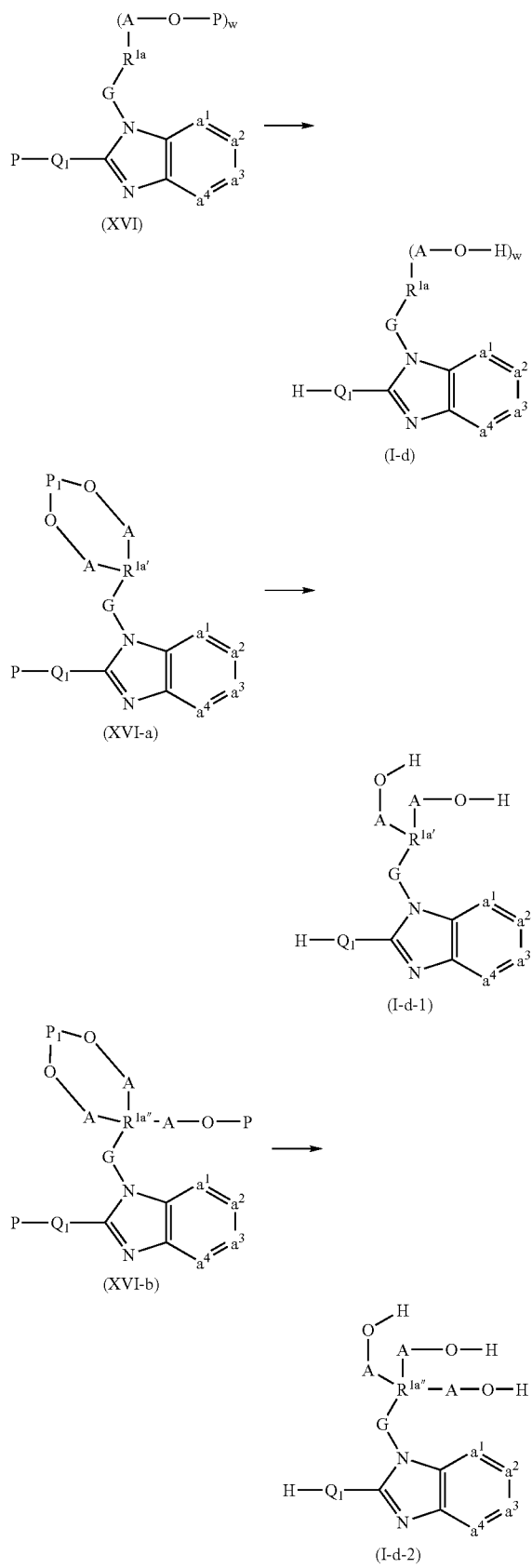

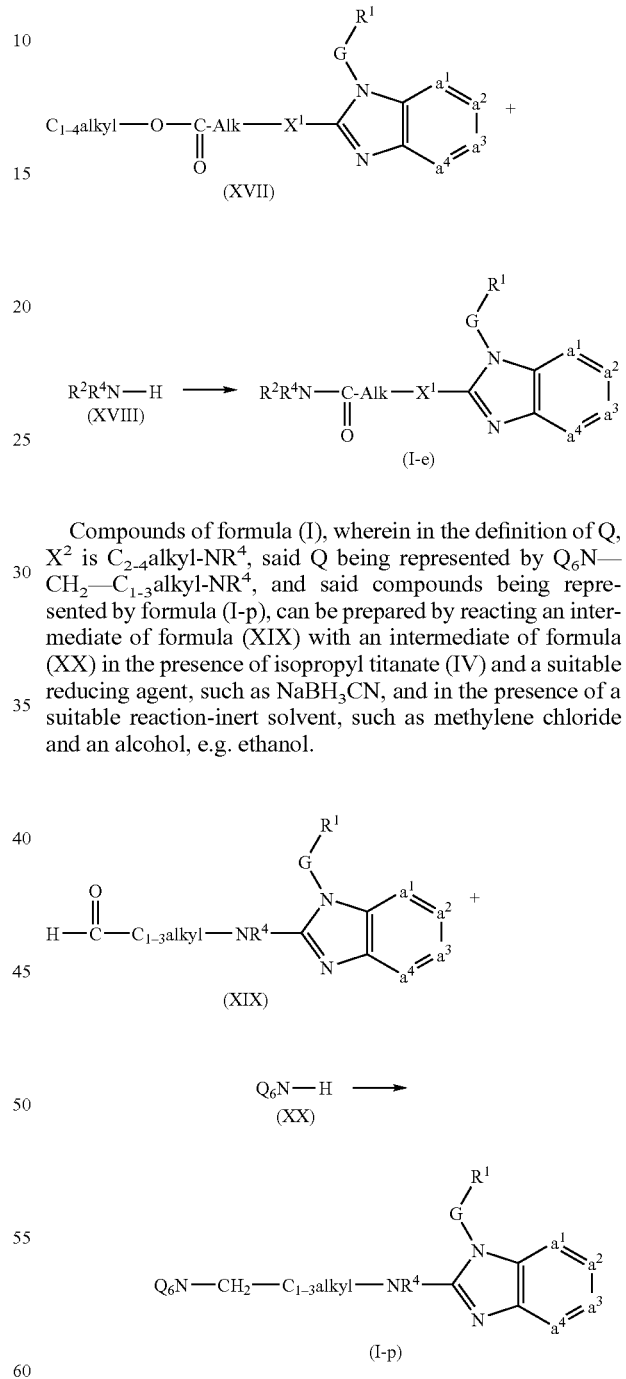

Compounds of formula (I), wherein Q is a radical of formula (b-2), said compounds being represented by formula (I-e), can be prepared by reacting an intermediate of formula (XVII) with an intermediate of formula (XVIII) in the presence of sodium cyanide and a suitable reaction-inert solvent, such as an alcohol, e.g. methanol and the like.

Compounds of formula (I), wherein in the definition of Q, $X^2$ is $C_{2-4}$alkyl-$NR^4$, said Q being represented by $Q_6N$—$CH_2$—$C_{1-3}$alkyl-$NR^4$, and said compounds being represented by formula (I-p), can be prepared by reacting an intermediate of formula (XIX) with an intermediate of formula (XX) in the presence of isopropyl titanate (IV) and a suitable reducing agent, such as $NaBH_3CN$, and in the presence of a suitable reaction-inert solvent, such as methylene chloride and an alcohol, e.g. ethanol.

Compounds of formula (I-p), wherein $R^2$ is $C_{1-6}$alkylcarbonyl, and Q is a radical of formula (b-6), wherein $Y^1$ is $NR^2$, said compounds being represented by formula (I-p-1), can be prepared by reacting an intermediate of formula (XIX) with an intermediate of formula (XX-a) according to the procedure described for the preparation of a compound of formula (I-p).

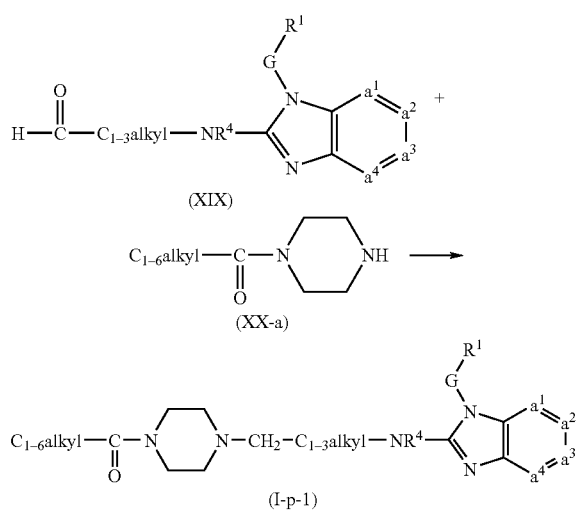

Compounds of formula (I), wherein G is substituted with hydroxy or HO(—CH$_2$CH$_2$O)$_n$—, said G being represented by G$_1$-OH, and said compounds being represented by formula (I-q), may be prepared by deprotecting an intermediate of formula (XXI), wherein P represents a suitable protecting group, for example, benzyl. Said deprotection reaction can be performed by catalytic hydrogenation in the presence of hydrogen and an appropriate catalyst in a reaction-inert solvent. A suitable catalyst in the above reaction is, for example, platinum-on-charcoal, palladium-on-charcoal, and the like. An appropriate reaction-inert solvent for said reaction is, for example, an alcohol, e.g. methanol, ethanol, 2-propanol and the like, an ester, e.g. ethylacetate and the like, an acid, e.g. acetic acid and the like.

Said reduction reaction can be performed in the presence of a suitable reducing agent, such as, for example sodium borohydride, in a reaction-inert solvent, such as an alcohol or tetrahydrofuran or a mixture thereof. Suitable alcohols are methanol, ethanol, 2-propanol and the like.

Compounds of formula (I) may be converted into each other following art-known functional group transformation reactions, comprising those described hereinafter.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise; for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I), wherein R$^1$ is a bicyclic heterocycle substituted with C$_{1-6}$alkyloxycarbonyl, said R$^1$ being represented by R$^{1'}$—C(=O)OC$_{1-6}$alkyl, and said compounds being represented by formula (I-f), can be prepared by esterification of a compound of formula (I-g) in the presence of a suitable alcohol, e.g. methanol, ethanol, propanol, butanol, pentanol, hexanol and the like, and in the presence of a suitable acid, such as hydrochloric acid and the like.

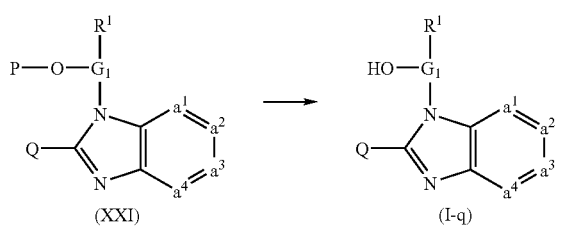

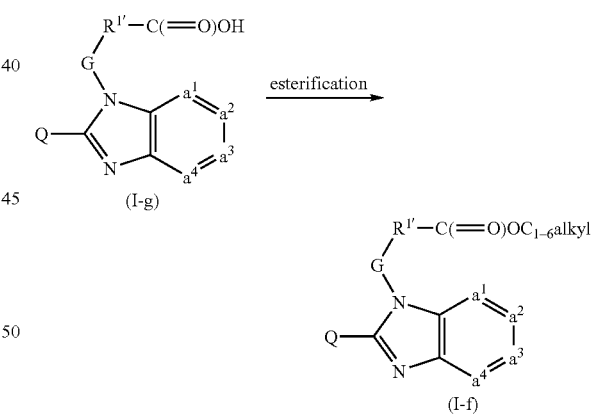

Compounds of formula (I), wherein G is substituted with hydroxy and the carbon atom carrying the hydroxy substituent carries also at least one hydrogen, said G being represented by H-G$_2$-OH, and said compounds being represented by formula (I-q-1), can also be prepared by reducing an intermediate of formula (XXII).

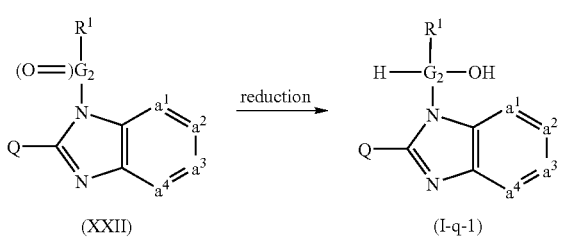

Compounds of formula (I-a) may be converted into compounds of formula (I) wherein, in the definition of Q, R$^2$ or at least one R$^6$ substituent is other than hydrogen, said R$^2$ or R$^6$ being represented by Z$_1$, said Q being represented by Z$_1$-Q$_1$, and said compounds being represented by formula (I-h), by reaction with a reagent of formula (XXIII), wherein W$_2$ is a suitable leaving group, such as a halo atom, e.g. bromo, or 4-methylbenzenesulphonate, in the presence of a suitable base, such as, for example disodium carbonate, dipotassium carbonate, sodium hydroxide and the like, in a reaction-inert solvent, e.g. 3-methyl-2-butanone, acetonitrile, N,N-dimethylformamide.

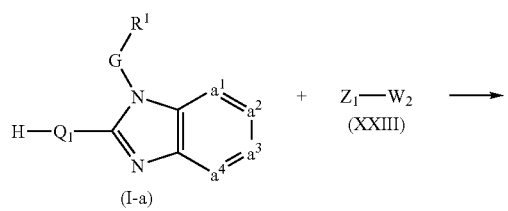

(I-a)    +    $Z_1$—$W_2$
              (XXIII)

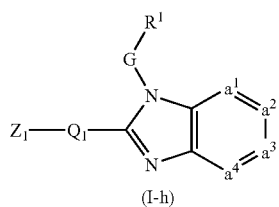

(I-h)

Compounds of formula (I-h), wherein, in the definition of $Z_1$, $R^2$ is $CH_2$—$C_{1-9}$alkyl substituted with $N(R^6)_2$, said compounds being represented by formula (I-h-1), can also be prepared by reacting a compound of formula (I-a) wherein, in the definition of H-$Q^1$, $R^2$ is hydrogen, said H-$Q_1$, being represented by H-$Q_{1b}$, and said compounds being represented by formula (I-a-3), with an intermediate of formula (XXIV), in the presence of a suitable reducing agent, such as sodium cyanoborohydride, in a suitable reaction-inert solvent, such as an alcohol.

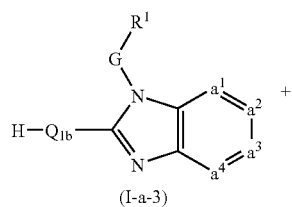

(I-a-3)

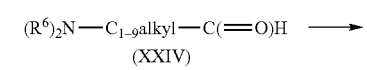

(XXIV)

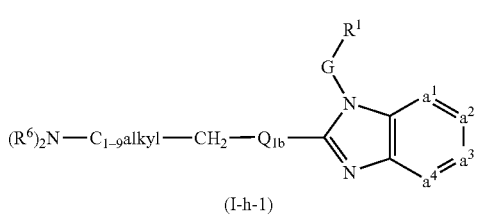

(I-h-1)

Compounds of formula (I-h), wherein $Z_1$ comprises formyl, $C_{1-6}$alkylcarbonyl, Hetcarbonyl or $C_{1-6}$alkyloxycarbonyl, said $Z_1$ being represented by $Z_{1a}$, and said compounds being represented by formula (I-h-2), can be converted into compounds of formula (I-a), by acidic hydrolysis in the presence of a suitable acid, such as hydrobromic, hydrochloric, sulfuric, acetic, or trifluoroacetic acid or a mixture of said acids, or by alkaline hydrolysis in the presence of a suitable base, such as, for example potassium hydroxide, in a suitable solvent such as water, alcohol, a mixture of water-alcohol, methylene chloride. Suitable alcohols are methanol, ethanol, 2-propanol, 1-butanol, sec. butanol and the like. In order to enhance the rate of the reaction, it is advantageous to work at elevated temperatures.

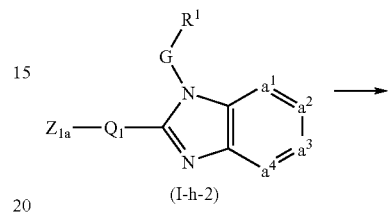

(I-h-2)

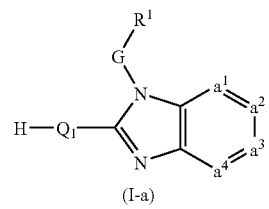

(I-a)

Compounds of formula (I-b) can be prepared by reacting a compound of formula (I-a) with formic acid.

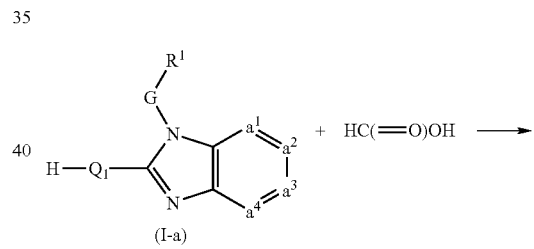

(I-a)

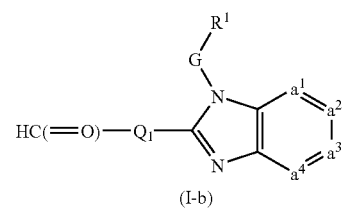

(I-b)

Compounds of formula (I) wherein $R^1$ is a bicyclic heterocycle substituted with hydroxy, said $R^1$ being represented by HO—$R^{1'}$, and said compounds being represented by formula (I-i), can be prepared by deprotecting a compound of formula (I-j), wherein $R^1$ is a bicyclic heterocycle substituted with $C_{1-6}$alkyloxy or aryl$C_{1-6}$alkyloxy, said $C_{1-6}$alkyl or aryl$C_{1-6}$alkyl being represented by $Z_2$ and said $R^1$ being represented by $Z_2$-O—$R^{1'}$. Said deprotection can be performed in a reaction-inert solvent, such as, for example methylene chloride, in the presence of a suitable deprotecting agent, e.g. tribromoborane.

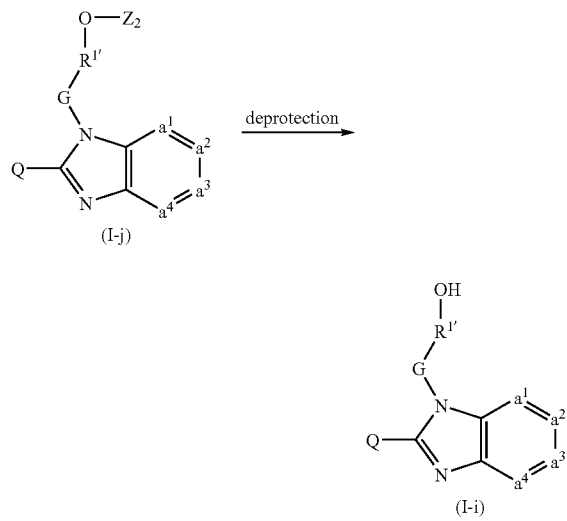

(I-j)

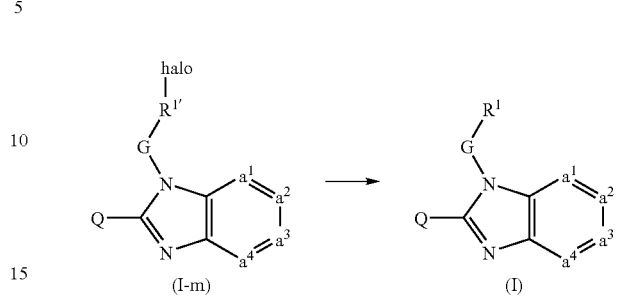

sented by formula (I-m) can be converted into compounds of formula (I) by reaction with 1-butanethiol in the presence of palladium-on-charcoal and CaO in a suitable reaction-inert solvent, such as tetrahydrofuran.

Compounds of formula (I) wherein R¹ is a bicyclic heterocycle substituted with halo(—CH₂—CH₂—O)ₙ, said compounds being represented by formula (I-k), can be converted into compounds of formula (I-l-1) or (I-l-2) by reaction with an appropriate amine of formula (XXV) or (XXVI) in a suitable reaction-inert solvent, e.g. tetrahydrofuran.

Compounds of formula (I) wherein a hydrogen atom in the radicals of formula (a-1), (a-2), (a-3), (a-4) or (a-5) is replaced by nitro, said compounds being represented by formula (I-n) may be reduced to a compound of formula (I-o) in the presence of a suitable reducing agent, such as hydrogen, optionally in the presence of a suitable catalyst, such as platinum-on-charcoal, and optionally in the presence of a suitable catalyst poison, e.g. a thiophene solution. The reaction may be performed in a suitable reaction-inert solvent, such as an alcohol.

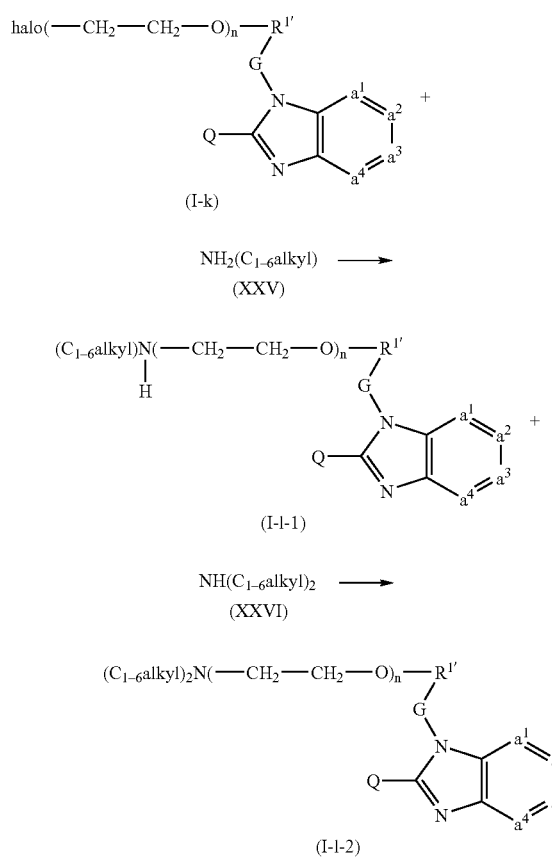

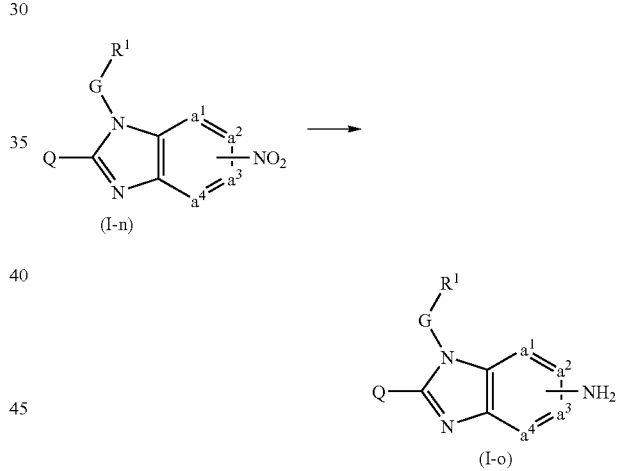

In the following paragraphs, there are described several methods of preparing the intermediates in the foregoing preparations. A number of intermediates and starting materials are commercially available or are known compounds which may be prepared according to conventional reaction procedures generally known in the art or analogous to the procedures described in EP-A-0005318, EP-A-0099139, EP-A-0151824, EP-A-0151826, EP-A-0232937, EP-A-0295742, EP-A-0297661, EP-A-0539420, EP-A-0539421, U.S. Pat. No. 4,634,704, U.S. Pat. No. 4,695,569.

In the foregoing and the following preparations, the reaction mixture is worked up following art-known methods and the reaction product is isolated and, if necessary, further purified.

Compounds of formula (I) wherein R¹ is a bicyclic heterocycle substituted with halo, said compounds being repre- Intermediates of formula (III) can be prepared by reacting an intermediate of formula (XXVII) with a suitable leaving group, i.e. W₁, introducing agent, e.g. 1-halo-2,5-pyrrolidinedione in the presence of dibenzoyl peroxide, in a reaction-inert solvent, e.g. tetrachloromethane.

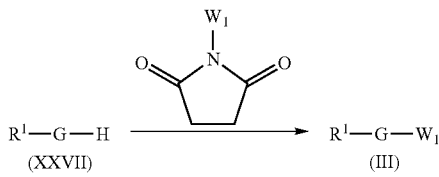

Intermediates of formula (XXVI), wherein $R^1$ is a bicyclic heterocycle substituted with chloro, said $R^1$ being represented by Cl—$R^{1'}$ and said intermediates being represented by formula (XXVII-a) can be prepared by reacting an intermediate of formula (XXVIII), wherein (O=)$R^{1b}$H is defined as a carbonyl derivative of $R^{1'}$ wherein one carbon or nitrogen, adjacent to the carbonyl, carries at least one hydrogen, with phosphorus oxychloride. Intermediates of formula (XXVIII) may also react as their enol tautomeric forms.

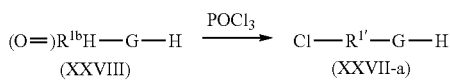

Intermediates of formula (XXVII), wherein $R^1$ is 2-trifluoromethyl-3-methyl (3H)-imidazo[4,5-b]pyridine, and G is $CH_2$, said intermediates being represented by formula (XXVII-b), can be prepared by reacting N-2,6-dimethyl-2,3-pyridinediamine (Heterocycles, 38, p 529, 1994), with trifluoroacetic acid.

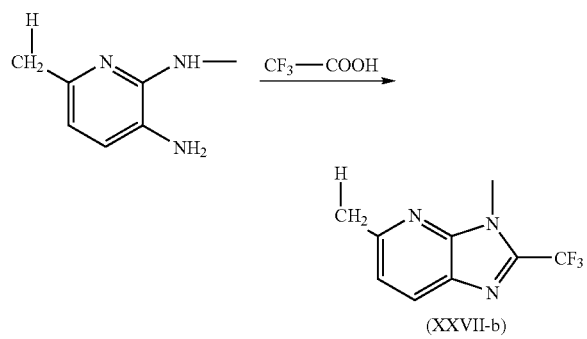

Intermediates of formula (III) wherein $W_1$ is chloro, which is attached to a carbon atom carrying at least one hydrogen, said G being represented by $G_3H$, and said intermediates being represented by formula (III-a) can also be prepared by reacting an intermediate of formula (XXIX) with thionylchloride in a reaction-inert solvent, e.g. methylenechloride.

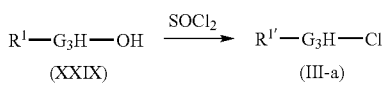

Intermediates of formula (XXIX) can be prepared by reducing an intermediate of formula (XXX) in a reaction-inert solvent, e.g. an alcohol, in the presence of a suitable reducing agent, e.g. sodium borohydride.

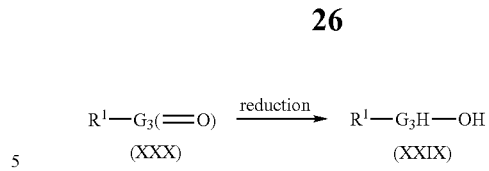

Alternatively, intermediates of formula (XXIX) can also be prepared by deprotecting an intermediate of formula (XXXI), wherein P is a suitable protecting group, e.g. $C_{1-4}$alkylcarbonyl, in a reaction-inert solvent, such as an alcohol, in the presence of a suitable base, e.g. sodium hydroxide.

Intermediates of formula (XXX), wherein $G_3$(=O) is CH(=O), said intermediates being represented by formula (XXX-a), can be prepared by reacting an intermediate of formula (XXXII), wherein $W_3$ is a suitable leaving group, such as a halo atom, e.g. bromo, with N,N-dimethylformamide in the presence of butyllithium in a reaction-inert solvent, e.g. tetrahydrofuran, diethylether or a mixture thereof.

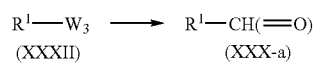

Intermediates of formula (XXX-a) can also be prepared by oxidizing an intermediate of formula $R^1$—$CH_2$—OH in the presence of a suitable oxidizing agent, e.g. $MnO_2$ in a reaction-inert solvent, e.g. methylenechloride.

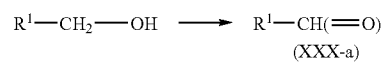

Intermediates of formula $R^1$—$CH_2$—OH, wherein $R^1$ is 2,3-dimethylquinoxaline, said intermediates being represented by formula (XCI) can be prepared by reducing an intermediate of formula (XCII) in a reaction-inert solvent, e.g. tetrahydrofuran, in the presence of a suitable reducing agent, e.g. potassium borohydride in the presence of lithium chloride.

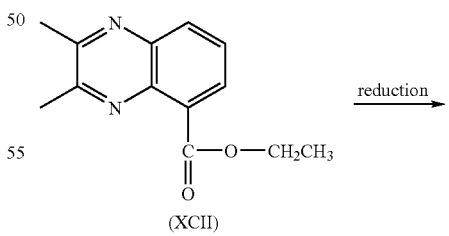

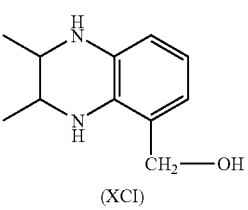

Intermediates of formula (XCII) can be prepared by reacting ethyl 2,3-diaminobenzoate (Tetrahydron, 28, 3271, 1972) with 2,3-butanedione in the presence of disodium disulfite.

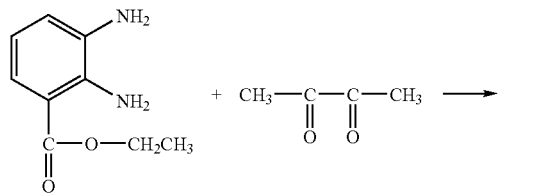

Intermediates of formula (XXXI), wherein $R^1$ is 5,6,7,8-tetrahydroquinoline, which can optionally be substituted, $G_3H$ is $CH_2$, and P is $C_{1-4}$alkylcarbonyl, said intermediates being represented by formula (XXXI-a) can be prepared by reacting an intermediate of formula (XCIII) with $C_{1-4}$alkylacid anhydride at elevated temperatures in the presence of a suitable base, e.g. sodium hydroxide.

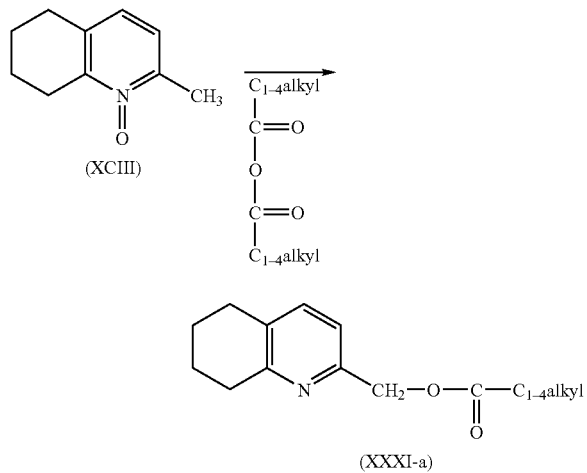

Intermediates of formula (XCIII) can be prepared by oxidizing an intermediate of formula (XCIV) with a suitable oxidizing agent, e.g. a peroxide such as 3-chloro-benzenecarboperoxoic acid, in a reaction-inert solvent, e.g. methylene chloride.

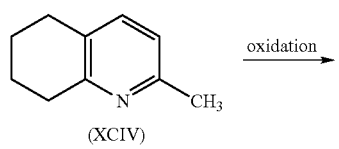

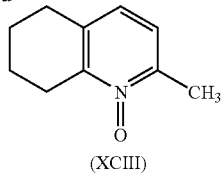

Intermediates of formula (XCIV) can be prepared by reducing an intermediate of formula (XCV) (Org. Prep. Proced. Int., 23, p 386-387, 1991) with an appropriate reducing agent, e.g. hydrogen, in the presence of a suitable catalyst, e.g. palladium-on-charcoal, and a suitable acid, e.g. trifluoroacetic acid.

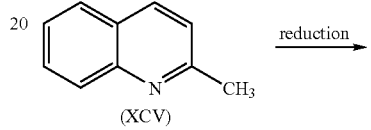

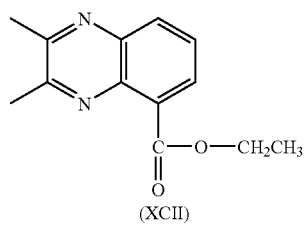

Intermediates of formula (IV) can be prepared by reacting an intermediate of formula (XXXIII-a) or (XXXIII-b), wherein P represents a suitable protecting group, such as, for example, $C_{1-4}$alkyloxycarbonyl, with an intermediate of formula (III) according to the reaction described for the general preparation of compounds of formula (I).

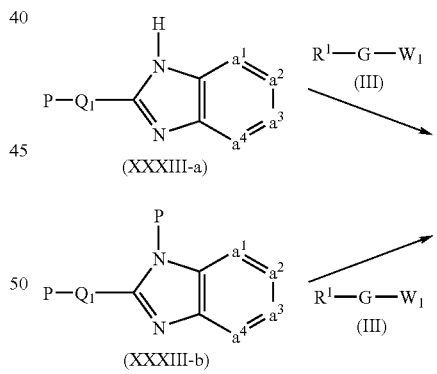

Intermediates of formula (IV) can also be prepared by reacting an intermediate of formula (XXXIII-a) with an intermediate of formula (XXXIV) that has reacted with methanesulfonyl chloride, in the presence of a suitable base, such as sodium hydride, and in the presence of a suitable reaction-inert solvent, e.g. N,N-dimethylformamide.

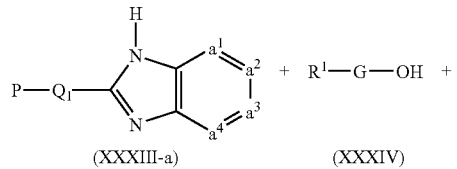

Intermediates of formula (IV) can also be prepared by a cyclization reaction of an intermediate of formula (XXXV) in a reaction-inert solvent, e.g. an alcohol or N,N-dimethylformamide, in the presence of mercury oxide and sulphur.

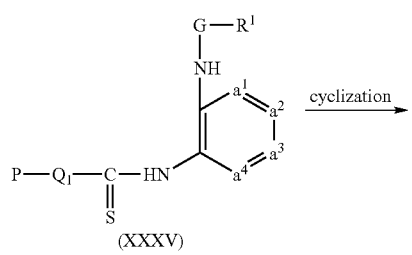

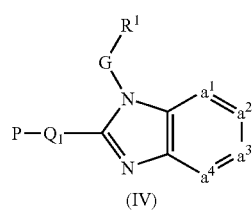

Intermediates of formula (IV) wherein $Q_1$ comprises an unsaturated bond, said $Q_1$ being represented by $Q_{1a}$(CH=CH), and said intermediates by formula (IV-a), can be prepared by reacting an intermediate of formula (XXXVI) with an intermediate of formula (III) in the presence of a suitable base, such as dipotassium carbonate.

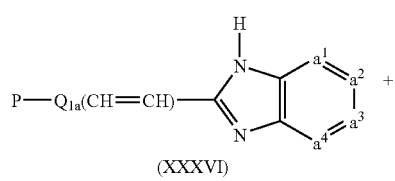

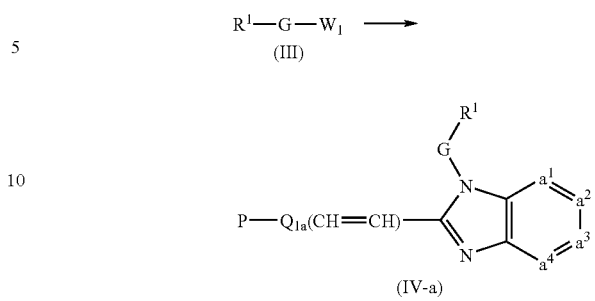

Intermediates of formula (IV) wherein, in the definition of $Q_1$, the $X^1$ or $X^2$ moieties in the radicals of formula (b-1) to (b-8) represent NH, said $Q_1$ being represented by $Q_{1c}$-NH, and said intermediates by formula (IV-b), may also be prepared by reacting an intermediate of formula (XXXVII) with an intermediate of formula (XXXVIII).

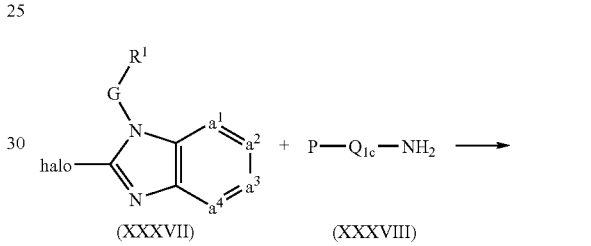

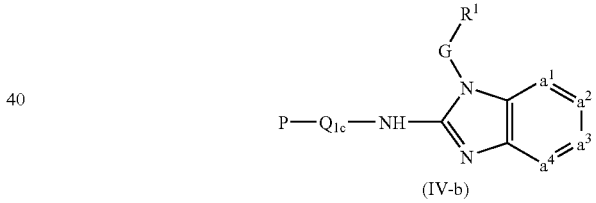

Intermediates of formula (IV) wherein $R^1$ is a bicyclic heterocycle substituted with amino or mono- or di($C_{1-6}$alkyl)amino, said $R^1$ being represented by $R^{5a}R^{5b}N$—$R^{1'}$, wherein $R^{5a}$ and $R^{5b}$ are defined as described above, and said intermediates being represented by formula (IV-c), can be prepared by reacting an intermediate of formula (XXXIX) with an appropriate amine, represented by formula (XL), in the presence of an appropriate catalyst, e.g. palladium, and (R)-(+)-2,2'-bis(diphenyl-phosphino)-1,1'-binaphtyl, in a suitable reaction-inert solvent, e.g. tetrahydrofuran.

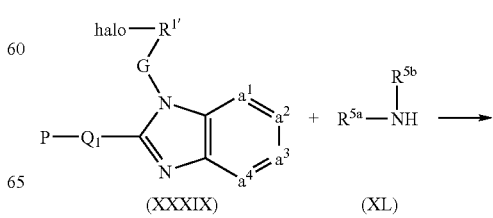

-continued

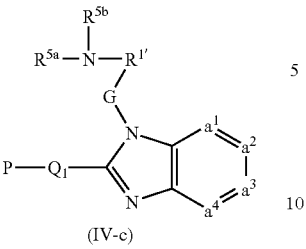

(IV-c)

Intermediates of formula (IV) wherein $R^1$ is a bicyclic heterocycle substituted with $C(=O)-NR^{5a}R^{5b}$, wherein $R^{5a}$ and $R^{5b}$ defined as described above, said $R^1$ being represented by $R^{5a}R^{5b}N-C(=O)-R^{1'}$, and said intermediates being represented by formula (IV-d), can be prepared by reacting an intermediate of formula (XXXIX) with an appropriate amine, represented by formula (XL), under an atmosphere of carbon monoxide, in the presence of a suitable catalyst, e.g. palladium (II) acetate, and 1,3-bis(diphenylphosphino)propane, in a suitable reaction-inert solvent, e.g. tetrahydrofuran.

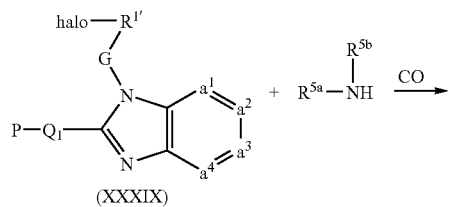

(XXXIX)

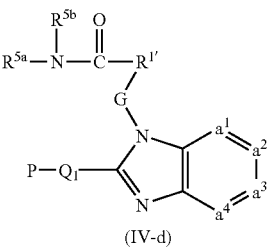

(IV-d)

Intermediates of formula (IV) wherein $P-Q_1$ comprises $C_{1-10}$alkyl or $C_{3-7}$cycloalkyl substituted with $NR^6-P$, said $C_{1-10}$alkyl or $C_{3-7}$cycloalkyl being represented by $Z_3$, said $P-Q_1$ being represented by $P-NR^6-Z_3-Q_{1b}$, and said intermediates being represented by formula (IV-e), can be prepared by reacting a compound of formula (I-a-3) with an intermediate of formula (XLI), wherein $W_4$ represents a suitable leaving group, such as p-toluenesulphonate. Said reaction can be performed in a reaction-inert solvent, e.g. acetonitrile, in the presence of a suitable base, e.g. dipotassium carbonate.

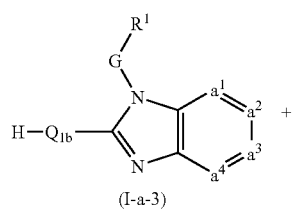

(I-a-3)

-continued

P—N(R^6)—Z_3—W_4

(XLI)

[structure]

(IV-e)

Intermediates of formula (IV-e), wherein $R^6$ is hydroxyC$_{1-6}$alkyl, said intermediates being represented by formula (IV-e-1), can be prepared by reacting an intermediate of formula (XLII) with an intermediate of formula (XLIII) in the presence of a suitable base, e.g. dipotassium carbonate, and a suitable solvent, e.g. acetonitrile.

[structure]

(XLII)

P—NH—C$_{1-6}$alkylOH (XLIII)

[structure]

(IV-e-1)

Intermediates of formula (XXXIII-a) or (XXXIII-b) can be prepared by protecting an intermediate of formula (XLIV) with a suitable protecting group, such as, for example, $C_{1-4}$alkyloxycarbonyl, in a reaction-inert solvent, such as methylene chloride or an alcohol, e.g. methanol, ethanol, 2-propanol and the like, in the presence of a suitable reagent, e.g. di $C_{1-4}$alkyl dicarbonate and optionally in the presence of a suitable base, e.g. sodium acetate.

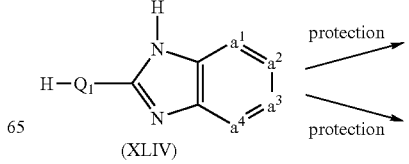

(XLIV)

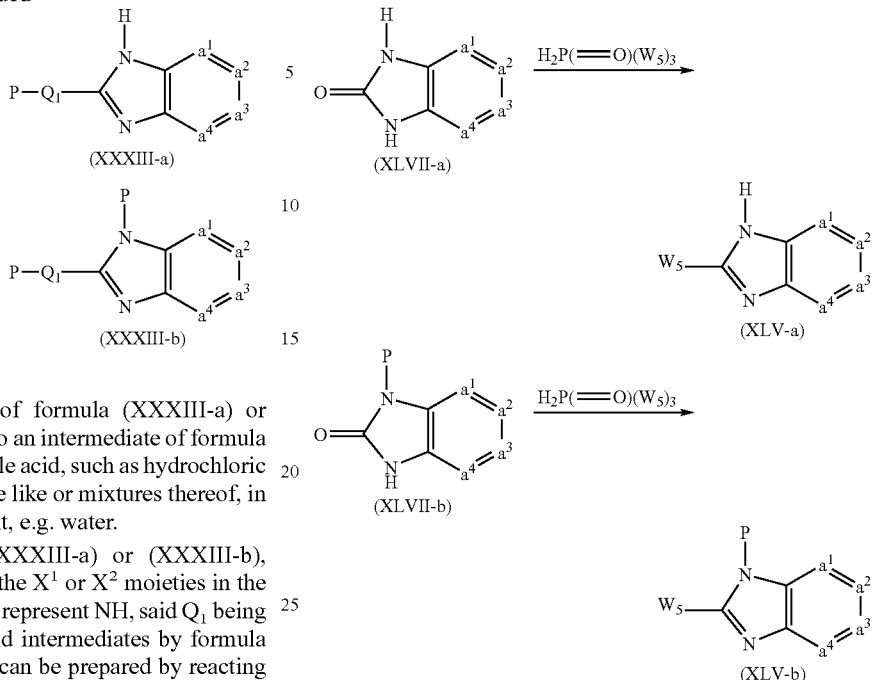

Alternatively, intermediates of formula (XXXIII-a) or (XXXIII-b) can be converted into an intermediate of formula (XLIV) by reaction with a suitable acid, such as hydrochloric acid or hydrobromic acid and the like or mixtures thereof, in the presence of a suitable solvent, e.g. water.

Intermediates of formula (XXXIII-a) or (XXXIII-b), wherein in the definition of $Q_1$, the $X^1$ or $X^2$ moieties in the radicals of formula (b-1) to (b-8) represent NH, said $Q_1$ being represented by $Q_{1c}$-NH, and said intermediates by formula (XXXIII-a-1) or (XXXIII-b-1), can be prepared by reacting an intermediate of formula (XLV-a) or (XLV-b), wherein $W_5$ represents a suitable leaving group, such as for example a halo atom, e.g. chloro, with an intermediate of formula (XLVI).

Intermediates of formula (XLVII-a) or (XLVII-b) can be prepared by reacting an intermediate of formula (XLVIII-a) or (XLVIII-b) with an intermediate of formula (IL).

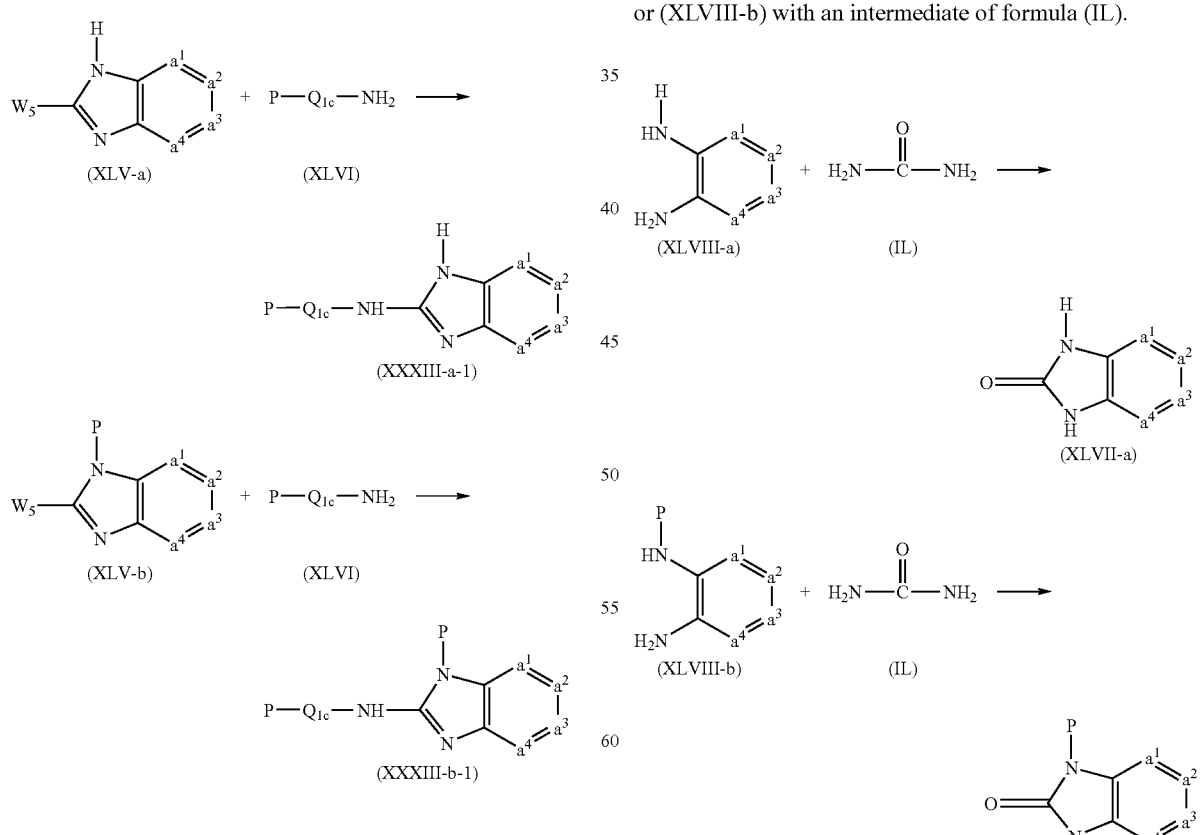

Intermediates of formula (XLV-a) or (XLV-b) can be prepared by reacting an intermediate of formula (XLVII-a) or (XLVII-b) with $H_2P(=O)(W_5)_3$ in the presence of a suitable acid, e.g. hydrochloric acid.

Intermediates of formula (XXXIII-a) can also be prepared by reacting an intermediate of formula (XLVIII-a) with P-$Q_1$-C(=NH)—O—$CH_2$—$CH_3$ in a reaction-inert solvent, such as an alcohol.

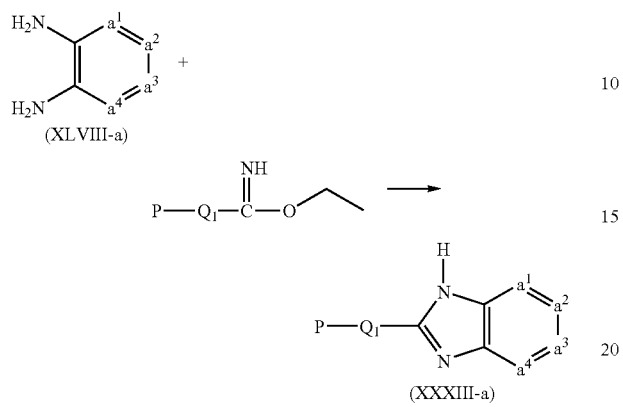

Intermediates of formula (XXXV) can be prepared by reacting an intermediate of formula (L) with an intermediate of formula P-$Q_1$=C=S, which is synthesized according to the procedures described in EP 0005318, in a reaction-inert solvent, such as an alcohol, e.g. ethanol. To increase the reaction rate, the reaction may be performed at elevated temperatures.

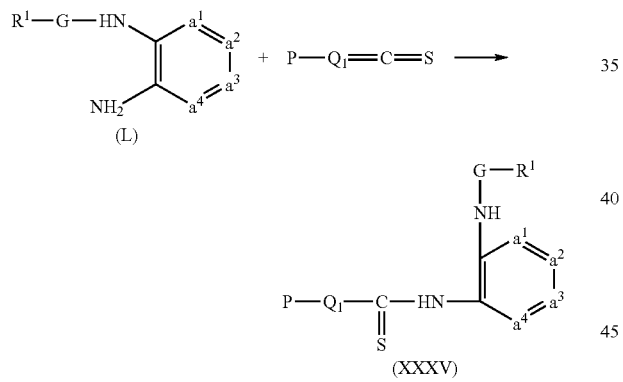

Intermediates of formula (L) can be obtained by reducing an intermediate of formula (LI) in a reaction-inert solvent, e.g. an alcohol, in the presence of a suitable reducing agent, e.g. hydrogen, and an appropriate catalyst, e.g. Raney Nickel.

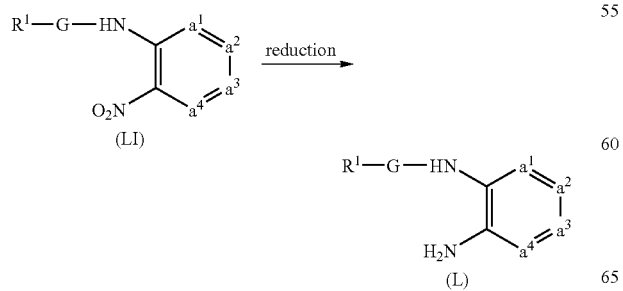

Intermediates of formula (LI) can be prepared by reacting an intermediate of formula (LII) with an intermediate of formula (LIII), in which $W_6$ represents a suitable leaving group, such as a halo atom, e.g. chloro. This reaction may be performed in a reaction-inert solvent, e.g. acetonitrile, in the presence of a suitable base, e.g. dipotassium carbonate.

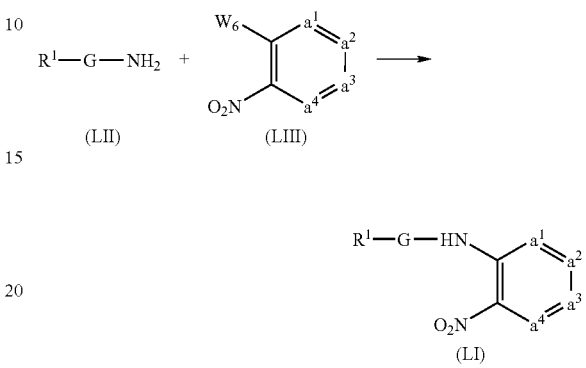

Intermediates of formula (LII) can be prepared by reacting an intermediate of formula (LIV) with a suitable acid, such as hydrochloric acid, in the presence of a suitable solvent, e.g. an alcohol, e.g. ethanol.

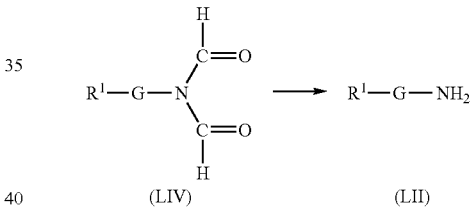

Intermediates of formula (LIV) can be prepared by reacting an intermediate of formula (III) with NaN[C(=O)H]$_2$.

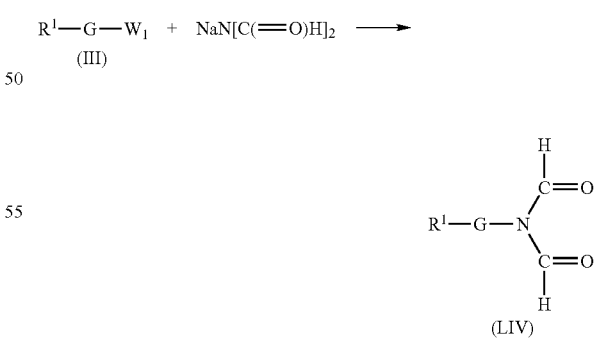

Intermediates of formula (LI) can also be prepared by reacting an intermediate of formula (LIII) with an intermediate of formula (LV) (J. Org. Chem., 25, p 1138, 1960) in a reaction-inert solvent, e.g. N,N-dimethylformamide, in the presence of an appropriate base, e.g. sodium hydride.

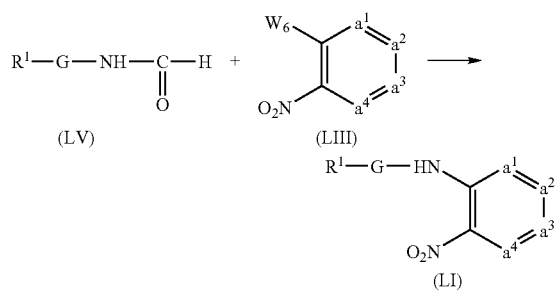

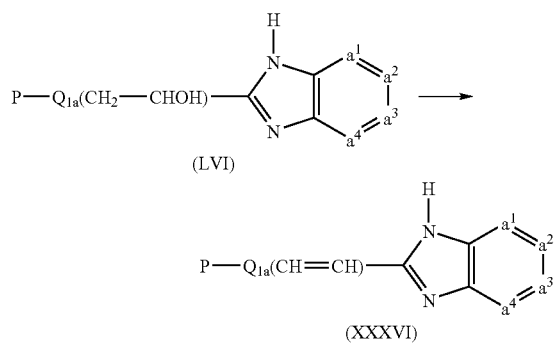

Intermediates of formula (XXXVI) can be prepared by dehydrating an intermediate of formula (LVI) with a suitable acid, such as sulfuric acid.

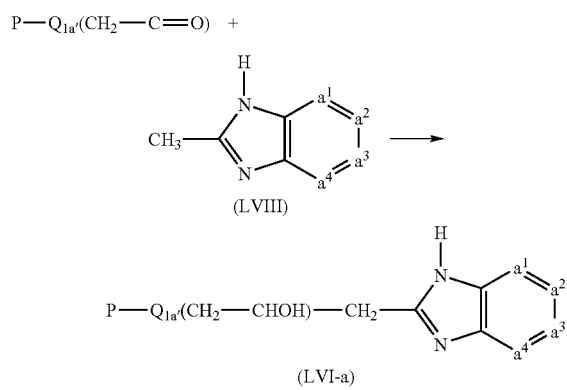

Intermediates of formula (LVI) wherein, in the definition of $Q_{1a}$, the $X^1$ or $X^2$ moieties are $CH_2$, said $Q_{1a}$ being represented by $Q_{1a'}$, and said intermediates being represented by formula (LVI-a), can be prepared by reacting a carbonyl moiety of formula (LVII) with an intermediate of formula (LVIII) in the presence of N,N-diisopropylamine and butyl lithium, in a suitable reaction-inert solvent, e.g. tetrahydrofuran.

Intermediates of formula (V), wherein G is $C_{1-10}$alkanediyl substituted with $C_{1-6}$alkyloxy, aryl$C_{1-6}$alkyloxy, HO(—$CH_2CH_2O)_n$—, $C_{1-6}$alkyloxy(—$CH_2CH_2O)_n$—, or aryl$C_{1-6}$alkyloxy(—$CH_2CH_2O)_n$—, said group of substituents being represented by O-$Z_4$, said G being represented by $Z_4$-O-$G_1$, and said intermediates being represented by formula (IV-f), can be prepared by reacting an intermediate of formula (XXXIII-a), with an intermediate of formula (LIX), optionally in the presence of a suitable acid, such as p-toluene-sulfonic acid and the like, and optionally in the presence of a suitable solvent, such as N,N-dimethylacetamide. To increase the reaction rate, the reaction may be carried out at elevated temperatures.

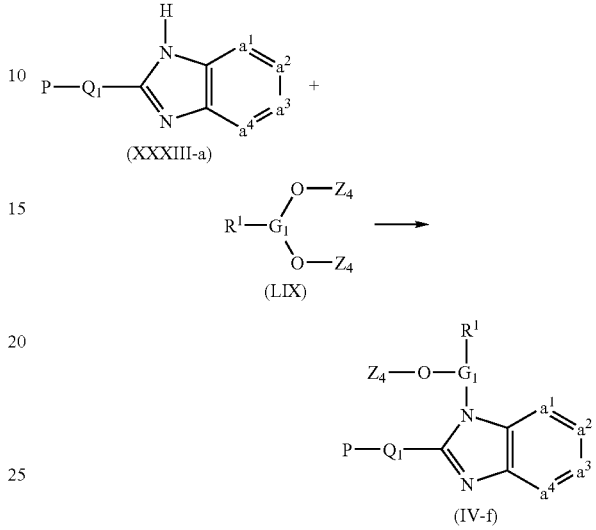

Intermediates of formula (LIX) can be prepared by reacting an intermediate of formula (LX) with a reagent of formula (LXI) or (LXII) in a reaction-inert solvent, such as an alcohol, or toluene, in the presence of an acid, e.g. 4-methylbenzenesulphonic acid.

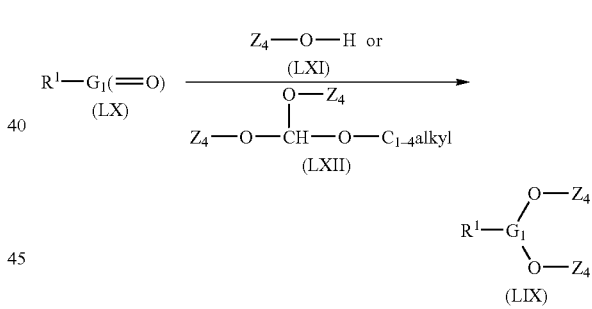

Intermediates of formula (LX) can be prepared by oxidizing an intermediate of formula (LXIII) with a suitable oxidizing agent, e.g. $MnO_2$, in a reaction-inert solvent, such as methylene chloride.

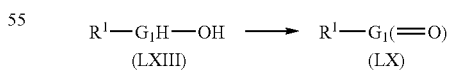

Intermediates of formula (IV-f) can also be prepared by reacting an intermediate of formula (IV) wherein G is $C_{1-10}$alkanediyl substituted with hydroxy, said G being represented by $G_1$-OH, and said intermediates being represented by formula (IV-g), with an intermediate of formula (LXIV), wherein $W_7$ is a suitable leaving group, such as a halo atom, e.g. iodo, in the presence of a suitable base, e.g. sodium hydride, in a reaction-inert solvent, e.g. tetrahydrofuran.

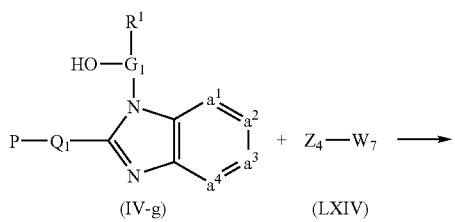

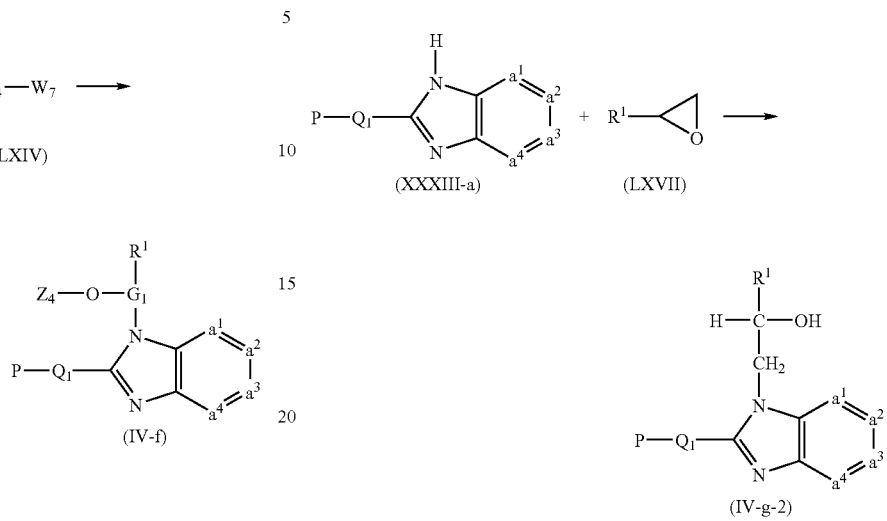

Intermediates of formula (IV-g), wherein the carbon atom of $G_1$ carrying the hydroxy, also carries a hydrogen atom, said $G_1$-OH being represented by H-$G_2$-OH, and said intermediates being represented by formula (IV-g-1), can be prepared by reducing an intermediate of formula (LXV) in the presence of a suitable reducing agent, e.g. sodium borohydride, in a reaction-inert solvent, such as an alcohol, tetrahydrofuran or a mixture thereof. Intermediates of formula (LXV) can also first be deprotected, e.g. in the presence of a suitable acid, such as hydrochloric acid and the like, resulting in intermediates of formula (LXVI), followed by a reduction, resulting in a compound of formula (I-q-1) wherein Q represents H-$Q_1$, said compounds being represented by formula (I-q-1-1).

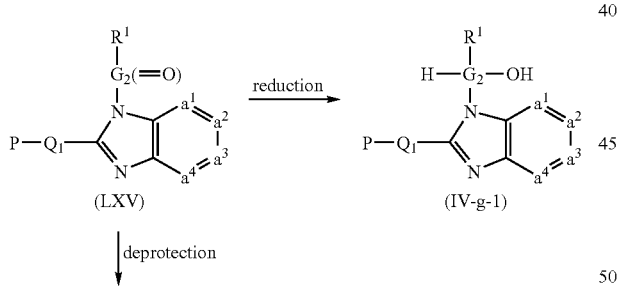

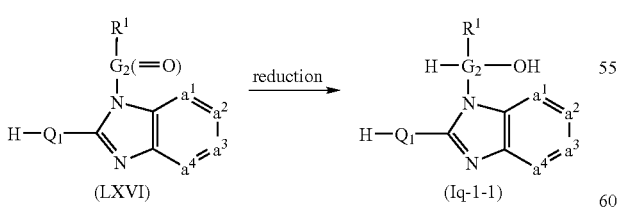

Intermediates of formula (IV), wherein G is ethyl substituted with hydroxy, said intermediates being represented by formula (IV-g-2) can also be prepared by reacting an intermediate of formula (XXXIII-a) with an intermediate of formula (LXVII) in the presence of a suitable base, such as sodium hydride, in a reaction-inert solvent, such as N,N-dimethylformamide.

A subgroup of intermediates of formula (IV-g-2), represented by formula (IV-g-2-1), can also be prepared by reacting an intermediate of formula (LXVIII) with an intermediate of formula (LXIX) in the presence of 1,3-dicyclohexylcarbodiimide, in a reaction-inert solvent, e.g. toluene.

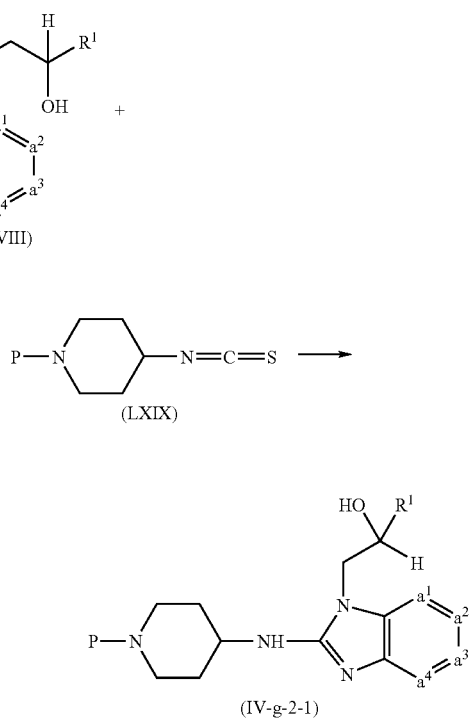

Intermediates of formula (LXV) can be prepared by reacting an intermediate of formula (XXXIII-a) with an intermediate of formula (LXX), wherein $W_8$ is a suitable leaving group, such as a halo atom, e.g. bromo, in the presence of a suitable base, e.g. sodium hydride, in a reaction-inert solvent, e.g. N,N-dimethylformamide.

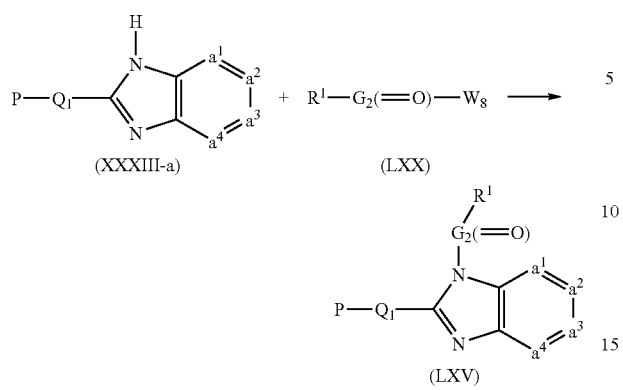

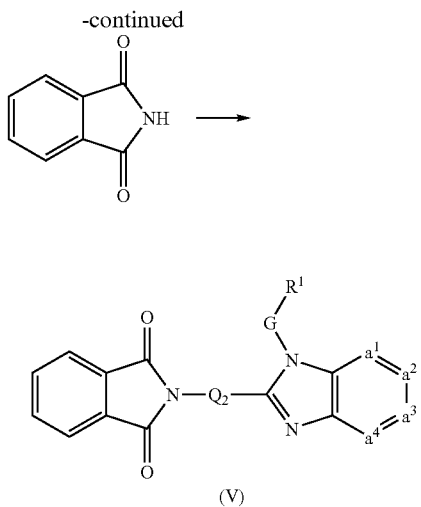

Intermediates of formula (V) can be prepared by reacting an intermediate of formula (LXXI) with 1H-isoindole-1,3 (2H)-dione in the presence of triphenylphosphine and diethyl azodicarboxylate.

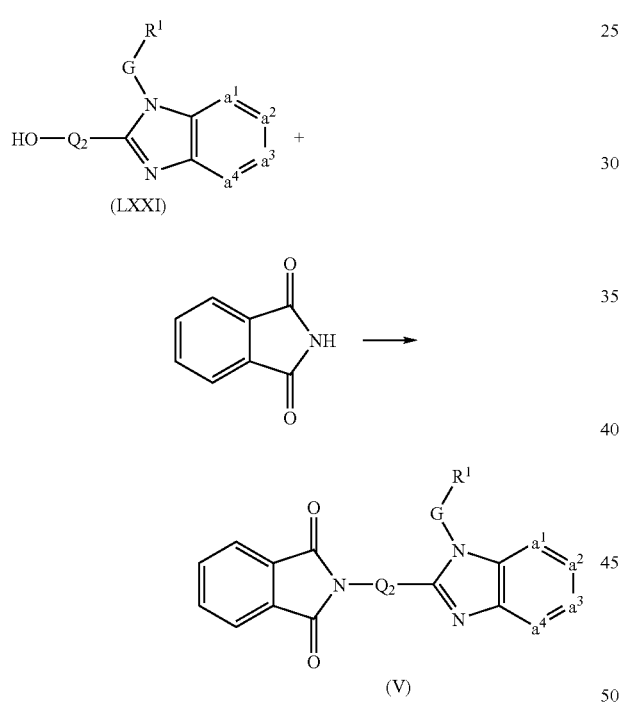

Intermediates of formula (LXXII) can be prepared by reacting an intermediate of formula (LXXI) with an intermediate of formula (LXXIII), wherein $W_9$ represents a suitable leaving group, such as a halo atom, e.g. chloro, in the presence of a suitable base, such as N,N-diethyl-ethanamine, and a suitable solvent, such as methylene chloride.

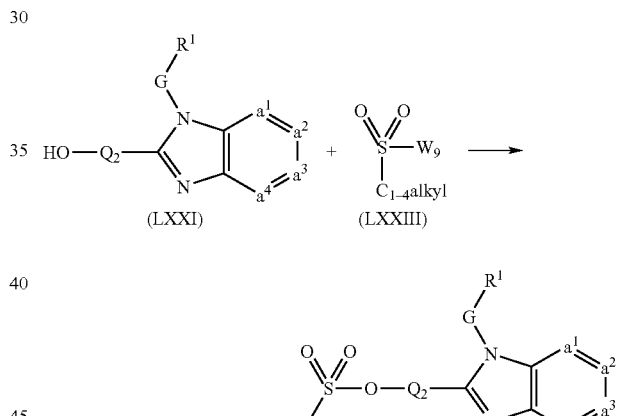

Intermediates of formula (V) may also be prepared by reacting an intermediate of formula (LXXII) with 1H-isoindole-1,3 (2H)-dione in the presence of a suitable base, such as sodium hydride, and a suitable solvent, such as N,N-dimethylformamide.

Intermediates of formula (V), wherein in the definition of $Q_2$, $R^2$ is $C_{1-10}$alkyl, said $Q_2$ being represented by $C_{1-10}$alkyl-$Q_{1b}$, and said intermediates by formula (V-a), can be prepared by reacting a compound of formula (I-a-3) with an intermediate of formula (LXXIV), wherein $W_{10}$ is a suitable leaving group, such as a halo atom, e.g. chloro, in the presence of a suitable base, such as dipotassium carbonate, and a suitable solvent, such as acetonitrile.

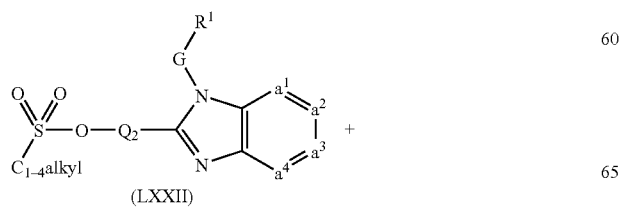

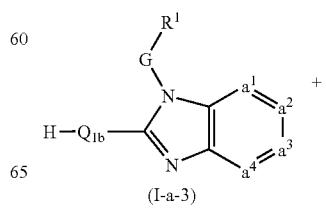

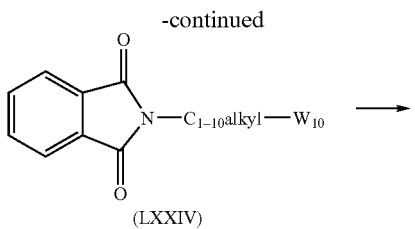

(LXXIV)

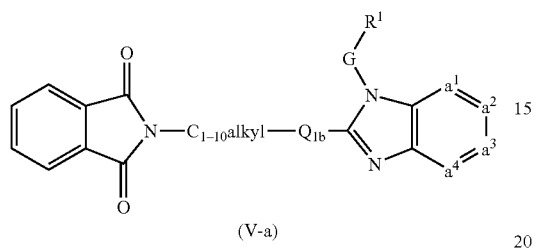

(V-a)

Intermediates of formula (LXXI) wherein, in the definition of $Q_2$, the carbon atom carrying the hydroxy, also carries two hydrogen atoms, said HO-$Q_2$ being represented by HO—$CH_2$-$Q_{2'}$, and said intermediates being represented by formula (LXXI-a), can be prepared by reducing an intermediate of formula (LXXV) in the presence of a suitable reducing agent, such as lithium aluminium hydride, in a suitable reaction-inert solvent, e.g. tetrahydrofuran.

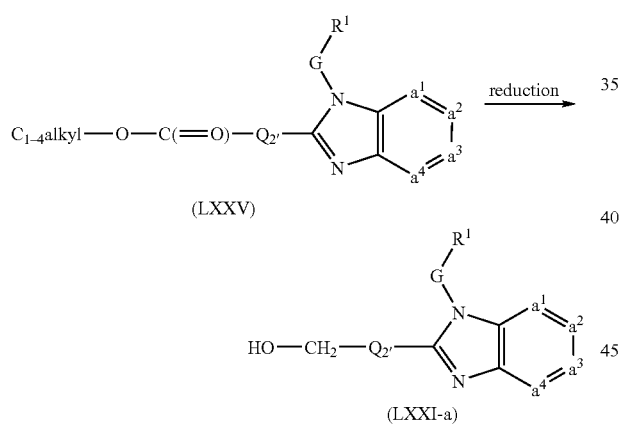

Intermediates of formula (LXXI), wherein, in the definition of $Q_2$, the carbon atom carrying the hydroxy, carries also at least one hydrogen atom, said HO-$Q_2$ being represented by HO-$Q_3$H, and said intermediates being represented by formula (LXXI-b), can be prepared by reducing an intermediate of formula (IX) with a suitable reducing agent, e.g. sodium borohydride, in a reaction-inert solvent, e.g. an alcohol.

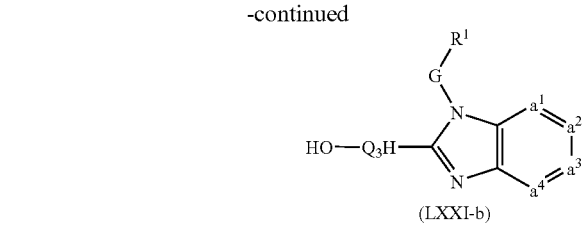

(LXXI-b)

Intermediates of formula (VI) wherein, in the definition of $Q_2$, $R^2$ is $C_{1-10}$alkyl substituted with $N(P)_2$ and the carbon atom adjacent to the nitrogen atom carrying the $R^2$ substituent carries also at least one hydrogen atom, said $Q_2$ being represented by $(P)_2N$—$C_{1-10}$alkyl-NH-$Q_{2a}$H, and said intermediates being represented by formula (VI-a), can be prepared by reductive amination of an intermediate of formula (LXXVI) with an intermediate of formula (LXXVII) in the presence of a suitable reductive agent, such as hydrogen, and a suitable catalyst, such as palladium-on-charcoal, platinum-on-charcoal, and the like, and optionally in the presence of a suitable catalyst poison, such as a thiophene solution. A suitable solvent in this reaction is a reaction-inert solvent, such as an alcohol.

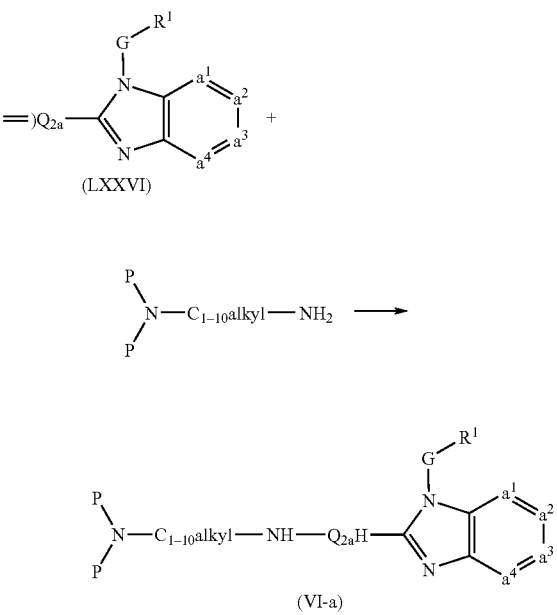

Intermediates of formula (LXXVI can be prepared by deprotecting an intermediate of formula (LXXVIII) in the presence of a suitable acid, such as hydrochloric acid and the like, in a suitable solvent, e.g. water.

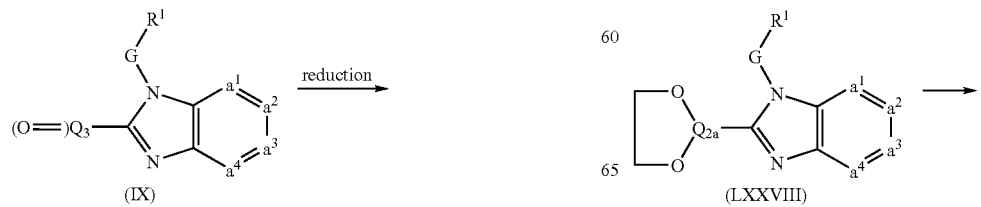

(LXXVIII)

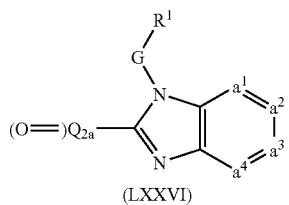

(LXXVI)

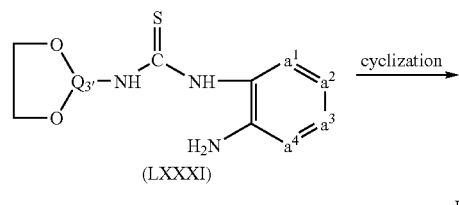

(LXXXI)

cyclization

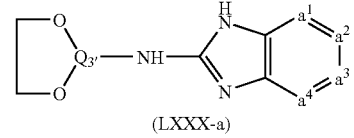

(LXXX-a)

Intermediates of formula (IX) may be prepared by deprotecting an intermediate of formula (LXXIX) in the presence of a suitable acid, e.g. hydrochloric acid and the like.

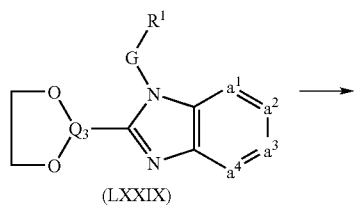

(LXXIX)

Intermediates of formula (LXXXI) can be prepared by reducing an intermediate of formula (LXXXII) in the presence of a suitable reducing agent, such as hydrogen, in the presence of a suitable catalyst, such as palladium-on-charcoal, platinum-on-charcoal and the like, in a suitable solvent, e.g. a mixture of ammonia in alcohol. Suitable alcohols are methanol, ethanol, 2-propanol and the like.

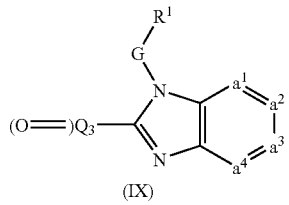

(IX)

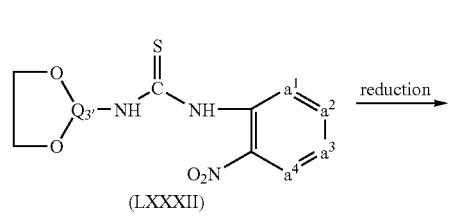

(LXXXII)

reduction

Intermediates of formula (LXXIX) can be prepared by reacting an intermediate of formula (LXXX) with an intermediate of formula (III) in the presence of a suitable base, e.g. dipotassium carbonate, in a suitable reaction-inert solvent, e.g. acetonitrile.

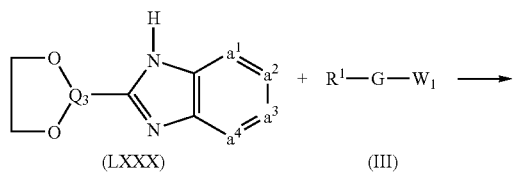

(LXXX)   (III)

Intermediates of formula (LXXXII) can be prepared by reacting an intermediate of formula (LXXXIII) with an intermediate of formula (LXXXIV) in a suitable reaction-inert solvent, e.g. ethanol.

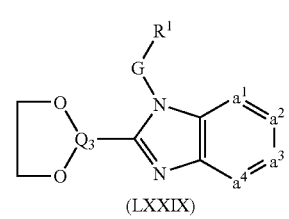

(LXXIX)

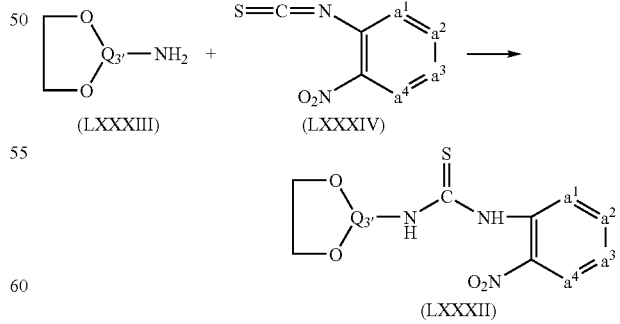

(LXXXIII)   (LXXXIV)

Intermediates of formula (LXXX) wherein, in the definition of $Q_3$, the $X^1$ or $X^2$ moiety of the radicals of formula (b-1) to (b-8) represent NH, said $Q_3$ being represented by $Q_{3'}$-NH, and said intermediates being represented by formula (LXXX-a), may be prepared by cyclizing an intermediate of formula (LXXXI) in the presence of mercury oxide and sulphur, in a suitable reaction-inert solvent, e.g. an alcohol.

Intermediates of formula (IX), wherein, in the definition of $Q_3$, $R^2$ comprises $C_{1-10}$alkyl, said $Q_3$ being represented by $C_{1-10}$alkyl-$Q_{1b}$, and said intermediates being represented by formula (IX-a), can be prepared by reacting a compound of formula (I-a-3) with a reagent of formula (LXXXV), wherein (O=)$C_{1-10}$alkyl represents a carbonyl derivative of $C_{1-10}$alkyl and wherein $W_{11}$ is a suitable leaving group, such as a halo atom, e.g. bromo, in a reaction-inert solvent, e.g. acetonitrile, in the presence of a suitable base, e.g. dipotassium carbonate.

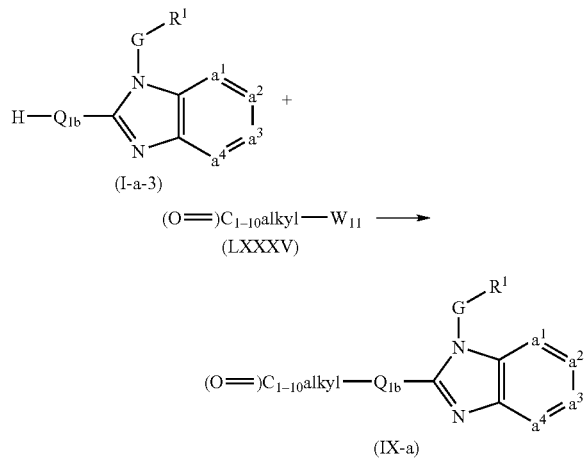

Intermediates of formula (X) wherein $Q_4$ comprises $C_{1-9}$alkyl, said $Q_4$ being represented by $C_{1-9}$alkyl-$Q_{1b}$, and said intermediates being represented by formula (X-a), can be prepared by reacting a compound of formula (I-a-3) with a reagent of formula (LXXXVI) wherein $W_{12}$ represents a suitable leaving group, such as a halo atom, e.g. chloro, in a reaction-inert solvent, e.g. 3-methyl-2-butanone, in the presence of a suitable base, e.g. dipotassium carbonate, sodium bicarbonate and the like.

Intermediates of formula (X), wherein NC-$Q_4$ represents NC—($C_{1-9}$alkyl)($R^4$)N—C(=O)-Alk-$X^1$, said intermediates being represented by formula (X-b), can be prepared by reacting an intermediate of formula (LXXXVII) with an intermediate of formula (LXXXVIII) in the presence of di-1H-imidazol-2-yl-methanone, a suitable base, such as N,N-diethyl-ethanamine, and a suitable solvent, such as methylene chloride.

Intermediates of formula (XI), wherein $Q_{4'}$ represents $Q_{1b}$, said intermediates being represented by formula (XI-a), can be prepared by reacting a compound of formula (I-a-3) with an intermediate of formula (LXXXIX), wherein $W_{13}$ represents a suitable leaving group, such as a halo atom, e.g. chloro, in the presence of a suitable base, such as disodium carbonate, and in the presence of a suitable solvent, such as 3-methyl-2-butanone.

Intermediates of formula (XIX) can be prepared by reacting an intermediate of formula (XC) with a suitable acid, such as hydrochloric acid.

-continued

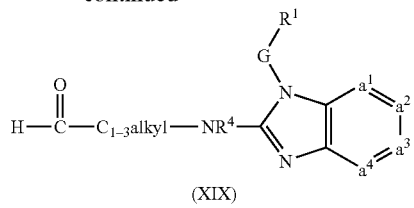

(XIX)

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV).

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The following examples are intended to illustrate the present invention.

EXPERIMENTAL PART

Hereinafter, "DMF" is defined as N,N-dimethylformamide, "DIPE" is defined as diisopropyl ether.

A. Preparation of the Intermediate Compounds

Example A1 a) Sodium methoxide (0.2 mol) was added to a mixture of N-(4-piperidinyl)-1H-benzimidazol-2-amine dihydrobromide (0.1 mol) in methanol (389 ml), the mixture was cooled on an ice bath and stirred for 2 hours.

Di-tert-butyldicarbonate (0.1 mol) was added to a cooled mixture on an ice bath and then stirred for 18 hours at room temperature. The mixture was evaporated and suspended in water/DIPE. The residue was filtered off, washed with water/DIPE and dried. The residue was boiled up in $CH_3OH$, yielding 17.46 g (55.2%) of 1,1-dimethylethyl 4-(1H-benzimidazol-2-ylamino)-1-piperidinecarboxylate; mp. 249.4° C. (interm. 1).

b) A mixture of intermediate (1) (0.05 mol), 2-(chloromethyl)quinoline monohydrochloride (0.055 mol) and sodium carbonate (0.075 mol) in DMF (250 ml) was stirred at 55° C. overnight. The solvent was evaporated. The residue was taken up in $H_2O$ and $CH_2Cl_2$. The organic layer was separated, dried, filtered and the solvent was evaporated. The residue was purified by column chromatography over silica gel (eluent: $CH_2Cl_2/CH_3OH$ 97/3 and 95/5). The pure fractions were collected and the solvent was evaporated. The residue was suspended in DIPE, filtered off and dried, yielding 13.5 g (59%) of 1,1-dimethylethyl 4-[[1-(quinolinylmethyl)-1H-benzimidazol-2-yl]amino]-1-piperidinecarboxylate (interm. 2).

Example A2 a) A mixture of 5,6,7,8-tetrahydro-2(1H)-quinoxalinone in phosphoryl chloride (200 ml) was stirred and refluxed for 3 hours. The solvent was evaporated. The residue was taken up in ice and $CH_2Cl_2$. The mixture was basified with $NH_4OH$. The organic layer was separated, dried ($MgSO_4$), filtered and the solvent was evaporated, yielding 34 g (86%) of 2-chloro-5,6,7,8-tetrahydroquinoxaline (interm. 3).

b) A mixture of intermediate (3), 1-bromo-2,5-pyrolidinedione (0.116 mol) and dibenzoyl peroxide (1.3 g) in tetrachloromethane (400 ml) was stirred and refluxed for 35 minutes, brought to room temperature and then filtered. The reaction was carried out again using the same quantities. The residues were combined. The solvent was evaporated. The residue (60 g) was purified by column chromatography over silica gel (eluent: cyclohexane/EtOAc 85/5; 15-35 μm). Two pure fractions were collected and their solvents were evaporated, yielding 25 g (43%) of (±)-5-bromo-2-chloro-5,6,7,8-tetrahydroquinoxaline (interm. 4) and 12 g (21%) of (±)-8-bromo-2-chloro-5,6,7,8-tetrahydroquinoxaline.

c) A dispersion of sodium hydride in mineral oil (60%) (0.0518 mol) was added portionwise at 5° C. under $N_2$ flow to a mixture of intermediate (1) (0.0471 mol) in DMF (200 ml). The mixture was stirred at 5° C./10° C. for 1 hour. A solution of intermediate (4) (0.0565 mol) in DMF (50 ml) was added dropwise. The mixture was stirred at room temperature for 3 hours and poured out into $H_2O$. The precipitate was filtered off and taken up in $CH_2Cl_2$. The organic solution was dried ($MgSO_4$), filtered and the solvent was evaporated. The residue (32 g) was purified by column chromatography over silica gel (eluent: $CH_2Cl_2/CH_3OH/NH_4OH$ 95/5/0.1; 20-45 μm). The pure fractions were collected and the solvent was evaporated, yielding 13.3 g (58%) of (±)-1,1-dimethylethyl 4-[[1-(2-chloro-5,6,7,8-tetrahydro-5-quinoxalinyl)-1H-benzimidazol-2-yl]amino]-1-piperidinecarboxylate (interm. 5).

Example A3 a) 2,3-Butanedione (0.0776 mol) was added at room temperature to a solution of sodium pyrosulfite (0.1 mol) in water (75 ml). The mixture was heated to 70° C. and then added to a solution of ethyl 2,3-diaminobenzoate (0.0776 mol) in water (75 ml). The mixture was stirred at 100° C. for 12 hours, cooled, basified with $K_2CO_3$ 10% and extracted with EtOAc. The organic layer was separated, dried ($MgSO_4$), filtered and the solvent was evaporated. The residue (17.5 g) was purified by column chromatography over silica gel (eluent: $CH_2Cl_2/$EtOAc 93/7; 20-45 μm). The pure fractions were collected and the solvent was evaporated, yielding 12 g (67%) of ethyl 2,3-dimethyl-5-quinoxalinecarboxylate (interm. 6).

b) Lithium chloride (0.6 mol) was added portionwise at 80° C. to a mixture of intermediate (6) (0.06 mol) and potassium tetrahydroborate (0.6 mol) in tetrahydrofuran (300 ml). The mixture was stirred at 80° C. for 5 hours, cooled, poured out into $H_2O$ and extracted with EtOAc. The organic layer was separated, washed with H₂O, dried (MgSO₄), filtered and the solvent was evaporated, yielding 10.5 g (91%) of (±)-1,2,3,4-tetrahydro-2,3-dimethyl-5-quinoxaline-methanol (interm. 7).

c) MnO₂ (10 g) was added portionwise at room temperature to a mixture of intermediate (7) (0.0546 mol) in dichloromethane (500 ml). The mixture was stirred at room temperature overnight, filtered over celite, washed with CH₂Cl₂ and the filtrate was evaporated. The product was used without further purification, yielding 7.8 g (77%) of 2,3-dimethyl-5-quinoxalinecarboxaldehyde (interm. 8).

d) Sodium tetrahydroborate (0.084 mol) was added portionwise at 5° C. to a mixture of intermediate (8) (0.042 mol) in methanol (100 ml). The mixture was stirred at 5° C. for 30 minutes, hydrolized cold and extracted with EtOAc. The organic layer was separated, dried (MgSO₄), filtered and the solvent was evaporated, yielding 6.7 g (85%) 2,3-dimethyl-5-quinoxalinemethanol (interm. 9).

e) Thionyl chloride (0.045 mol) was added dropwise at 5° C. to a mixture of intermediate (9) (0.03 mol) in dichloromethane (50 ml). The mixture was stirred at room temperature for 2 hours, poured out on ice and K₂CO₃ 10%. The organic layer was separated, washed with K₂CO₃ 10%, dried (MgSO₄), filtered and the solvent was evaporated. The product was used without further purification, yielding 6.2 g (quant.) of 5-(chloromethyl)-2,3-dimethyl-quinoxaline (interm. 10).

f) A dispersion of sodium hydride in mineral oil (60%) (0.021 mol) was added portionwise at 5° C. under N₂ flow to a mixture of intermediate (1) (0.02 mol) in DMF (30 ml). The mixture was stirred at 5° C. under N₂ flow for 1 hour. A solution of intermediate (10) (0.03 mol) in a small amount of DMF was added dropwise at 5° C. The mixture was stirred at room temperature under N₂ flow for 2 hours, hydrolized and extracted with EtOAc. The organic layer was separated, washed several times with H₂O, dried (MgSO₄), filtered and the solvent was evaporated. The residue (12.5 g) was purified by column chromatography over silica gel (eluent: CH₂Cl₂/CH₃OH/NH₄OH 97.5/2.5/0.1; 20-45 μm). Two pure fractions were collected and their solvents were evaporated, yielding 7.8 g (80%) of 1,1-dimethylethyl 4-[[1-[(2,3-dimethyl-5-quinoxalinyl)methyl]-1H-benzimidazol-2-yl]amino]-1-piperidinecarboxylate (interm. 11).

Example A4

8-Bromo-2-methylquinoline (0.0675 mol) was added portionwise at −70° C. under N₂ flow to a mixture of a solution of butyllithium in hexane (1.6M) (0.135 mol) in tetrahydrofuran (300 ml) and diethyl ether (300 ml). The mixture was stirred for 30 minutes. A solution of DMF (0.405 mol) in tetrahydrofuran (100 ml) was added quickly. The mixture was cooled to −70° C. and stirred for 15 minutes. Ethanol (70 ml) and a NH₄Cl solution 10% were added. The mixture was brought to room temperature and stirred for 15 minutes. NH₄Cl was added. The mixture was extracted with EtOAc. The organic layer was separated, washed with H₂O, dried (MgSO₄), filtered and the solvent was evaporated. The product was used without further purification, yielding 15 g (>100%) of 2-methyl-8-quinolinecarboxaldehyde (interm. 12).

Example A5 a) A mixture of 3-methoxy-2-methylquinoline (0.081 mol) in trifluoro-acetic acid (150 ml) was hydrogenated at room temperature under a 3-4 bar pressure for 48 hours with palladium on activated carbon (2 g) as a catalyst. After uptake of hydrogen (2 equiv.), the catalyst was filtered through celite and washed with H₂O. The filtrate was basified with a concentrated NH₄OH solution and extracted with CH₂Cl₂. The organic layer was separated, dried (MgSO₄), filtered and the solvent was evaporated, yielding 14.3 g (quant.) of 5,6,7,8-tetrahydro-3-methoxy-2-methylquinoline (interm. 13).

b) 3-Chlorobenzenecarboperoxoic acid (0.1 mol) was added portionwise at 5° C. to a mixture of intermediate (13) (0.067 mol) in dichloromethane (300 ml). The mixture was stirred at room temperature overnight, basified with K₂CO₃ 10% and separated into its layers. The aqueous layer was extracted with CH₂Cl₂. The combined organic layer was dried (MgSO₄), filtered and the solvent was evaporated, yielding 13.7 g (quant.) of 5,6,7,8-tetrahydro-3-methoxy-2-methylquinoline, 1-oxide (interm. 14).

c) A mixture of intermediate (14) (0.067 mol) in acetic anhydride (100 ml) was stirred at 90° C. for 1 hour, poured out on ice and basified with NaOH 3N. CH₂Cl₂ was added. The organic layer was separated, washed with a diluted NaOH solution, dried (MgSO₄), filtered and the solvent was evaporated, yielding 16.8 g (quant.) of 5,6,7,8-tetrahydro-3-methoxy-2-quinolinemethanol acetate (ester) (interm. 15).

d) A mixture of intermediate (15) (0.067 mol) and sodium hydroxide (13 g) in methanol (60 ml) was stirred and refluxed for 20 minutes, poured out on ice and extracted with CH₂Cl₂. The organic layer was separated, dried (MgSO₄), filtered and the solvent was evaporated, yielding 12.3 g (95%) of 5,6,7,8-tetrahydro-3-methoxy-2-quinolinemethanol (interm. 16).

In a similar way was also prepared (±)-5,6,7,8-tetrahydro-2-methyl-8-quinolinol (interm. 17).

Example A6

Phosphorus tribromide (0.0105 mol) was added dropwise at 0° C./5° C. under N₂ flow to a mixture of (±)-5,6,7,8-tetrahydro-2-methyl-8-quinolinol (intermediate 17) (0.03 mol) in toluene (20 ml). The mixture was brought to room temperature and stirred at room-temperature overnight. Ice water was added. The mixture was basified with a concentrated NaOH solution and extracted with CH₂Cl₂. The organic layer was separated, dried (MgSO₄), filtered and the solvent was evaporated. The residue (6 g) was purified by column chromatography over silica gel (eluent: CH₂Cl₂/CH₃OH 99/1; 20-45 μm). The pure fractions were collected and the solvent was evaporated, yielding 2 g (29%) of (±)-8-bromo-5,6,7,8-tetrahydro-2-methylquinoline (interm. 18).

Example A7 a) A mixture of N-2,6-dimetyl-2,3-pyridinediamine (0.122 mol) in trifluoro-acetic acid (250 ml) was stirred and refluxed for 6 hours and brought to room temperature. The solvent was evaporated. The residue was taken up in CH₂Cl₂ and K₂CO₃ 10%. The organic layer was separated, dried (MgSO₄), filtered and the solvent was evaporated. The residue (32 g) was purified by column chromatography over silica gel (eluent: CH₂Cl₂/EtOAc 97/3; 20-45 μm). The pure fractions were collected and the solvent was evaporated. The residue was taken up in petroleum ether. The precipitate was filtered off and dried, yielding 15 g of residue (fraction 1). The mother layer was evaporated. The residue was combined with 14.1 g of fraction 1, yielding 28.9 g of 1,6-dimethyl-2-(trifluoromethyl)-1H-imidazo[4,5-b]pyridine; mp. 100° C. (interm. 19).

b) 1-Bromo-2,5-pyrolidinedione (0.0735 mol) and dibenzoyl peroxide (1.5 g) were added at room temperature to a solution of intermediate (19) (0.07 mol) in tetrachloromethane (450 ml). The mixture was stirred and refluxed for 7 hours, then brought to room temperature and filtered. The reaction was carried out again using the same quantities. The mixtures were combined. The solvent was evaporated. The residue (50 g) was purified by column chromatography over silica gel (eluent: $CH_2Cl_2/CH_3OH$ 100/0 and 98/2; 20-45 μm). The pure fractions were collected and the solvent was evaporated, yielding 20.2 g (49%) of 6-(bromomethyl)-1-methyl-2-(trifluoromethyl)-1H-imidazo[4,5-b]pyridine (interm. 20).

c) A mixture of ethyl 4-(1H-benzimidazol-2-ylamino)-1-piperidine-carboxylate (0.0464 mol), intermediate (20) (0.051 mol) and potassium carbonate (0.1392 mol) in acetonitrile (250 ml) was stirred and refluxed for 90 minutes and then brought to room temperature. Water was added and the mixture was extracted twice with $CH_2Cl_2$. The combined organic layer was dried ($MgSO_4$), filtered and the solvent was evaporated. The product was used without further purification, yielding 23 g (>100%) of ethyl 4-[[1-[[1-methyl-2-(trifluoromethyl)-1H-imidazo[4,5-b]pyridin-6-yl]methyl]-1H-benzimidazol-2-yl]amino]-1-piperidinecarboxylate (interm. 21).

Example A8

A mixture of ethyl 4-(1H-benzimidazol-2-ylamino)-1-piperidine-carboxylate (0.0289 mol), 7-chloro-6,7-dihydro-5H-cyclopenta[b]pyridine (0.0289 mol) and potassium carbonate (0.0867 mol) in acetonitrile (250 ml) was stirred and refluxed for 48 hours and then brought to room temperature. The reaction was carried out again using the same quantities. The mixtures were combined, poured out into $H_2O$ and extracted with EtOAc. The organic layer was separated, washed with $H_2O$, dried ($MgSO_4$), filtered and the solvent was evaporated. The residue (25 g) was purified by column chromatography over silica gel (eluent: $CH_2Cl_2/CH_3OH$ $NH_4OH$ 97/3/0.5; 20-45 μm). Two fractions were collected and their solvents were evaporated, yielding 8 g of ethyl 4-[[1-(6,7-dihydro-5H-1-pyrindin-7-yl) 1H-benzimidazol-2-yl]amino]-1-piperidinecarboxylate (interm. 22).

Example A9 a) A dispersion of sodium hydride in mineral oil (0.261 mol) was added portionwise at room temperature under $N_2$ flow to a mixture of N-8-quinolinylformamide (0.174 mol) in DMF (500 ml). The mixture was stirred at room temperature for 1 hour. A solution of 1-chloro-2-nitrobenzene (0.53 mol) in DMF (200 ml) was added dropwise. The mixture was stirred at 140° C. for 12 hours and then brought to room temperature. $H_2O$ was added and the mixture was extracted with $CH_2Cl_2$. The organic layer was separated, dried ($MgSO_4$), filtered and the solvent was evaporated. The residue (110 g) was purified by column chromatography over silica gel (eluent: $CH_2Cl_2$/cyclohexane 80/20; 20-45 μm). The pure fractions were collected and the solvent was evaporated, yielding 9.8 g (21%) of N-(2-nitrophenyl)-8-quinolinamine (interm. 23).

b) A mixture of 6-quinolinemethanamine (0.074 mol), 2-chloro-3-nitropyridine (0.0888 mol) and potassium carbonate (0.185 mol) in acetonitrile (200 ml) was stirred and refluxed for 5 hours and then cooled to room temperature. EtOAc and $H_2O$ were added. The mixture was extracted with HCl 3N. The aqueous layer was basified with $K_2CO_3$ solid and extracted with $CH_2Cl_2$. The combined organic layer was dried ($MgSO_4$), filtered and the solvent was evaporated, yielding 17.8 g (84%) of N-(3-nitro-2-pyridinyl)-8-quinolinemethanamine (interm. 24).

Example A10 a) A mixture of intermediate (24) (0.064 mol) in methanol (200 ml) was hydrogenated under a 3 bar pressure for 2 hours with Raney nickel (10 g) as a catalyst. After uptake of hydrogen (3 equiv), the catalyst was filtered through celite and the filtrate was evaporated, yielding 14.8 g (93%) of N2-(8-quinolinylmethyl)-2,3-pyridinediamine (interm. 25).

b) A mixture of intermediate (25) (0.059 mol) and ethyl 4-isothiocyanato-1-piperidine-carboxylate (0.059 mol) in methanol (150 ml) was stirred and refluxed for 4 hours and brought to room temperature. The solvent was evaporated. The residue was purified by column chromatography over silica gel (eluent: $CH_2Cl_2/CH_3OH$ 97/3; 20-45 μm). The desired fractions were collected and the solvent was evaporated, yielding 10.5 g (37%) of ethyl 4-[[[[2-[(8-quinolinylmethyl)amino]-3-pyridinyl]amino]sulfinyl]-amino]-1-piperidine-carboxylate (interm. 26)

c) A mixture of intermediate (26) (0.026 mol), mercury(II) oxide (0.052 mol) and sulfur (0.2 g) in ethanol (120 ml) was stirred and refluxed for 2 hours, brought to room temperature and filtered over celite. The filtrate was evaporated, yielding 8.7 g (96%) of 4-[[1-(8-quinolinylmethyl)-1H-imidazo[4,5-b]pyridin-2-yl]amino]-1-piperidine-carboxylate (interm. 27).

Example A11 a) A mixture of 8-quinolinecarboxaldehyde (0.092 mol) and 4-methylbenzenesulfonic acid (0.3 g) in 2-ethoxyethanol (110 ml) was stirred and refluxed for 24 hours using a Dean Stark apparatus. The solvent was evaporated. The reaction was carried out again using the same quantities. The residues were combined and taken up in $CH_2Cl_2$. The organic solution was washed with $K_2CO_3$ 10% and decanted. The organic layer was dried ($MgSO_4$), filtered and the solvent was evaporated. The residue (41 g) was purified by column chromatography over silica gel (eluent: $CH_2Cl_2/CH_3OH$ 98/2; 20-45 μm). Two pure fractions were collected and their solvents were evaporated, yielding 20 g (34%) of 8-[bis(2-ethoxyethoxy)methyl]quinoline (interm. 28).

b) A mixture of 8-quinolinecarboxaldehyde (0.248 mol), triethoxymethane (0.4464 mol) and 4-methylbenzenesulfonic acid (4 g) in ethanol (250 ml) was stirred and refluxed for 1 hour, brought to room temperature, poured out into $K_2CO_3$ 10% and extracted with EtOAc. The organic layer was separated, dried ($MgSO_4$), filtered and the solvent was evaporated. The product was used without further purification, yielding 48.5 g (80%) of 8-(diethoxymethyl)-quinoline (interm. 29).

c) A mixture of 2-quinolinecarboxaldehyde (0.08 mol) and 4-methylbenzenesulfonic acid (0.25 g) in ethanol (100 ml) was stirred and refluxed for 48 hours and brought to room temperature. The reaction was carried out again using the same quantities. The mixtures were combined. The solvent was evaporated. The residue was taken up in $CH_2Cl_2$. The organic solution was washed with $K_2CO_3$ 10% and with $H_2O$, then dried ($MgSO_4$), filtered and the solvent was evaporated. The product was used without further purification, yielding 32.5 g of 2-(diethoxymethyl)quinoline (interm. 30).

Example A12

Intermediate (1) (0.0377 mol) and intermediate (29) (0.0755 mol) were heated at 160° C. for 1 hour and then purified by column chromatography over silica gel (eluent: $CH_2Cl_2/CH_3OH$ 98/2; 15-35 μm). The pure fractions were collected and the solvent was evaporated, yielding 15 g (79%) of (±)-1,1-dimethylethyl 4-[[1-[ethoxy(8-quinolinyl)methyl]-1H-benzimidazol-2-yl]amino]-1-piperidinecarboxylate (interm. 31).

Example A13

4-Methylbenzenesulfonyl chloride (0.2222 mol) was added portionwise at 10° C. to a mixture of 1,1-dimethylethyl [1-(hydroxymethyl)-2-methylpropyl]carbamic acid (ester) (0.202 mol) in pyridine (65 ml). The mixture was stirred at 10° C. for 2 hours. H₂O (75 ml) was added at 10° C. The precipitate was filtered off, washed with H₂O and taken up in CH₂Cl₂. The organic solution was washed with H₂O, dried, filtered and the solvent was evaporated, yielding 49 g (68%) of (±)-1,1-dimethylethyl [1-[[[(4-methylphenyl)sulfonyl]oxy]methyl]-2-methylpropyl]carbamate; mp. 85° C. (interm. 32).

Example A14 a) A mixture of compound (33) (0.0347 mol), 1-bromo-3-methyl-2-butanone (0.052 mol) and potassium carbonate (0.104 mol) in acetonitrile (255 ml) was stirred and refluxed for 2 hours and filtered. The filtrate was evaporated. The residue was taken up in H₂O and the mixture was extracted with EtOAc. The organic layer was separated, dried (MgSO₄), filtered and the solvent was evaporated. The product was used without further purification, yielding 16.84 g of (±)-1-[4-[[1-[ethoxy(8-quinolinyl)methyl]-1H-benzimidazol-2-yl]amino]-1-piperidinyl]-3-methyl-2-butanone (interm. 34) (quant.).

In a similar way were also prepared:
1-[4-(1H-benzimidazol-2-ylamino)-1-piperidinyl]-3-methyl-2-butanone;
1-[4-[[1-(8-quinolinyl)-1H-benzimidazol-2-yl]amino]-1-piperidinyl]-3-methyl-2-butanone; and
1-[4-[[1-(2-quinolinylmethyl)-1H-benzimidazol-2-yl]amino]-1-piperidinyl]-3-methyl-2-butanone.

b) A mixture of intermediate (34) (0.036 mol) in methanol (200 ml) was stirred at 10° C. Sodium tetrahydroborate (0.04 mol) was added portionwise. The mixture was stirred for 90 minutes. H₂O was added. The solvent was evaporated. The residue was extracted with CH₂Cl₂. The organic layer was separated, washed with H₂O, dried (MgSO₄), filtered and the solvent was evaporated, yielding 17 g (96%) of (±)-4-[[1-[ethoxy(8-quinolinyl)methyl]-1H-benzimidazol-2-yl]amino]-alpha-(1-methylethyl) 1-piperidineethanol (interm. 35).

c) Diethyl azodicarboxylate (0.015 mol) was added dropwise at 0° C. under N₂ flow to a solution of intermediate (35) (0.01 mol), phthalimide (0.015 mol) and triphenylphosphine (0.015 mol) in tetrahydrofuran (100 ml). The mixture was stirred at room temperature for 2 hours. EtOAc was added. The mixture was extracted with HCl 3N and separated into its layers. The aqueous layer was washed twice with EtOAc, basified with K₂CO₃ solid and extracted with CH₂Cl₂. The combined organic layer was dried (MgSO₄), filtered and the solvent was evaporated. The residue was purified by column chromatography over silica gel (eluent: CH₂Cl₂/CH₃OH/NH₄OH 97/3/0.2; 20-45 μm). Two pure fractions were collected and their solvents were evaporated, yielding 2.3 g (30%) of (±)-2-[2-[4-[[1-[ethoxy(8-quinolinyl)methyl]-1H-benzimidazol-2-yl]amino]-1-piperidinyl]-3-methylbutyl]-1H-isoindole-1,3(2H)dione (interm.

d) Preparation of Intermediate

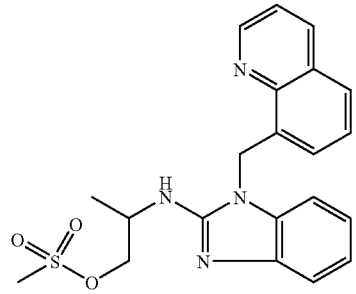

(80)

A solution of

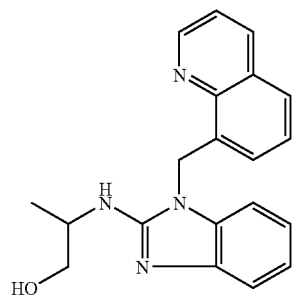

(0.024 mol) (prepared according to A14b) and Et₃N (0.072 mol) in CH₂Cl₂ (100 ml) was cooled to 0° C. under N₂ flow. A mixture of methanesulfonyl chloride (0.036 mol) in CH₂Cl₂ (a small amount) was added dropwise. The mixture was allowed to cool to room temperature while stirring for 3 hours. Water was added. The mixture was decanted. The organic layer was dried (MgSO₄), filtered and the solvent was evaporated, yielding 8.5 g of intermediate (80) (86%).

e) Preparation of Intermediate

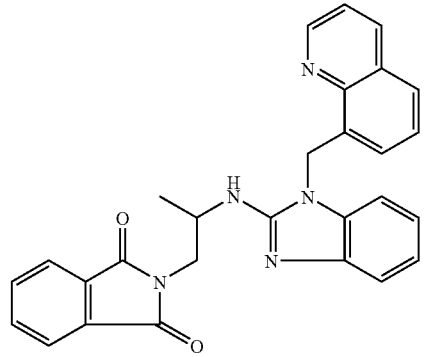

(81)

A solution of 1H-isoindole-1,3(2H)-dione (0.0828 mol) in DMF (80 ml) was cooled to 10° C. NaH 60% in oil (0.0828 mol) was added portionwise. The mixture was allowed to cool to room temperature while stirring for 1 hour. A mixture of intermediate (80) (0.0207 mol) (prepared according to A14d) in DMF (a small amount) was added dropwise. The mixture was stirred at room temperature for 1.5 hours, at 60° C. for 5 hours and at room temperature for the weekend. The residue

Example A15 a) A mixture of 1-[4-(1H-benzimidazol-2-ylamino)-1-piperidinyl]-3-methyl-2-butanone (0.03 mol) and benzenemethanamine (0.09 mol) in methanol (200 ml) was hydrogenated at 40° C. under a 3 bar pressure for 48 hours with palladium on activated carbon (1.3 g) as a catalyst. After uptake of hydrogen, the catalyst was filtered through celite, washed with $CH_3OH$ and the filtrate was evaporated. Hydrogenation was continued for 24 hours. After uptake of hydrogen, the catalyst was filtered through celite, washed with $CH_3OH$ and the filtrate was evaporated. The residue was purified by column chromatography over silica gel (eluent: $CH_2Cl_2/CH_3OH/NH_4OH$ 85/14/1; 20-45 μm). The desired fractions were collected and the solvent was evaporated. The residue was crystallized from diethyl ether. The precipitate was filtered off and dried, yielding 0.4 g of (±)-N-[1-(2-amino-3-methylbutyl)$_4$-piperidinyl]-1H-benzimidazol-2-amine; mp. 138° C. (interm. 37).

b) Di-tert-butyl dicarbonate (0.02 mol) was added at 5° C. to a mixture of intermediate (37) (0.0186 mol) in dichloromethane (60 ml). The mixture was stirred at room temperature for 3 hours and poured out into $H_2O$. The organic layer was separated, dried ($MgSO_4$), filtered and the solvent was evaporated. The product was used without further purification, yielding 5.9 g of (±)-1,1-dimethylethyl [1-[[4-[[1-[(1,1-dimethylethoxy)carbonyl]-1H-benzimidazol-2-yl]amino]-1-piperidinyl]methyl]-2-methylpropyl]carbamate (interm. 38).

Example A16

A mixture of 1-[4-[[1-(8-quinolinyl)-1H-benzimidazol-2-yl]amino]-1-piperidinyl]-3-methyl-2-butanone (0.0222 mol) and benzenemethanamine (0.0666 mol) in methanol (250 ml) was hydrogenated at 40° C. under a 3 bar pressure for 24 hours with palladium on activated carbon (1.5 g) as a catalyst. After uptake of hydrogen, the catalyst was filtered through celite, washed with $CH_2Cl_2$ and $CH_3OH$ and the filtrate was evaporated. Palladium on activated carbon (1.5 g) and methanol (250 ml) were added again. Hydrogenation was continued at 40° C. under a 3 bar pressure for 24 hours. After uptake of hydrogen, the catalyst was filtered through celite, washed with $CH_2Cl_2$ and the filtrate was evaporated. The residue (22 g) was purified by column chromatography over silica gel (eluent: $CH_2Cl_2/CH_3OH/NH_4OH$ 95/5/0.1 and 85/15/1; 20-45 μm). Three pure fractions were collected and their solvents were evaporated, yielding 2.6 g 1-[4-[[1-(1,2,3,4-tetrahydro-8-quinolinyl)-1H-benzimidazol-2-yl]amino]-1-piperidinyl]-3-methyl-2-butanone (interm. 40) (fraction 1), 2.9 g of fraction 2 and 0.7 g of fraction 3. Fraction 2 and 3 were crystallized from $CH_3CN$. The precipitate was filtered off and dried, yielding 0.82 g (±)-N-[1-[3-methyl-2-[(phenylmethyl)amino]butyl]-4-piperidinyl]-1-(1,2,3,4-tetrahydro-8-quinolinyl)-1H-benzimidazol-2-amine; mp. 126° C. and 0.55 g of N-(4-piperidinyl)-1-(1,2,3,4-tetrahydro-8-quinolinyl)-1H-benzimidazol-2-amine; mp. 205° C. (comp. 48).

Example A17 a) A mixture of N-(4-piperidinyl)-1-(4-quinolinylmethyl)-1H-benzimidazol-2-amine (comp. 23) (0.0129 mol), chloroacetonitrile (0.0155 mol), potassium iodide (0.00129 mol) and potassium carbonate (0.0258 mol) in 4-methyl-2-pentanone (80 ml) was stirred and refluxed for 5 hours. $H_2O$ was added. The solvent was evaporated. $H_2O$ and $CH_2Cl_2$ were added. The precipitate was filtered off. The filtrate was separated into its layers. The organic layer was dried ($MgSO_4$), filtered and the solvent was evaporated. The residue (3.5 g) was purified by column chromatography over silica gel (eluent: $CH_2Cl_2/CH_3OH/NH_4OH$ 95/5/0.3; 15-40 μm). The pure fractions were collected and the solvent was evaporated. The residue was crystallized from $CH_3CN$. The precipitate was filtered off and dried, yielding 0.94 g 4-[[1-(4-quinolinylmethyl)-1H-benzimidazol-2-yl]amino]-1-piperidineacetonitrile; mp. 190° C. (interm. 41).

b) A mixture of N-(4-piperidinyl)-[1,2'-bi-1H-benzimidazol]-2-amine (comp. 71) (0.01 mol), chloroacetonitrile (0.01 mol) and sodium hydrogen carbonate (0.02 mol) in DMF (50 ml) was stirred at 50° C. overnight. The solvent was evaporated. The residue was taken up in $H_2O$ and the mixture was extracted with $CH_2Cl_2$. The organic layer was separated, dried, filtered and the solvent was evaporated. The residue was suspended in DIPE, filtered off and dried, yielding 2.3 g (63%) of product. This fraction was purified over silica gel on a glass filter (eluent: $CH_2Cl_2/(CH_3OH/NH_3)$ 97/3). The pure fractions were collected and the solvent was evaporated, yielding 1.36 g (37%) of 4-[(1,2'-bi-1H-benzimidazol-2-yl)amino]-1-piperidine-acetonitrile (interm. 42).

Example A18

Preparation of Intermediate

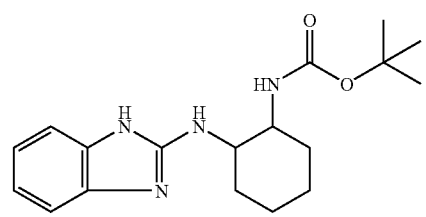

(84)

A mixture of 2-chloro-1H-benzimidazole (0.0189 mol) and 1,1-dimethylethyl 2-aminocyclohexanecarbamoate (0.04725 mol) (prepared according to A1a)) was stirred at 140° C. for 3 hours, then brought to room temperature and taken up in $CH_2Cl_2/CH_3OH$. The same procedure was repeated 3 times on the same quantities of 2-chloro-1H-benzimidazole and 1,1-dimethylethyl 2-aminocyclohexanecarbamoate. The mother layers were brought together, dried ($MgSO_4$), filtered and the solvent was evaporated. The residue (28 g) was purified by column chromatography over silica gel (eluent: $CH_2Cl_2/CH_3OH/NH_4OH$ 96/4/0.1; 15-35 μm). Two fractions were collected and the solvent was evaporated, yielding 4.5 g of intermediate (84) (24%).

Example A19

Preparation of Intermediate

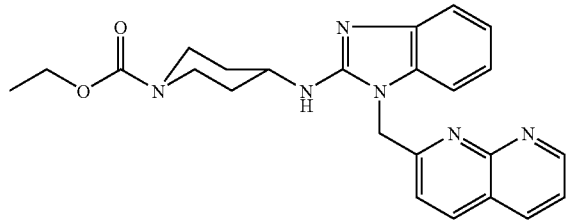
(76)

A mixture of quantities of ethyl 4-(1H-benzimidazol-2-ylamino)-1-piperidine-carboxylate (0.0154 mol),

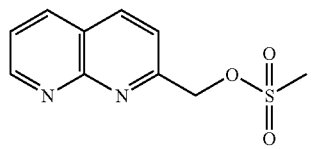

(0.0154 mol) (prepared according to A14d) and $K_2CO_3$ (0.0463 mol) in $CH_3CN$ (50 ml) and DMF (5 ml) was stirred and refluxed for 6 hours, poured out into $H_2O$ and extracted with EtOAc. The organic layer was separated, dried ($MgSO_4$), filtered and the solvent was evaporated. The residue was purified by column chromatography over silica gel (eluent: $CH_2Cl_2/CH_3OH$ 97/3; 35-70 µm). The pure fractions were collected and the solvent was evaporated, yielding: 0.87 g of intermediate (76) (13%).

Example A20 a) Preparation of Intermediate

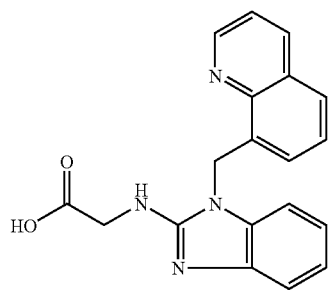
(82)

A solution of

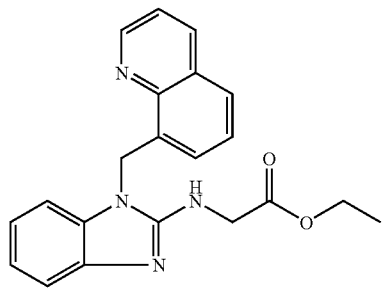

(0.0105 mol) (prepared according to A1b) in HCl 6N (60 ml) was stirred and refluxed for 12 hours and then brought to room temperature. The solvent was evaporated. The residue was taken up in 2-propanol. The precipitate was filtered off, washed with $CH_3CN$, washed with diethyl ether and dried, yielding: 4 g of intermediate (82) (94%).

b) Preparation of Intermediate

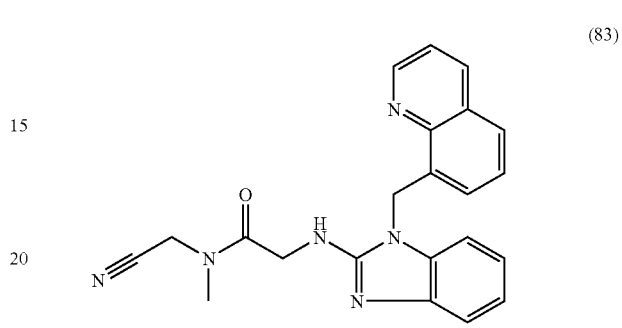
(83)

Intermediate (82 (0.0094 mol) was added at room temperature to $CH_2Cl_2$ (70 ml). $Et_3N$ (0.0188 mol) was added. 1,1'-carbonylbis-1H-imidazole (0.0188 mol) was added. The mixture was stirred at room temperature for 4.5 hours. (Methylamino)acetonitrile.HCl (0.0188 mol) was added. The mixture was stirred at room temperature for 12 hours. The organic layer was separated, washed twice with water, dried ($MgSO_4$), filtered and the solvent was evaporated. The residue was purified by column chromatography over silica gel (eluent: $CH_2Cl_2/CH_3OH$ 98.5/1.5; 35-70 µm). The pure fractions were collected and the solvent was evaporated. The residue (2.2 g) was crystallized from $CH_3CN$. The precipitate was filtered off and dried, yielding: 1.5 g of intermediate (83) (41%).

Example A21

A mixture of intermediate

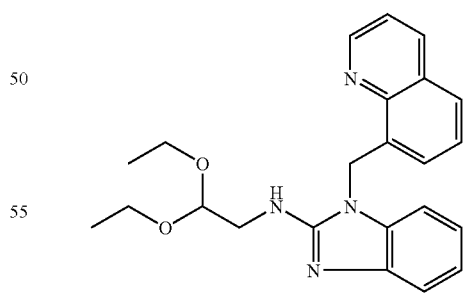

(interm. 85) (0.0461 mol) (prepared according to A1b) in HCl 3 N (200 ml) was stirred and refluxed for 1 hour. The solvent was evaporated. The residue was taken up in EtOAc and NH4OH. The mixture was stirred for 30 minutes and filtered. The solvent was evaporated. The product was used without further purification, yielding 14 g of

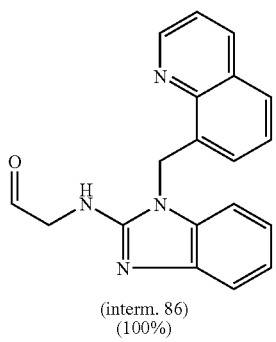

(interm. 86)
(100%)

Tables 1, 2 and 3 list intermediates which were prepared analogous to one of the above examples.

TABLE 1

| Int. No. | Ex. No. | $R^a$ | $R^b$ | $R^c$ | n | a | * | b | $R^d$ | $R^e$ | $R^f$ | $R^g$ |
|---|---|---|---|---|---|---|---|---|---|---|---|---|
| 43 | A10c | H | H | H | 1 | N | 2 | C | — | H | H | H |
| 44 | A12 | $CH_3$ | H | $O(CH_2)_2OC_2H_5$ | 1 | CH | 8 | C | H | H | H | — |
| 45 | A12 | $CH_3$ | H | $O(CH_2)_2OC_2H_5$ | 1 | CH | 2 | C | — | H | H | H |
| 46 | A7c | $CH_3$ | H | H | 1 | CH | 2 | N | — | $OCH_3$ | — | H |
| 47 | A7c | H | H | H | 1 | CH | 2 | C | — | H | H | Cl |
| 48 | A7c | H | H | H | 1 | CH | 2 | C | — | H | Cl | H |
| 49 | A7c | H | H | H | 1 | CH | 2 | C | — | H | H | H |
| 2 | A1b | $CH_3$ | H | H | 1 | CH | 2 | C | — | H | H | H |
| 50 | A12 | $CH_3$ | $CH_3$ | $OC_2H_5$ | 1 | CH | 8 | C | H | H | H | — |
| 51 | A12 | $CH_3$ | H | $OC_2H_5$ | 1 | CH | 2 | C | — | H | H | H |
| 52 | A12 | $CH_3$ | H | $OC_2H_5$ | 1 | CH | 2 | C | — | $OCH_3$ | H | H |
| 31 | A12 | $CH_3$ | H | $OC_2H_5$ | 1 | CH | 8 | C | H | H | H | — |
| 53 | A3f | H | H | H | 1 | CH | 8 | C | H | H | H | — |
| 54 | A3f | $CH_3$ | H | H | 1 | CH | 8 | N | H | H | — | — |
| 55 | A7c | $CH_3$ | H | H | 1 | CH | 8 | C | $CH_3$ | H | H | — |
| 11 | A3f | $CH_3$ | H | H | 1 | CH | 8 | N | $CH_3$ | $CH_3$ | — | — |
| 56 | A7c | H | H | H | 1 | CH | 4 | C | H | H | — | H |
| 57 | A7c | H | $CH_3$ | H | 1 | CH | 8 | C | H | H | H | — |
| 27 | A10c | H | H | H | 1 | N | 8 | C | H | H | H | — |
| 58 | A10c | H | H | — | 0 | CH | 8 | C | H | H | H | — |
| 66 | A12 | $CH_3$ | $CH_3$ | $O(C_2H_5)OC_2H_5$ | 1 | CH | 8 | C | H | H | H | — |
| 67 | A12 | $CH_3$ | H | $O(C_2H_5)OC_2H_5$ | 1 | CH | 8 | C | H | H | H | — |
| 68 | A1b | $CH_3$ | $CH_3$ | $CH_3$ | 1 | CH | 8 | C | H | H | H | — |
| 69 | A1b | $CH_3$ | H | H | 1 | CH | 2 | C | — | $OCH_3$ | H | H |
| 70 | A1b | $CH_3$ | H | H | 1 | CH | 2 | N | — | H | — | H |
| 71 | A1b | $CH_3$ | H | H | 1 | CH | 8 | C | $OCH_3$ | H | H | — |

* = position bicyclic heterocycle

TABLE 2

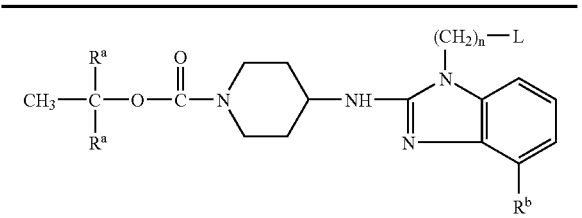

| Int. No. | Ex. No. | $R^a$ | $R^b$ | n | L |
|---|---|---|---|---|---|
| 59 | A2c | CH₃ | H | 0 | 3-chloro-5-methyl-5,6,7,8-tetrahydroquinoxalin-2-yl |
| 60 | A8 | H | H | 0 | 8-methyl-5,6,7,8-tetrahydroquinolin-2-yl |
| 61 | A2c | H | H | 0 | 5-methyl-5,6,7,8-tetrahydroquinoxalin-2-yl |
| 5 | A2c | CH₃ | H | 0 | 3-chloro-5-methyl-5,6,7,8-tetrahydroquinoxalin-2-yl |
| 21 | A7c | H | H | 1 | 5-methyl-2-(trifluoromethyl)-3H-imidazo[4,5-b]pyridin-3-yl |
| 62 | A3f | CH₃ | H | 1 | 2-methyl-6-methoxy-1H-benzimidazol-? |
| 63 | A7c | CH₃ | H | 1 | 1-methylisoquinolin-? |

TABLE 2-continued

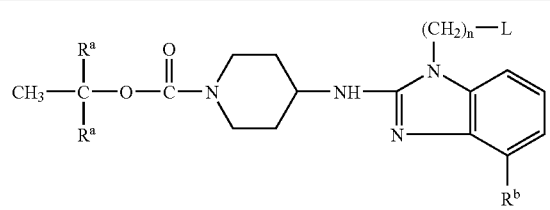

| Int. No. | Ex. No. | $R^a$ | $R^b$ | n | L |
|---|---|---|---|---|---|
| 64 | A7c | H | H | 1 | 2-benzothiazolyl |
| 65 | A2c | CH₃ | H | 0 | 2-benzoxazolyl |
| 22 | A8 | H | H | 0 | 7-methyl-6,7-dihydro-5H-cyclopenta[b]pyridin-2-yl |
| 72 | A2c | CH₃ | CH₃ | 0 | 3-chloro-5-methyl-5,6,7,8-tetrahydroquinoxalin-2-yl |
| 73 | A2c | CH₃ | CH₃ | 0 | 3-chloro-5-methyl-5,6,7,8-tetrahydroquinoxalin-2-yl |
| 74 | A2c | CH₃ | CH₃ | 0 | 5-methyl-5,6,7,8-tetrahydroquinoxalin-2-yl |
| 75 | A2c | CH₃ | CH₃ | 0 | 2,3-dimethyl-5-methyl-5,6,7,8-tetrahydroquinoxalin-? |

TABLE 2-continued

| Int. No. | Ex. No. | R$^a$ | R$^b$ | n | L |
|---|---|---|---|---|---|
| 76 | A19 | H | H | 1 | (2-methyl-1,8-naphthyridinyl) |

TABLE 3

| Int. No. | Ex. No. | L | Physical data |
|---|---|---|---|
| 77 | A1b | CH$_3$(CH$_2$)$_3$NHC(O)OC(CH$_3$)$_3$ | |
| 78 | A1b | CH$_3$CH$_2$CH$_2$N(CH$_3$)C(O)OC(CH$_3$)$_3$ | |
| 79 | A1b | (2-methylcyclohexyl)NHC(O)OC(CH$_3$)$_3$ | trans |
| 80 | A14d | H$_3$C-S(O)$_2$-O-CH$_2$CH(CH$_3$)$_2$ | |
| 81 | A14e | N-isobutyl phthalimide | |
| 82 | A20 | HO-CH$_2$CH$_2$-C(O)- 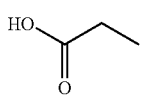 | |

TABLE 3-continued

| Int. No. | Ex. No. | L | Physical data |
|---|---|---|---|
| 83 | A20 | N≡C-CH$_2$CH$_2$-N(CH$_3$)-C(O)-CH$_2$CH$_3$ | |

B. Preparation of the Final Compounds

Example B1 a) A mixture of 2-propanol and hydrochloric acid (15 ml) was added to a mixture of intermediate (2) (0.0284 mol) in 2-propanol (150 ml). The mixture was stirred and refluxed for 90 minutes and cooled. The precipitate was filtered off, washed with 2-propanol and DIPE and dried, yielding 10.36 g of N-(4-piperidinyl)-1-(2-quinolinyl-methyl)-1H-benzimidazol-2-amine dihydrochloride (comp.1).

b) A mixture of compound (1) (0.01 mol) and sodium carbonate (0.03 mol) in 4-methyl-2-pentanone (250 ml) was stirred and refluxed for a few hours using a water separator (until gas development stops). 2-Bromoethyl carbamic acid 1,1-dimethylethyl ester (0.015 mol) was added. The mixture was stirred and refluxed for 18 hours using a water separator, then cooled, washed with H$_2$O, dried, filtered and the solvent was evaporated. The residue was purified by column chromatography over silica gel (eluent: CH$_2$Cl$_2$/C$_2$H$_5$OH 95/5 and 90/10). The pure fractions were collected and the solvent was evaporated, yielding 3.8 g of 1,1-dimethylethyl [2-[4-[[1-(2-quinolinylmethyl)-1H-benzimidazol-2-yl]amino]-1-piperidinyl]ethyl]carbamate (comp. 2).

c) A mixture of compound (2) (0.0076 mol) in a mixture of 2-propanol and hydrochloric acid (10 ml) and 2-propanol (100 ml) was stirred and refluxed for 1 hour and then cooled. The precipitate was filtered off, washed with 2-propanol and DIPE and dried, yielding 3.08 g of N-[1-(2-aminoethyl)-4-piperidinyl]-1-(2-quinolinylmethyl)-1H-benzimidazol-2-amine tetrahydrochloride monohydrate (comp. 3).

d) A mixture of compound (115) (0.00305 mol) in HBr/HOAc 33% (34 ml) was stirred at room temperature for 2 hours, poured out on ice, basified with a concentrated NH$_4$OH solution and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/CH$_3$OH/NH$_4$OH 96/4/0.2; 15-40 μm). Two fractions (F1 and F2) were collected and their solvents were evaporated, yielding 0.56 g F1 (46%) and 0.69 g F2 (50%). F1 was crystallized from diethyl ether. The precipitate was filtered off and dried, yielding 0.27 g of (±)-N-[1-(2-amino-3-methylbutyl)-4-piperidinyl]4-methyl-1-(8-quinolinylmethyl)-1H-benzimidazol-2-amine (comp. 116).

e) A mixture of compound (155) (0.0024 mol) in CH$_3$OH (3 ml) and 2-propanol (15 ml) was stirred and refluxed for 2 hours, filtered, washed with 2-propanol and dried. The residue (1.05 g) was taken up in CH$_2$Cl$_2$ and basified with NH$_4$OH. The organic layer was separated, dried (MgSO$_4$), filtered and the solvent was evaporated. The residue (0.42 g) was purified by column chromatography over silica gel (eluent: CH$_2$Cl$_2$/CH$_3$OH NH$_4$OH 85/15/2; 15-40 µm). The pure fractions were collected and the solvent was evaporated. The residue (0.35 g) was dissolved in CH$_3$OH and converted into the ethanedioic acid salt. The precipitate was filtered off and dried. This fraction was taken up in water and CH$_2$Cl$_2$ and alkalized with K$_2$CO$_3$ 10%. The organic layer was separated, dried (MgSO$_4$), filtered and the solvent was evaporated. The residue (0.21 g) was purified by column chromatography over silica gel (eluent: CH$_2$Cl$_2$/CH$_3$OH/NH$_4$OH 75/2811; 15-40 µm). The pure fractions were collected and the solvent was evaporated, yielding 0.13 g of compound (156).

Example B2

A mixture of intermediate (27) (0.02 mol) in hydrochloric acid (6N) (85 ml) was stirred and refluxed at 50° C. overnight and then brought to room temperature. The solvent was evaporated. The residue was taken up in K$_2$CO$_3$ 10% and extracted with CH$_2$Cl$_2$. The organic layer was separated, dried (MgSO$_4$), filtered and the solvent was evaporated, yielding 5 g (69%) of N-(4-piperidinyl)-3-(8-quinolinylmethyl)-3H-imidazo[4,5-b]pyridin-2-amine (comp. 41).

Example B3

A mixture of intermediate (41) (0.00668 mol) in a solution of ammonia in methanol (7N) (70 ml) was hydrogenated at room temperature under a 3 bar pressure for 5 hours with Raney nickel (2.7 g) as a catalyst. After uptake of hydrogen (2 equiv.), the catalyst was filtered through celite, washed with CH$_2$Cl$_2$ and CH$_3$OH and the filtrate was evaporated. The residue was taken up in CH$_2$Cl$_2$ and a small amount of CH$_3$OH. The organic solution was washed with H$_2$O, dried (MgSO$_4$), filtered and the solvent was evaporated. The residue was crystallized from EtOAc. The precipitate was filtered off and dried, yielding 1.6 g (60%) of N-[1-(2-aminoethyl)-4-piperidinyl]-1-(4-quinolinylmethyl)-1H-benzimidazol-2-amine; mp. 196° C. (comp. 24).

Example B4

A mixture of intermediate (36) (0.00351 mol) in hydrazine (2.5 ml) and ethanol (30 ml) was stirred and refluxed for 20 minutes and brought to room temperature. Ice water was added. The mixture was extracted with CH$_2$Cl$_2$ and separated into its layers. The aqueous layer was washed twice with CH$_2$Cl$_2$. The combined organic layer was dried (MgSO$_4$), filtered and the solvent was evaporated. The residue was taken up in diethyl ether. The precipitate was filtered off and dried, yielding 1 g of (±)-N-[1-[1-(aminomethyl)-2-methylpropyl] 4-piperidinyl]-1-[ethoxy(8-quinolinyl)methyl]-1H-benzimidazol-2-amine; mp. 202° C. (comp. 100).

Example B5

Intermediate (32) (0.1382 mol) was added at 55° C. to a mixture of (±)-1-[ethoxy(3-methoxy-2-quinolinyl)methyl]-N-(4-piperidinyl)-1H-benzimidazol-2-amine (0.0346 mol) and potassium carbonate (0.242 mol) in acetonitrile (108 ml) and DMF (20 ml) (1 equiv of intermediate (32) was added every hour). The mixture was stirred at 55° C. for 1 hour and filtered. The filtrate was poured out into H$_2$O and the mixture was extracted with EtOAc. The organic layer was separated, washed with a saturated NaCl solution, dried (MgSO$_4$), filtered and the solvent was evaporated. The residue was purified by column chromatography over silica gel (eluent: CH$_2$Cl$_2$/CH$_3$OH/NH$_4$OH 98/2/0.4 and 96/4/0.5; 20-45 µm). Two fractions were collected and their solvents were evaporated, yielding 2.5 g (23%) of (±)-1,1-dimethylethyl [1-[[4-[[1-[ethoxy(3-methoxy-2-quinolinyl)methyl]-1H-benzimidazol-2-yl]amino]-1-piperidinyl]methyl]-2-methylpropyl] carbamate (comp. 38).

Example B6

A mixture of 1-[4-[[1-(2-quinolinylmethyl)-1H-benzimidazol-2-yl]amino]-1-piperidinyl]-3-methyl-2-butanone (0.0158 mol) and benzenemethanamine (0.0474 mol) in methanol (150 ml) was hydrogenated at 40° C. under a 3 bar pressure for 48 hours with palladium on activated carbon (0.7 g) as a catalyst. After uptake of hydrogen (1 equiv), the catalyst was filtered through celite, washed with CH$_2$Cl$_2$/CH$_3$OH and the filtrate was evaporated. The residue (11.5 g) was purified by column chromatography over silica gel (eluent: CH$_2$Cl$_2$/CH$_3$OH/NH$_4$OH 94/6/0.5; 20-45 µm). The pure fractions were collected and the solvent was evaporated, yielding 4 g of residue. This fraction was converted into the hydrochloric acid salt with 2-propanol/HCl. The precipitate was filtered off and dried, yielding 5.1 g of product. This fraction was converted into the free base and then purified by column chromatography over C$_{18}$ (eluent: CH$_3$OH/NH$_4$OAc 60/40 and 80/20; column: KROMASIL C18). Two pure fractions were collected and their solvents were evaporated, yielding 0.8 g of fraction 1 and 2 g of fraction 2. Fraction 1 was crystallized from diethyl ether. The precipitate was filtered off and dried, yielding 0.5 g of (±)-N-[1-(2-amino-3-methylbutyl)-4-piperidinyl]-1-(2-quinolinylmethyl)-1H-benzimidazol-2-amine; mp. 135° C. (comp. 6). Fraction 2 was dissolved in 2-propanol and converted into the hydrochloric acid salt (1:4). The precipitate was filtered off and dried, yielding 2.2 g of (±)-N-[1-(2-amino-3-methylbutyl)-4-piperidinyl]-1-[(1,2,3,4-tetrahydro-2-quinolinyl)methyl]-1H-benzimidazol-2-amine tetrahydrochloride monohydrate; mp. 230° C. (comp. 46).

Example B7 a) A dispersion of sodium hydride in a mineral oil (60%) (0.01 mol) was added portionwise at 0° C. under N$_2$ flow to a mixture of intermediate (38) (0.005 mol) in DMF (25 ml). The mixture was stirred at room temperature for 1 hour. A solution of 2-(bromomethyl)-3-methoxyquinoline (0.0055 mol) in DMF (10 ml) was added dropwise. The mixture was stirred at room temperature for 2 hours, hydrolized with K$_2$CO$_3$ 10% and extracted with EtOAc. The organic layer was separated, washed with NaCl, dried (MgSO$_4$), filtered and the solvent was evaporated, yielding 4.5 g (>100%) of (±)-1,1-dimethylethyl [1-[[4-[[1-[(3-methoxy-2-quinolinyl)methyl]-1H-benzimidazol-2-yl]-amino]-1-piperidinyl]methyl]-2-methylpropyl]carbamate (comp. 14).

b) A dispersion of sodium hydride in a mineral oil (60%) (0.014 mol) was added portionwise at 0° C. under N$_2$ flow to a mixture of intermediate (38) (0.007 mol) in DMF (30 ml). The mixture was stirred at 5° C. for 1 hour. A solution of (±)-2,8-di-bromo-5,6,7,8-tetrahydroquinoline (0.0084 mol) in DMF (10 ml) was added dropwise. The mixture was stirred at room temperature for 2 hours. H$_2$O and EtOAc were added. The organic layer was separated, washed with a saturated NaCl solution, dried (MgSO$_4$), filtered and the solvent was evaporated. The residue (5.6 g) was purified by column chromatography over silica gel (eluent: CH$_2$Cl$_2$/CH$_3$OH/NH$_4$OH 97/3/0.5; 20-45 μm). The pure fractions were collected and the solvent was evaporated, yielding 1.1 g (25%) of (±)-1,1-dimethylethyl [1-[[4-[[1-(2-bromo-5,6,7,8-tetrahydro-8-quinolinyl)-1H-benzimidazol-2-yl]amino]-1-piperidinyl]methyl]-2-methylpropyl]-carbamate (comp. 55).

c) A mixture of intermediate 84 (0.0145 mol), 8-bromomethylquinoline (0.0174 mol) and K$_2$CO$_3$ (0.029 mol) in CH$_3$N (70 ml) was stirred and refluxed for 4 hours, then brought to room temperature. The solvent was evaporated. The residue was taken up in H$_2$O and extracted twice with CH$_2$Cl$_2$. The organic layer was separated, dried (MgSO$_4$), filtered and the solvent was evaporated. The residue was crystallized from diethyl ether/CH$_3$CN. The precipitate was filtered off and dried, yielding 5.07 g of compound 79 (74%).

Example B8 c) (±)-N-[1-(2-amino-3-methylbutyl)-4-piperidinyl]-1-[(5,6,7,8-tetrahydro-3-methoxy-2-quinolinyl)methyl]-1H-benzimidazol-2-amine tetrahydrochloride monohydrate (0.00218 mol) was basified with K$_2$CO$_3$ 10%. The mixture was extracted with CH$_2$Cl$_2$. The organic layer was separated, dried (MgSO$_4$), filtered and the solvent was evaporated, to give A'. A mixture of A' in dichloromethane (50 ml) was cooled to 0° C. A solution of tribromoborane in dichloromethane (0.01526 mol) was added dropwise. The mixture was stirred at room temperature overnight, poured out on ice, basified with a concentrated NH$_4$OH solution, decanted and extracted with CH$_2$Cl$_2$. The organic layer was separated, dried (MgSO$_4$), filtered and the solvent was evaporated. The residue (1.1 g) was purified by column chromatography over silica gel (eluent: CH$_2$Cl$_2$/CH$_3$OH/NH$_4$OH 90/10/0.5; 20-45 μm). The desired fractions were collected and the solvent was evaporated. The residue was converted into the hydrochloric acid salt (1:4) with HCl/2-propanol. The precipitate was filtered off and dried, yielding 0.5 g (37%) of (±)-N-[1-(2-amino-3-methylbutyl)-4-piperidinyl]-1-[(5,6,7,8-tetrahydro-3-hydroxy-2-quinolinyl)methyl]-1H-benzimidazol-2-amine tetrahydro-chloride monohydrate; mp. 240° C. (comp. 63).

Example B9 a) A mixture of compound 158 (0.0089 mol) in HCl 3N (40 ml) was stirred at 100° C. for 12 hours, then brought to room temperature and poured out on ice and NH$_4$OH. EtOAc was added. The precipitate was filtered off, washed with EtOAc and dried, yielding 2 g of compound 159.

b) A mixture of compound 168 (0.00895 mol) in HCl 3N (35 ml) was stirred at 100° C. for 24 hours. The solvent was evaporated. The residue was taken up in EtOAc. The mixture was basified with NH$_4$OH. The organic layer was separated, dried (MgSO$_4$), filtered and the solvent was evaporated. Part of this fraction (0.7 g) was crystallized from CH$_3$CN. The precipitate was filtered off and dried, yielding 0.3 g of compound 167.

c) A mixture of compound 176 (0.00373 mol) in HCl 3N (20 ml) was stirred at 100° C. for 12 hours, brought to room temperature, poured out on ice, basified with NH$_4$OH and extracted with EtOAc. The organic layer was separated, dried (MgSO$_4$), filtered and the solvent was evaporated. This fraction was dissolved in 2-propanol and converted into the hydrochloric acid salt (1:3). The precipitate was filtered off and dried, yielding 1.5 g of compound 173 (77%).

Example B10

A mixture of intermediate

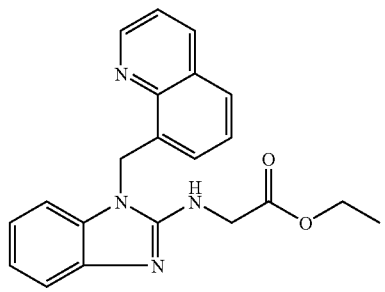

(interm. 87) (0.002 mol) (prepared according to A1b)), 1,2-ethanediamine (0.02 mol) and NaCN (0.0002 mol) in CH$_3$OH (7 ml) was heated at 45° C. for 4 hours and then brought to room temperature. Water was added. The mixture was extracted with CH$_2$Cl$_2$. The organic layer was separated, dried (MgSO$_4$), filtered and the solvent was evaporated. The residue (0.65 g) was purified by column chromatography over silica gel (eluent: CH$_2$Cl$_2$/CH$_3$OH/NH$_4$OH 90/10/1; 35-70 μm). The pure fractions were collected and the solvent was evaporated, yielding 0.42 g of compound 170 (56%)

Example B11

A mixture of intermediate

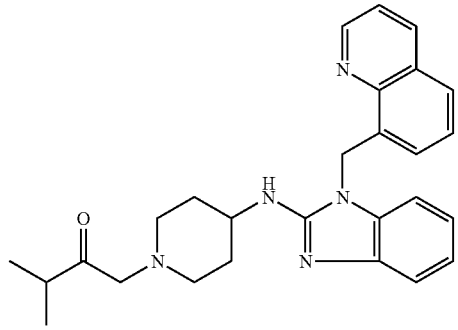

(interm. 88) (0.0077 mol) (prepared according to A14a)) and formic acid/NH$_3$ (0.0462 mol) in formamide (35 ml) was stirred at 140° C. for 30 min and then brought to room temperature. CH$_2$Cl$_2$ was added. The organic layer was separated, washed with K$_2$CO$_3$ 10%, dried (MgSO$_4$), filtered and the solvent was evaporated. The residue (4 g) was purified by column chromatography over silica gel (eluent: CH$_2$Cl$_2$/CH$_3$OH/NH$_4$OH 97/3/0.1; 15-40 μm). Two pure fractions were collected and their solvents were evaporated. The second fraction was crystallized from CH$_3$CN and diethyl ether. The precipitate was filtered off and dried, yielding: 1.37 g of compound 137 (46%).

Example B12

Isopropyl titanate (IV) (0.0294 mol) was added at room temperature to a mixture of intermediate 85 (0.0245 mol) and 1-acetylpiperazine (0.027 mol) in $CH_2Cl_2$ (50 ml) and ethanol (50 ml). The mixture was stirred at room temperature for 7 hours. $NaBH_3CN$ (0.0245 mol) was added portionwise. The mixture was stirred at room temperature for 12 hours. $H_2O$ was added. The mixture was filtered over celite and washed with $CH_2Cl_2$. The filtrate was separated into its layers. The organic layer was dried ($MgSO_4$), filtered and the solvent was evaporated. The residue (6.7 g) was purified by column chromotography over silica gel (eluent: $CH_2Cl_2/CH_3OH/NH_4OH$ 95/5/0.2; 15-40 μm). The pure fractions were collected and the solvent was evaporated. This fraction was crystallized from 2-propanone. The precipitate was filtered off and dried, yielding: 0.64 g of compound 176.

Tables 4 to 13 list the compounds of formula (I) which were prepared according to one above examples.

TABLE 4

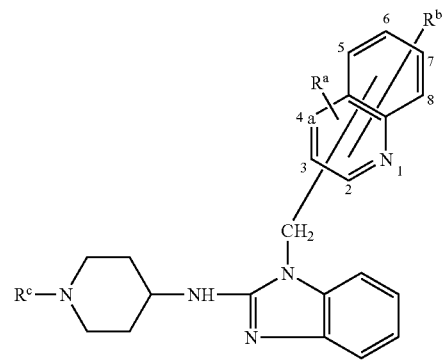

| Comp No. | Ex. No. | a | $R^a$ | $R^b$ | * | $R^c$ | Physical data |
|---|---|---|---|---|---|---|---|
| 1 | B1a | CH | H | H | 2 | H | HCl (1:2) |
| 2 | B1b | CH | H | H | 2 | ** | |
| 3 | B1c | CH | H | H | 2 | $CH_2CH_2NH_2$ | HCl(1:4); $H_2O$(1:1) |
| 4 | B1a | CH | H | H | 8 | H | |
| 5 | B1a | CH | H | H | 2 | H | |
| 6 | B5 | CH | H | H | 2 | $CH_2CH$(2-propyl)$NH_2$ | |
| 7 | B3 | CH | H | H | 8 | $CH$(2-propyl)$CH_2NH_2$ | |
| 8 | B3 | CH | H | H | 2 | $CH$(2-propyl)$CH_2NH_2$ | $H_2O$ (1:1) |
| 9 | B1a | CH | H | 8-Cl | 2 | H | HCl (1:2) |
| 10 | B1c | CH | H | H | 8 | $CH_2CH$(2-propyl)$NH_2$ | |
| 11 | B3 | CH | H | 8-Cl | 2 | $CH$(2-propyl)$CH_2NH_2$ | |
| 12 | B1a | CH | 4-OH | H | 2 | H | |
| 13 | B3 | CH | H | 8-Cl | 2 | $CH$(2-propyl)$CH_2NH_2$ | |
| 14 | B6a | CH | 3-$OCH_3$ | H | 2 | (C=O)OC($CH_3$)$_3$ | |
| 15 | B1c | CH | 3-$OCH_3$ | H | 2 | $CH_2CH$(2-propyl)$NH_2$ | |
| 16 | B6a | N | 3-$CH_3$ | H | 2 | *** | |
| 17 | B1a | CH | H | H | 8 | H | HCl (1:3) |
| 18 | B1a | N | H | H | 8 | H | |
| 19 | B1c | N | H | H | 8 | $CH_2CH$(2-propyl)$NH_2$ | HCl(1:3); $H_2O$(1:3) |
| 20 | B1a | N | 3-$OCH_3$ | H | 2 | H | |
| 21 | B4 | N | 3-$OCH_3$ | H | 2 | *** | |
| 22 | B1c | N | 3-$OCH_3$ | H | 2 | $CH_2CH$(2-propyl)$NH_2$ | |
| 23 | B1a | CH | H | H | 4 | H | |
| 24 | B2 | CH | H | H | 4 | $CH_2CH_2NH_2$ | |
| 88 | B1a | N | 2-$CH_3$ | 3-$CH_3$ | 8 | H | |
| 89 | B1c | N | 2-$CH_3$ | 3-$CH_3$ | 8 | $CH_2CH$(2-propyl)$NH_2$ | HCl(1:4); $H_2O$(1:2) |
| 90 | B1a | CH | 2-$CH_3$ | H | 8 | H | |
| 91 | B1c | CH | 2-$CH_3$ | H | 8 | $CH_2CH$(2-propyl)$NH_2$ | $H_2O$ (1:1) |
| 92 | B2 | CH | 2-$CH_3$ | H | 8 | $CH_2CH_2NH_2$ | |
| 104 | B3 | CH | H | H | 8 | $CH_2CH$(2-propyl)$NH_2$ | |
| 105 | B3 | CH | H | H | 8 | $CH$(2-propyl)$CH_2NH_2$ | |
| 106 | B1c | N | 3-$CH_3$ | H | 2 | $CH_2CH$(2-propyl)$NH_2$ | $H_2O$ (1:2) |
| 109 | B5 | CH | H | H | 8 | *** | |
| 110 | B5 | N | 2-$CH_3$ | 3-$CH_3$ | 8 | *** | |
| 111 | B5 | CH | 2-$CH_3$ | H | 8 | *** | |
| 112 | B5 | N | H | H | 8 | *** | |
| 113 | B7 | CH | H | H | 8 | *** | |

* position bicyclic heterocycle
** $(CH_2)_2NH(C=O)OC(CH_3)_3$
*** $CH_2CH$(2-propyl)$NH(C=O)OC(CH_3)_3$

TABLE 5

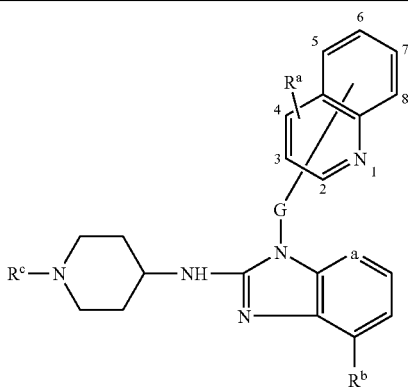

| Comp No. | Ex. No. | a | Rª | Rᵇ | * | Rᶜ | G | Physical data |
|---|---|---|---|---|---|---|---|---|
| 25 | B1a | CH | H | H | 2 | H | CHOC$_2$H$_5$ | |
| 26 | B3 | CH | H | H | 2 | CH(2-propyl)CH$_2$NH$_2$ | CHOC$_2$H$_5$ | H$_2$O (1:1) |
| 27 | B3 | CH | H | H | 2 | CH$_2$CH(2-propyl)NH$_2$ | CHOC$_2$H$_5$ | |
| 28 | B1a | CH | H | H | 2 | H | *** | |
| 29 | B3 | CH | H | H | 2 | CH(2-propyl)CH$_2$NH$_2$ | *** | H$_2$O (1:1) |
| 30 | B1a | CH | H | H | 8 | H | *** | |
| 31 | B3 | CH | H | H | 8 | CH$_2$CH(2-propyl)NH$_2$ | *** | |
| 32 | B3 | CH | H | H | 8 | CH(2-propyl)CH$_2$NH$_2$ | *** | |
| 33 | B1a | CH | H | H | 8 | H | CHOC$_2$H$_5$ | |
| 34 | B1a | CH | 3-OCH$_3$ | H | 2 | H | CHOC$_2$H$_5$ | |
| 35 | B1a | N | H | H | 2 | H | CH$_2$ | |
| 36 | B4 | N | H | H | 2 | ** | CH$_2$ | |
| 37 | B1c | N | H | H | 2 | CH$_2$CH(2-propyl)NH$_2$ | CH$_2$ | HCl (1:4) |
| 38 | B4 | CH | 3-OCH$_3$ | H | 2 | ** | CHOC$_2$H$_5$ | |
| 39⁽⁹⁾ | B1c | CH | 3-OCH$_3$ | H | 2 | CH$_2$CH(2-propyl)NH$_2$ | CHOC$_2$H$_5$ | HCl (1:3); H$_2$O (1:2) |
| 40 | B2 | N | H | H | 2 | CH$_2$CH$_2$NH$_2$ | CH$_2$ | |
| 41 | B1a | N | H | H | 8 | H | CH$_2$ | |
| 42 | B1c | N | H | H | 8 | CH$_2$CH(2-propyl)NH$_2$ | CH$_2$ | |
| 43 | B1a | CH | H | CH$_3$ | 8 | H | CH$_2$ | |
| 44 | B1a | CH | H | CH$_3$ | 8 | H | CHOC$_2$H$_5$ | |
| 45 | B2 | N | H | H | 8 | CH$_2$CH$_2$NH$_2$ | CH$_2$ | |
| 100 | B3 | CH | H | H | 8 | CH(2-propyl)CH$_2$NH$_2$ | CHOC$_2$H$_5$ | |
| 107 | B1c | CH | H | H | 8 | CH$_2$CH(2-propyl)NH$_2$ | CHOC$_2$H$_5$ | |
| 115 | B5 | CH | H | CH$_3$ | 8 | CH(CH$_3$)$_2$ CH$_2$CH$_3$ with NHC(=O)OC(CH$_3$)$_3$ | CH$_2$ | |
| 116 | B1d | CH | H | CH$_3$ | 8 | CH$_2$CH(2-propyl)NH$_2$ | CH$_2$ | |
| 117 | B1d | CH | H | CH$_3$ | 8 | CH=O | CH$_2$ | |
| 118 | B1d | CH | H | CH$_3$ | 8 | CH$_2$CH$_2$NH$_2$ | *** | H$_2$O(1:1) |
| 119 | B1d | CH | H | CH$_3$ | 8 | CH$_2$CH(2-propyl)NH$_2$ | *** | |
| 120 | B3 | N | H | CH$_3$ | 8 | CH$_2$CH$_2$NH$_2$ | CH$_2$ | HCl(1:4); H$_2$O(1:3) |
| 121 | B1d | CH | H | CH$_3$ | 8 | CH=O | *** | |
| 122 | B1c | N | H | CH$_3$ | 8 | CH$_2$CH(2-propyl)NH$_2$ | CH$_2$ | HCl(1:4); H$_2$O(1:1) |
| 123 | B1d | CH | H | CH$_3$ | 8 | CH$_2$CH$_2$NH$_2$ | CH$_2$ | |
| 124 | B1c | CH | H | H | 8 | CH$_2$CH$_2$NH$_2$ | *** | HCl(1:3); H$_2$O(1:2) |
| 125 | B1c | CH | H | CH$_3$ | 8 | CH$_2$CH$_2$NH$_2$ | CHCH$_3$ | H$_2$O(1:1) |
| 126 | B1d | CH | 3-OCH$_3$ | H | 2 | CH$_2$CH$_2$NH$_2$ | CH$_2$ | H$_2$O(1:2) |
| 127 | B1c | CH | 4-CH$_3$ | H | 2 | CH$_2$CH(2-propyl)NH$_2$ | CH$_2$ | HCl(1:4); H$_2$O(1:1) |
| 128 | B1c | CH | H | H | 8 | CH$_2$CH$_2$NH$_2$ | CH$_2$ | HCl(1:4); H$_2$O(1:1) |
| 129 | B1c | CH | H | H | 8 | CH$_2$CH$_2$NH$_2$ | CHCH$_3$ | H$_2$O(1:1) |
| 130 | B1c | CH | 4-CH$_3$ | H | 2 | CH$_2$CH$_2$NH$_2$ | CH$_2$ | HCl(1:4); H$_2$O(1:2) |
| 131 | B1c | CH | H | H | 4 | CH$_2$CH(2-propyl)NH$_2$ | CH$_2$ | HCl(1:4); H$_2$O(1:2) |

TABLE 5-continued

| Comp. No. | Ex. No. | a | R$^a$ | R$^b$ | * | R$^c$ | G | Physical data |
|---|---|---|---|---|---|---|---|---|
| 131 | B1b | CH | H | CH$_3$ | 8 | ethyl-NH-C(=O)-O-C(CH$_3$)$_3$ | CH$_2$ | |
| 132 | B1b | CH | H | H | 8 | ethyl-NH-C(=O)-O-C(CH$_3$)$_3$ | CH$_2$ | |
| 133 | B2 | CH | H | H | 8 | H | CHCH$_3$ | HCl(1:2); H$_2$O(1:2) |
| 134 | B1c | CH | H | H | 2 | CH$_2$CH$_2$NH$_2$ | CHCH$_3$ | H$_2$O(1:1) |
| 135 | B2 | CH | 4-CH$_3$ | H | 2 | H | CH$_2$ | HCl(1:2) |
| 136 | B2 | N | H | CH$_3$ | 8 | H | CH$_2$ | |
| 137 | B11 | CH | H | H | 8 | CH=O | CH$_2$ | |

* position quinoline
** CH$_2$CH(2-propyl)NH(C=O)OC(CH$_3$)$_3$
*** CHO(CH$_2$)$_2$OC$_2$H$_5$

TABLE 6

| Comp. No. | Ex. No. | * | G | R$^a$ | Physical data |
|---|---|---|---|---|---|
| 46 | B5 | 2 | CH$_2$ | CH$_2$CH(2-propyl)NH$_2$ | HCl(1:4); H$_2$O(1:1) |
| 47 | B5 | 8 | CH$_2$ | CH$_2$CH(2-propyl)NH$_2$ | HCl(1:4); H$_2$O(1:1) |
| 48 | B5 | 8 | — | H | |
| 49 | B5 | 8 | — | CH$_2$CH(2-propyl)NH$_2$ | H$_2$O (1:1) |

* position bicyclic heterocycle

TABLE 7

| Co. No. | Ex. No. | * | a | Ra | G | R^b | R^c | Physical data |
|---|---|---|---|---|---|---|---|---|
| 50 | B1a | 8 | CH | H | — | H | H | |
| 51 | B5 | 8 | CH | H | — | CH$_2$CH(2-propyl)NH$_2$ | H | |
| 52 | B1a | 8 | N | H | — | H | H | HCl (1:3) |
| 53 | B3 | 8 | N | H | — | CH(2-propyl)CH$_2$NH$_2$ | H | |
| 54(3) | B3 | 8 | N | H | — | CH$_2$CH(2-propyl)NH$_2$ | H | H$_2$O (1:1) |
| 55 | B6b | 8 | CH | 2-Br | — | ** | H | |
| 56 | B1c | 8 | CH | 2-Br | — | CH$_2$CH(2-propyl)NH$_2$ | H | HCl(1:3); H$_2$O(1:3) |
| 57 | B6b | 8 | CH | 2-CH$_3$ | — | ** | H | |
| 58 | B1c | 8 | CH | 2-CH$_3$ | — | CH$_2$CH(2-propyl)NH$_2$ | H | HCl(1:4); H$_2$O(1:1) |
| 59 | B6a | 2 | CH | H | CH$_2$ | ** | H | |
| 60 | B1c | 2 | CH | H | CH$_2$ | CH$_2$CH(2-propyl)NH$_2$ | H | HCl(1:4); H$_2$O(1:1) |
| 61 | B6a | 2 | CH | 3-OCH | CH$_2$ | ** | H | |
| 62 | B1c | 2 | CH | 3-OCH | CH$_2$ | CH$_2$CH(2-propyl)NH$_2$ | H | HCl(1:4); H$_2$O(1:1) |
| 63 | B7 | 2 | CH | 3-OH | CH$_2$ | CH$_2$CH(2-propyl)NH$_2$ | H | HCl(1:4); H$_2$O(1:1) |
| 64 | B1a | 8 | N | 3-Cl | — | H | H | |
| 65 | B4 | 8 | N | 3-Cl | — | ** | H | |
| 66 | B1c | 8 | N | 3-Cl | — | CH$_2$CH(2-propyl)NH$_2$ | H | HCl(1:3); H$_2$O(1:1) |
| 67 | B2 | 8 | N | H | — | CH$_2$CH$_2$NH$_2$ | H | HCl(1:3); H$_2$O(1:3) |
| 68 | B1a | 8 | N | 2-Cl | — | H | H | |
| 69 | B4 | 8 | N | 2-Cl | — | ** | H | |
| 70(10) | B1c | 8 | N | 2-Cl | — | CH$_2$CH(2-propyl)NH$_2$ | H | HCl(1:3); H$_2$O(1:1) |
| 139 | B1c | 5 | N | 3-Cl | — | CH$_2$CH$_2$NH$_2$ | CH$_3$ | HCl(1:3); H$_2$O(1:2) |
| 140 | B1d | 5 | N | H | — | CH$_2$CH(2-propyl)NH$_2$ | CH$_3$ | |
| 141 | B1c | 5 | N | 2-Cl | — | CH$_2$CH$_2$NH$_2$ | CH$_3$ | HCl(1:3); H$_2$O(1:3) |
| 142 | B1c | 5 | N | 2-Cl | — | CH$_2$CH(2-propyl)NH$_2$ | CH$_3$ | |

* position bicyclic heterocycle
** CH$_2$CH(2-propyl)NH(C=O)OC(CH$_3$)$_3$

TABLE 8

| Comp. No | Ex. No. | a | b | R^a | R^b | G | R^c | Physical data |
|---|---|---|---|---|---|---|---|---|
| 71 | | N | N | H | H | — | H | |
| 72 | | S | N | — | H | — | H | HBr(1:2); H$_2$O(2:1) |

TABLE 8-continued
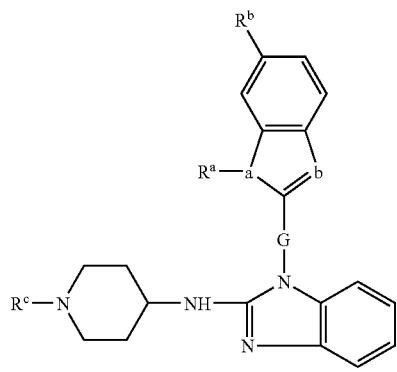
| Comp. No | Ex. No. | a | b | Rª | Rᵇ | G | Rᶜ | Physical data |
|---|---|---|---|---|---|---|---|---|
| 73 | B1a | O | N | — | H | — | H | |
| 74 | | N | N | H | H | CH₂ | H | |
| 75 | | N | N | H | H | CH₂ | CH₂CH₂NH₂ | H₂O (1:1) |
| 76 | | O | CH | — | H | CH₂ | H | |
| 77 | | N | N | CH₃ | H | CH₂ | H | |
| 78 | B1c | N | N | CH₃ | H | CH₂ | CH₂CH₂NH₂ | |
| 79 | | S | CH | — | H | CH₂ | H | |
| 80 | B1a | S | N | — | H | CH₂ | H | HCl(1:2); H₂O(1:1) |
| 81 | B2 | N | N | H | H | — | CH₂CH₂NH₂ | HCl(1:4) |
| 82 | B1a | N | N | H | OCH₃ | CH₂ | H | |
| 83 | B1b | S | N | — | H | — | * | H₂O (1:1) |
| 84 | B1c | S | N | — | H | — | CH₂CH₂NH₂ | HCl(1:3); H₂O(1:1) |
| 85 | B1b | N | N | CH₃ | H | CH₂ | * | |
| 86 | B1b | O | N | — | H | — | * | |
| 87 | B1c | O | N | — | H | — | CH₂CH₂NH₂ | |
* CH₂CH₂NH(C=O)OC(CH₃)₃
TABLE 9
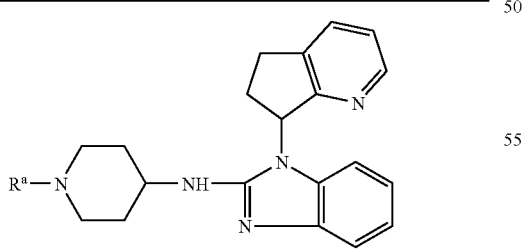
| Comp. No. | Ex. No. | Rª | Physical data |
|---|---|---|---|
| 102 | B1a | H | HCl (1:3) |
| 103 | B5 | CH₂CH(2-propyl)NH₂ | H₂O (1:1) |

TABLE 10
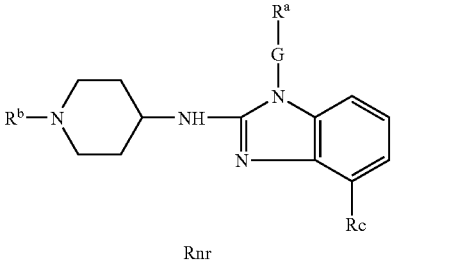
Rnr
| Comp. No. | Ex. No. | R<sup>b</sup> | R<sup>c</sup> | G-R<sup>a</sup> | Physical data |
|---|---|---|---|---|---|
| 93 | | H | H | 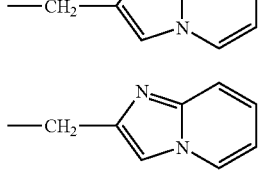 | |
| 101 | | CH₂CH₂NH₂ | H | | |
| 94 | | CH₂CH₂NH(C=O)OCH₂CH₃ | H | 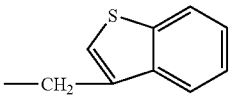 | |
| 95 | | CH₂CH₂NH₂ | H | | |
| 96 | B1a | H | H | 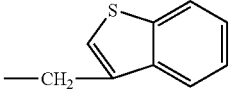 | |
| 97 | B2 | CH₂CH₂NH₂ | H | 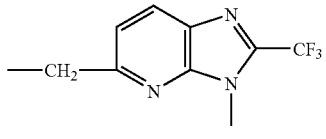 | HCl(1:3); H₂O(1:1) |
| 98 | B1a | H | H | 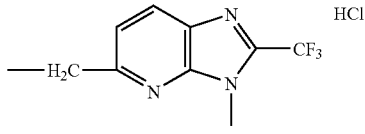 | |
| 99 | B1c | CH₂CH(2-propyl)NH₂ | H | 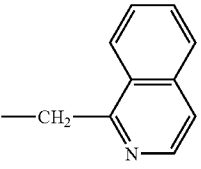 | HCl(1:3); H₂O(1:3) |
| 108 | B5 | CH₂CH(2-propyl)NH₂ | H | 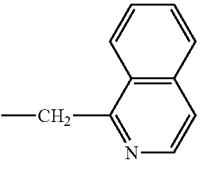 | |

TABLE 10-continued

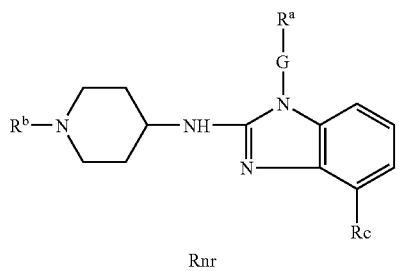

Rnr

| Comp. No. | Ex. No. | $R^b$ | $R^c$ | G-$R^a$ | Physical data |
|---|---|---|---|---|---|
| 114 | | * | H | —CH$_2$-(1-isoquinolinyl) | |
| 143 | B6 | CH$_2$CH(2-propyl)NH$_2$ | CH$_3$ | —H$_2$C-(1-methylbenzimidazol-4-yl) | |

* CH$_2$CH(2-propyl)NH(C=O)OC(CH$_3$)$_3$

TABLE 11

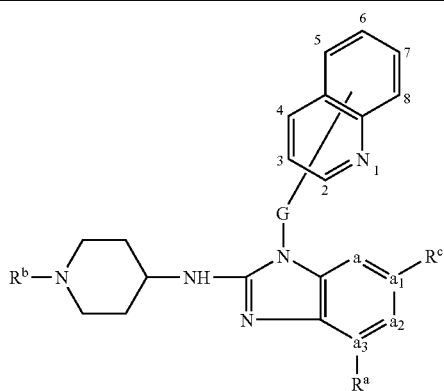

| Co No. | Ex. No. | a-a1-a2-a3 | * | $R^a$ | $R^c$ | $R^b$ | G | Physical data |
|---|---|---|---|---|---|---|---|---|
| 144 | B1c | CH=N—CH=C | 8 | H | — | CH$_2$CH(2-propyl)NH$_2$ | CH$_2$ | HCl(1:3); H$_2$O(1:4) |
| 145 | B1c | CH=C—N=C | 8 | H | H | CH$_2$CH(2-propyl)NH$_2$ | CH$_2$ | HCl(1:3); H$_2$O(1:2) |
| 146 | B1c | CH=C—C=N | 8 | — | H | CH$_2$CH(2-propyl)NH$_2$ | CH$_2$ | HCl(1:3); H$_2$O(1:2) |
| 147 | B2 | CH=C—CH=C | 8 | CH$_3$ | Cl | H | CH$_2$ | |
| 148 | B3 | CH=N—CH=C | 8 | H | — | CH$_2$CH$_2$NH$_2$ | CHOC$_2$H$_5$ | |
| 149 | B2 | CH=C—C=N | 8 | — | H | H | CH$_2$ | HCl(1:2); H$_2$O(1:1) |
| 150 | B1c | CH=C—CH=C | 7 | CH$_3$ | Cl | CH$_2$CH$_2$NH$_2$ | CH$_2$ | HCl(1:4); H$_2$O(1:2) |
| 151 | B3 | CH=N—CH=C | 8 | H | — | CH$_2$CH$_2$NH$_2$ | CH$_2$ | |
| 152 | B2 | CH=N—CH=C | 8 | H | — | H | CH$_2$ | HCl(1:4); H$_2$O(1:2) |
| 153 | B3 | CH=C—CH=N | 8 | — | H | CH$_2$CH$_2$NH$_2$ | CHOC$_2$H$_5$ | |

* position bicyclic heterocycle

TABLE 12
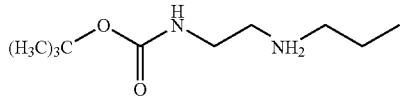
| Co No. | Ex. No. | R$^a$ | R$^b$ | Physical data |
|---|---|---|---|---|
| 154 | B1c | H | 3-propylamine | HCl(1:3); H$_2$O(1:1) |
| 155 | B1b | H | 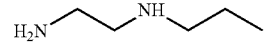 | |
| 156 | B1e | H | 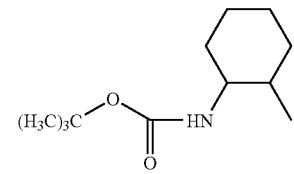 | |
| 157 | B7c | H | 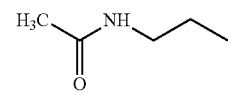 | trans |
| 158 | B7c | H | 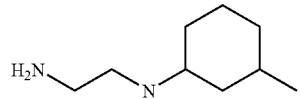 | |
| 159 | B9a | H | 2-ethylamine | |
| 160 | B1c | H | 3-propylmethylamine | |
| 161 | B1c | H | 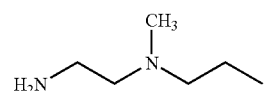 | cis; HCl(1:3); H$_2$O(1:1) |
| 162 | B1c | H |  | HCl(1:4); H$_2$O(1:1) |
| 163 | B4 | H | 3-isobutylamine | |
| 164 | B1c | H | 2-ethylmethylamine | HCl(1:2) |
| 165 | B1a | H | 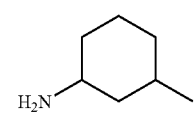 | trans; H$_2$O(1:1) |
| 166 | B9a | CH$_3$ | 2-ethylamine | |
| 167 | B9b | H |  | cis |

TABLE 12-continued

[Structure: quinoline (numbered 1-8) with CH2 linker at position 8 connecting to N1 of a benzimidazole; benzimidazole has NHRb at position 2 and Ra at position 4]

| Co No. | Ex. No. | Rª | Rᵇ | Physical data |
|---|---|---|---|---|
| 168 | B7c | H | [3-methylcyclohexyl-NH-C(O)-CH3] | cis |
| 169 | B3 | H | H2N-CH2CH2-N(CH3)-C(O)-CH2- | HCl(1:3); H2O(1:2) |
| 170 | B10 | H | H2N-CH2CH2-NH-C(O)-CH2- | |
| 171 | B10 | H | H2N-CH2CH2-NH-C(O)-CH(CH(CH3)2)- | H2O(1:1) |
| 172 | B1c | H | H2N-CH2CH2-N(piperazine)N-CH2- | HCl(1:4); H2O(1:2) |
| 173 | B9c | H | HN(piperazine)N-CH2- | HCl(1:3) H2O(1:2) |
| 174 | B1c | H | H2N-CH2CH2-N(piperazine)N-CH2-CH(CH3)- | |
| 175 | B7c | H | (H3C)3C-O-C(O)-NH-(2-methylcyclohexyl)- | cis |
| 176 | B12 | H | H2N-CH2CH2-N(piperazine)N-CH2-CH(CH3)- | |

TABLE 13

| Co No. | Ex. No. | G | L | a. | Ra. | Physical data |
|---|---|---|---|---|---|---|
| 177 | B1d | 2-ethylamine | 5,6,7,8-tetrahydro-2,3-dimethyl-8-methylquinoxaline | CH | H | HCl(1:3); H₂O(1:3) |
| 178 | B1c | 2-ethylamine | 1,7-dimethyl-1H-benzimidazole | N | H | HCl(1:4); H₂O(1:4) |
| 179 | B1c | 2-ethylamine | 5,6,7,8-tetrahydro-2,3-dimethyl-8-methylquinoxaline | CH | CH3 | H₂O(1:1) |
| 180 | B1b | (H₃C)₃C-O-C(O)-NH-CH₂- | 5,6,7,8-tetrahydro-2,3-dimethyl-8-methylquinoxaline | CH | H | |
| 181 | B1c | CH(CH₃)₂, H₂N-CH-CH₂- | 3-methylquinoxaline | CH | H | HCl(1:3); H₂O(1:2) |
| 182 | B1c | 2-ethylamine | 8-methyl-2(1H)-quinolinone | CH | H | HCl(1:3); H₂O(1:2) |
| 183 | B1c | 2-ethylamine | 2-methyl-1,8-naphthyridine | CH | H | |
| 184 | B1c | 2-ethylamine | 3-methylimidazo[1,2-a]pyridine | CH | H | HCl(1:4); H₂O(1:1) |
| 185 | B1d | 2-ethylamine | 3-methyl-2,3-dihydro-1,4-dioxino[2,3-b]pyridine | CH | H | C₂H₂O₄(2:7) |

TABLE 14

| Comp. No. | C Theor. | C Exp. | H Theor. | H Exp. | N Theor. | N Exp. | melting point |
|---|---|---|---|---|---|---|---|
| 1 | 61.40 | 60.70 | 5.85 | 6.04 | 16.27 | 15.54 | |
| 3 | 51.08 | 51.16 | 6.07 | 6.35 | 14.89 | 14.17 | |
| 4 | 73.92 | 73.29 | 6.49 | 6.52 | 19.59 | 19.38 | 206° C. |
| 6 | 73.27 | 73.12 | 7.74 | 7.73 | 18.99 | 18.77 | 135° C. |
| 7 | 73.27 | 71.85 | 7.74 | 7.80 | 18.99 | 18.61 | 188° C. |
| 8 | 70.40 | 69.73 | 7.88 | 7.40 | 18.24 | 17.56 | 80° C. |
| 9 | | | | | | | >250° C. |
| 10 | 73.27 | 72.82 | 7.74 | 7.58 | 18.99 | 18.63 | 172° C. |
| 11 | | | | | | | 190° C. |
| 13 | 67.98 | 66.43 | 6.97 | 6.79 | 17.62 | 17.02 | 164° C. |
| 15 | 71.16 | 70.66 | 7.68 | 7.58 | 17.78 | 17.81 | 210° C. |
| 19 | 51.45 | 51.64 | 6.97 | 6.89 | 16.15 | 15.96 | 240° C. |
| 22 | 68.47 | 68.04 | 7.45 | 7.52 | 20.70 | 20.55 | 206° C. |
| 23 | 73.92 | 71.70 | 6.49 | 6.53 | 19.59 | 19.92 | 140° C. |
| 24 | 71.97 | 69.89 | 7.05 | 7.10 | 20.98 | 20.07 | 196° C. |
| 89 | 51.46 | 53.22 | 6.94 | 7.11 | 15.00 | 15.14 | 24° C. |
| 91 | 70.85 | 69.82 | 8.07 | 8.29 | 17.71 | 17.48 | 180° C. |
| 92 | 72.43 | 71.51 | 7.29 | 7.30 | 20.27 | 20.10 | 176° C. |
| 104 | 72.87 | 70.26 | 7.53 | 7.27 | 19.61 | 18.73 | 88° C. |
| 105 | 72.87 | 71.37 | 7.53 | 7.39 | 19.61 | 19.39 | 135° C. |
| 106 | 65.69 | 66.19 | 7.96 | 7.62 | 19.86 | 19.71 | 110° C. |
| 26 | 69.02 | 69.16 | 7.99 | 7.68 | 16.65 | 16.79 | 140° C. |
| 27 | 71.57 | 70.60 | 7.87 | 7.80 | 17.27 | 17.14 | 166° C. |
| 29 | 67.86 | 67.64 | 8.08 | 7.79 | 15.32 | 15.15 | 100° C. |
| 31 | 70.16 | 68.97 | 7.98 | 7.97 | 15.84 | 15.56 | 110° C. |
| 32 | 70.16 | 69.35 | 7.98 | 8.34 | 15.84 | 14.73 | 98° C. |
| 33 | 71.79 | 70.72 | 6.78 | 7.17 | 17.44 | 16.69 | 145° C. |
| 37 | | | | | | | 215° C. |
| 39 | | | | | | | 209° C. |
| 40 | 68.80 | 66.01 | 6.78 | 6.60 | 24.42 | 23.31 | 138° C. |
| 42 | 70.40 | 69.14 | 7.50 | 7.50 | 22.10 | 21.68 | 180° C. |
| 43 | 74.36 | 73.02 | 6.78 | 6.65 | 18.85 | 18.41 | 155° C. |
| 44 | 72.26 | 71.53 | 7.03 | 7.26 | 16.85 | 16.40 | 186° C. |
| 45 | 68.80 | 66.74 | 6.78 | 6.64 | 24.42 | 23.77 | 178° C. |
| 100 | 71.57 | 71.16 | 7.87 | 7.93 | 17.27 | 17.44 | 202° C. |
| 107 | 71.57 | 69.77 | 7.87 | 7.85 | 17.27 | 16.40 | 78° C. |
| 46 | | | | | | | 230° C. |
| 47 | | | | | | | 230° C. |
| 48 | 72.59 | 71.54 | 7.25 | 7.13 | 20.16 | 19.91 | 205° C. |
| 49 | 69.30 | 70.08 | 8.50 | 8.37 | 18.65 | 18.93 | 140° C. |
| 51 | 72.19 | 70.66 | 8.39 | 8.43 | 19.43 | 18.79 | 120° C. |
| 53 | 69.25 | 68.88 | 8.14 | 8.28 | 22.61 | 22.23 | |
| 54 | 66.49 | 66.30 | 8.26 | 7.77 | 21.71 | 21.53 | 144° C. |
| 56 | 46.27 | 47.19 | 6.57 | 6.44 | 12.45 | 12.16 | >250° C. |
| 58 | | | | | | | 210° C. |
| 60 | | | | | | | 212° C. |
| 62 | 52.51 | 53.38 | 7.24 | 7.63 | 13.12 | 12.37 | 240° C. |
| 63 | 51.76 | 52.74 | 7.08 | 7.32 | 13.41 | 12.93 | 240° C. |
| 66 | 50.43 | 50.60 | 6.60 | 6.58 | 16.47 | 16.28 | >250° C. |
| 67 | 47.62 | 46.73 | 6.90 | 6.83 | 17.67 | 17.19 | 230° C. |
| 70 | | | | | | | 238° C. |
| 80 | | | | | | | 210° C. |
| 81 | 48.38 | 47.77 | 5.61 | 5.61 | | | |
| 82 | 67.00 | 66.51 | 6.43 | 6.29 | 22.32 | 22.12 | |
| 83 | 61.15 | 62.11 | 6.71 | 6.60 | 16.46 | 16.88 | |
| 84 | 48.51 | 48.46 | 5.62 | 5.35 | 16.16 | 16.03 | |
| 87 | 67.00 | 66.42 | 6.43 | 6.55 | 22.32 | 21.80 | |
| 103 | 68.78 | 68.77 | 8.31 | 8.23 | 19.25 | 18.78 | 88° C. |
| 96 | 58.73 | 58.59 | 5.16 | 5.03 | 22.83 | 22.40 | 144° C. |
| 97 | | | | | | | 210° C. |
| 99 | 53.51 | 52.63 | 7.15 | 7.02 | 13.87 | 13.24 | 200° C. |
| 108 | 70.08 | 68.99 | 7.92 | 8.10 | 22.00 | 21.65 | 160° C. |
| 116 | | | | | | | 203° C. |
| 117 | | | | | | | 218° C. |
| 141 | | | | | | | 225° C. |
| 177 | | | | | | | >260° C. |
| 139 | | | | | | | 190° C. |
| 118 | | | | | | | 48° C. |
| 144 | | | | | | | 220° C. |
| 143 | 70.55 | 66.03 | 8.11 | 8.14 | 21.33 | 18.98 | |
| 119 | | | | | | | 145° C. |
| 121 | | | | | | | 185° C. |
| 140 | | | | | | | 172° C. |
| 120 | | | | | | | 210° C. |
| 142 | | | | | | | 98° C. |
| 122 | | | | | | | 245° C. |
| 154 | | | | | | | 90° C. |
| 145 | | | | | | | 190° C. |
| 123 | | | | | | | 194° C. |
| 124 | | | | | | | 150° C. |
| 146 | | | | | | | 240° C. |
| 125 | | | | | | | 74° C. |
| 178 | | | | | | | 160° C. |
| 150 | | | | | | | >250° C. |
| 126 | | | | | | | 90° C. |
| 127 | | | | | | | 200° C. |
| 128 | | | | | | | 210° C. |
| 157 | | | | | | | 185° C. |
| 159 | | | | | | | 140° C. |
| 151 | | | | | | | 212° C. |
| 160 | 73.02 | 72.95 | 6.71 | 6.70 | 20.27 | 20.35 | |
| 129 | | | | | | | 170° C. |
| 130 | | | | | | | 150° C. |
| 131 | | | | | | | >250° C. |
| 152 | | | | | | | 230° C. |
| 153 | | | | | | | 169° C. |
| 131 | | | | | | | 120° C. |
| 161 | | | | | | | 206° C. |
| 132 | | | | | | | 160° C. |
| 133 | | | | | | | 210° C. |
| 134 | | | | | | | 81° C. |
| 162 | | | | | | | 210° C. |
| 147 | | | | | | | >250° C. |
| 163 | | | | | | | 168° C. |
| 179 | | | | | | | 116° C. |
| 135 | 62.16 | 62.10 | 6.12 | 6.06 | 15.76 | 15.71 | |
| 164 | | | | | | | 146° C. |
| 136 | | | | | | | 188° C. |
| 165 | | | | | | | 112° C. |
| 166 | | | | | | | 114° C. |
| 149 | | | | | | | 210° C. |
| 180 | | | | | | | 247° C. |
| 167 | | | | | | | 167° C. |
| 181 | | | | | | | 235° C. |
| 182 | | | | | | | >250° C. |
| 184 | 47.75 | 47.58 | 6.01 | 6.37 | 17.72 | 17.00 | |
| 169 | | | | | | | 180° C. |
| 170 | | | | | | | 73° C. |
| 171 | | | | | | | 72° C. |
| 172 | | | | | | | 178° C. |
| 173 | | | | | | | 190° C. |
| 137 | | | | | | | 196° C. |
| 175 | | | | | | | 228° C. |
| 176 | | | | | | | 168° C. |
| 185 | | | | | | | 158° C. |

C. Pharmacological Example

Example C1

In Vitro Screening for Activity Against Respiratory Syncytial Virus

The percent protection against cytopathology caused by viruses (antiviral activity or $IC_{50}$) achieved by tested compounds and their cytotoxicity ($CC_{50}$) were both calculated from dose-response curves. The selectivity of the antiviral effect is represented by the selectivity index (SI), calculated by dividing the $CC_{50}$ (cytotoxic dose for 50% of the cells) by the $IC_{50}$ (antiviral activity for 50% of the cells).

Automated tetrazolium-based calorimetric assays were used for determination of $IC_{50}$ and $CC_{50}$ of test compounds.

Flat-bottom, 96-well plastic microtiter trays were filled with 180 μl of Eagle's Basal Medium, supplemented with 5% FCS (0% for FLU) and 20 mM Herpes buffer. Subsequently, stock solutions (7.8×final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension ($4 \times 10^5$ cells/ml) of HeLa cells was added to all wells in a volume of 50 μl. The cultures were incubated at 37° C. in a 5% $CO_2$ atmosphere. Seven days after infection the cytotoxicity and the antiviral activity was examined spectrophotometrically. To each well of the microtiter tray, 25 μl of a solution of MIT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

Particular $IC_{50}$, $CC_{50}$ and SI values are listed in Table 15 hereinbelow.

TABLE 15

| Co. No. | $IC_{50}$ (μM) | $CC_{50}$ (μM) | SI |
|---------|----------------|----------------|-------|
| 42      | 0.0004         | >10.05         | >25119 |
| 31      | 0.0008         | 12.68          | 15849 |
| 56      | 0.0016         | 12.71          | 7943  |
| 145     | 0.00631        | 25.12          | 3981  |
| 6       | 0.0126         | 10.00          | 794   |
| 156     | 0.01259        | 19.95          | 1585  |
| 131     | 0.0316         | 19.94          | 631   |
| 53      | 0.1259         | >9.95          | >79   |
| 29      | 0.3162         | 10.12          | 32    |
| 148     | 1              | 25             | 25    |
| 97      | 1.5849         | >99.85         | >63   |

The invention claimed is:
1. A compound of formula

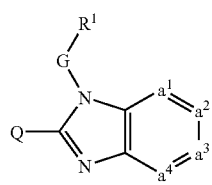
(I)

N-oxide, addition salt, quatemary amine, metal complex or stereochemically isomeric form thereof wherein $-a^1=a^2-a^3=a^4-$ represents a bivalent radical of formula —N=CH—CH=CH—  (a-2)

—CH=N—CH=CH—  (a-3);

—CH=CH—N=CH—  (a-4); or

—CH=CH—CH=N—  (a-5);

wherein each hydrogen atom in the radicals (a-2), (a-3), (a-4) and (a-5) may optionally be replaced by halo, $C_{1-6}$alkyl, nitro, amino, hydroxy, $C_{1-6}$alkyloxy, polyhalo$C_{1-6}$alkyl, carboxyl, amino$C_{1-6}$alkyl, mono- or di($C_{1-4}$alkyl)amino$C_{1-6}$alkyl, $C_{1-6}$alkyloxycarbonyl, hydroxy$C_{1-6}$alkyl, or a radical of formula

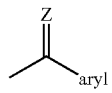

wherein =Z is =O, =CH—C(=O)—$NR^{5a}R^{5b}$, =$CH_2$, =CH—$C_{1-6}$alkyl, =N—OH or =N—O—$C_{1-6}$alkyl;
Q is a radical of formula

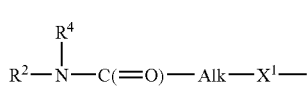
(b-1)

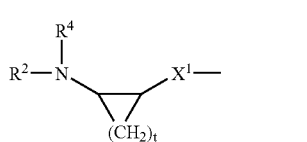
(b-2)

(b-3)

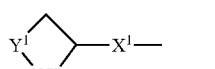

(b-4)

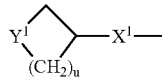

(b-5)

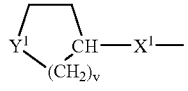

(b-6)

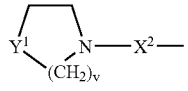

(b-7)

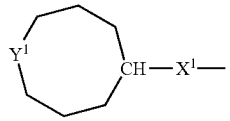

(b-8)

wherein
Alk is $C_{1-6}$alkanediyl;
$Y^1$ is a bivalent radical of formula $NR^2$- or $CH(NR^2R^4)$-;
$X^1$ is $NR^4$, S, S(=O), S(=O)$_2$, O, $CH_2$, C(=O), C(=$CH_2$), CH(OH), CH($CH_3$), CH($OCH_3$), CH($SCH_3$), CH($NR^{5a}R^{5b}$), $CH_2$—$NR^4$ or $NR^4$—$CH_2$;
$X^2$ is a direct bond, $CH_2$, C(=O), $NR^4$, $C_{1-4}$alkylene-$NR^4$, or $NR^4$-$C_{1-4}$alkylene;

t is 2, 3, 4 or 5;
u is 1, 2, 3, 4 or 5;
v is 2 or 3; and
whereby each hydrogen atom in Alk and the carbocycles and the heterocycles defined in radicals (b-3), (b-4), (b-5), (b-6), (b-7) and (b-8) may optionally be replaced by $R^3$; with the proviso that when $R^3$ is hydroxy or $C_{1-6}$alkyloxy, then $R^3$ can not replace a hydrogen atom in the α position relative to a nitrogen atom;

G is a direct bond or $C_{1-10}$alkanediyl optionally substituted with one, two or three substituents selected from hydroxy, $C_{1-6}$alkyloxy, aryl$C_{1-6}$alkyloxy, $C_{1-6}$alkylthio, aryl $C_{1-6}$alkylthio, arylcarbonyl, HO(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$—, amino, mono-or di($C_{1-6}$alkyl)amino, $C_{1-6}$alkyloxycarbonylamino and aryl;

$R^1$ is a bicyclic heterocycle selected from quinolinyl, quinoxalinyl, benzofuranyl, benzothienyl, benzimidazolyl, benzoxazolyl, benzthiazolyl, pyridopyridyl, naphthiridinyl, 1H-imidazo [4,5-b]pyridinyl, 3H-imidazo [4,5-b]pyridinyl, imidazo [1,2-a]pyridinyl, 2,3 -dihydro-1,4-dioxino [2,3-b]pyridyl or a radical of formula

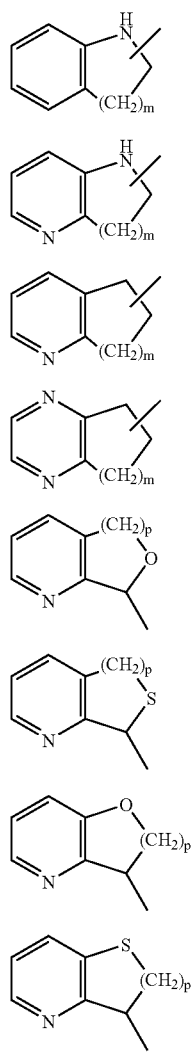

(c-1)

(c-2)

(c-3)

(c-4)

(c-5)

(c-6)

(c-7)

(c-8)

and said bicyclic heterocycles may optionally be substituted in either of the two cycles with 1 or where possible more substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl $C_{1-6}$alkyloxy, hydroxy$C_{1-6}$alkyl, mono-or di($C_{1-6}$alkyl)amino mono-or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{5c}$—, aryl-$SO_2$—$NR^{5c}$—, $C_{1-6}$alkyloxycarbonyl, —C(=O)—$NR^{5c}R^{5d}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$— and mono-or di($C_{1-6}$alkyl)amino(—$CH_2$—$CH_2$—O)$_n$—;

each n independently is 1, 2, 3 or 4;
each m independently is 1 or 2;
each p independently is 1 or 2;
each $R^2$ independently is hydrogen, formyl, $C_{1-6}$alkylcarbonyl, Hetcarbonyl, pyrrolidinyl, piperidinyl, homopiperidinyl, $C_{3-7}$cycloalkyl substituted with $N(R^6)_2$, or $C_{1-10}$alkyl substituted with $N(R^6)_2$ and optionally with a second, third or fourth substituent selected from amino, hydroxy, $C_{3-7}$cycloalkyl, $C_{2-5}$alkanediyl (wherein said $C_{2-5}$alkanediyl is substituted on one carbon atom of said $C_{1-10}$alkyl substituted with $N(R^6)_2$ to form a spiro moiety), piperidinyl, mono-or di($C_{1-6}$alkyl)amino, $C_{1-6}$alkyloxycarbonylamino, aryl and aryloxy;

$R^3$ is hydrogen, hydroxy, $C_{1-6}$alkyl, $C_{1-6}$alkyloxy, aryl$C_{1-6}$alkyl or aryl$C_{1-6}$alkyloxy;

$R^4$ is hydrogen, $C_{1-6}$alkyl or aryl$C_{1-6}$alkyl;

$R^{5a}$, $R^{5b}$, $R^{5c}$ and $R^{5d}$ each independently are hydrogen or $C_{1-6}$alkyl; or $R^{5a}$ and $R^{5b}$, or $R^{5b}$ and $R^{5d}$ taken together form a bivalent radical of formula —$(CH_2)_s$— wherein s is 4 or 5;

$R^6$ is hydrogen, $C_{1-4}$alkyl, formyl, hydroxy$C_{1-6}$alkyl, $C_{1-6}$alkylcarbonyl or $C_{1-6}$alkyloxycarbonyl;

aryl is phenyl or phenyl substituted with 1 or more substituents selected from halo, hydroxy, $C_{1-6}$alkyl, hydroxy$C_{1-6}$alkyl, polyhalo$C_{1-6}$alkyl, and $C_{1-6}$alkyloxy; and Het is pyridyl, pyrimidinyl, pyrazinyl, or pyridazinyl.

2. A compound according to claim 1, wherein -$a^1$=$a^2$-$a^3$=$a^4$- is a radical of formula (a-2) or (a-3).

3. A compound according to claim 1, wherein Q is a radical of formula (b-5) wherein v is 2 and $Y^1$ is —$NR^2$—.

4. A compound according to claim 1, wherein $R^2$ is $C_{1-10}$alkyl substituted with $NHR^6$.

5. A compound according to claim 1, wherein G is a direct bond or $C_{1-10}$alkanediyl optionally substituted with one, two or three substituents selected from the group consisting of hydroxy, $C_{1-6}$alkyloxy, aryl$C_{1-6}$alkyloxy, HO(—$CH_2$—$CH_2$—O)$_n$—, $C_{1-6}$alkyloxy(—$CH_2$—$CH_2$—O)$_n$—, and aryl$C_{1-6}$alkyloxy(—$CH_2$—$CH_2$—O)$_n$—.

6. A compound according to claim 1, wherein the compound is (±)-N-[1-(2-aminoethyl)-4-piperidinyl]-7-methyl-3-(8-quinolinylmethyl)-3H-imidazo[4,5-b]pyridin-2-amine tetrahydrochloride trihydrate;

(±)-N-[1-(2-amino-3-methylbutyl)-4-piperidinyl]-7-methyl-3-(8-quinolinylmethyl)-3H-imidazo [4,5-b]pyridin-2-amine tetrahydrochloride monohydrate;

(±)-N-[1-(2-amino-3-methylbutyl)-4-piperidinyl]-1-(8-quinolinylmethyl)-1H-imidazo [4,5-c]pyridin-2-amine trihydrochloride dihydrate;

(±)-N-[1-(2-amino-3-methylbutyl)-4-piperidinyl]-1-(8-quinolinylmethyl)-1H-imidazo [4,5-b]pyridine-2-amine trihydrochloride dihydrate;

(±)-N-[1-(2-aminoethyl)-4-piperidinyl]-3-(2-quinolinyl-methyl)-3H-imidazo [4,5-b]pyridin-2-amine trihydrochloride trihydrate;

(±)-N-[1-(2-amino-3-methylbutyl)-4-piperidinyl]-3-(quinolinylmethyl)-3H-imidazo [4,5-b]pyridin-2-amine;

(±)-N-[1-(2-amino-3-methylbutyl)-4-piperidinyl]-3-(8-quinolinylmethyl)-3H-imidazo [4,5-c]pyridin-2-amine trihydrochloride tetrahydrate;

(±)-N-[1-(2-aminoethyl)-4-piperidinyl]-3-(8-quinolinyl-methyl)-3H-imidazo [4,5-b]pyridin-2-amine;

N-oxide, addition salt, quaternary amine, metal complex or stereochemically isomeric form thereof.

7. A pharmaceutical composition, comprising a pharmaceutically acceptable carrier, and as active ingredient a therapeutically effective amount of a compound according to claim 1.

8. A process of preparing a composition as claimed in claim 7, comprising the step of intimately mixing said carrier with said compound.

9. An intermediate of formula

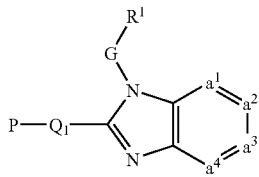

(IV)

with $R^1$, G and $-a^1=a^2-a^3=a^4-$ defined as in claim 1, P being a protective group, and $Q_1$ being defined as Q according to claim 1 but being devoided of the $R^2$ or $R^6$ substituent.

10. An intermediate of formula

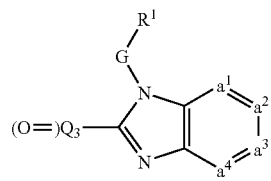

(IX)

with $R^1$, G and $-a^1=a^2-a^3=a^4-$ defined as in claim 1, and $(O=)Q_3$ being a carbonyl derivative of Q, said Q being defined according to claim 1, provided that it is devoided of the $NR^2R^4$ or $NR^2$ substituent.

11. An intermediate of formula

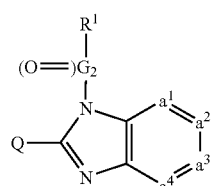

(XXII)

with $R^1$, Q and $-a^1=a^2-a^3=a^4-$ defined as in claim 1, and $(O=)G_2$ being a carbonyl derivative of G, said G being defined according to claim 1.

12. A method of treating a respiratory syncytial viral infection, comprising the step of:
administering a therapeutically effective amount of a compound according to claim 1.

* * * * *